(12) United States Patent
Suzuki

(10) Patent No.: US 10,241,316 B2
(45) Date of Patent: Mar. 26, 2019

(54) SAMPLE OBSERVATION METHOD AND SAMPLE OBSERVATION DEVICE

(71) Applicant: OLYMPUS CORPORATION, Tokyo (JP)

(72) Inventor: Yoshimasa Suzuki, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 596 days.

(21) Appl. No.: 14/835,844

(22) Filed: Aug. 26, 2015

(65) Prior Publication Data

US 2016/0025959 A1 Jan. 28, 2016

Related U.S. Application Data

(63) Continuation of application No. PCT/JP2013/078635, filed on Oct. 15, 2013.

(30) Foreign Application Priority Data

Feb. 28, 2013 (JP) .................................. 2013-040142
Feb. 28, 2013 (JP) .................................. 2013-040143

(51) Int. Cl.
*G02B 21/36* (2006.01)
*G02B 21/00* (2006.01)
(Continued)

(52) U.S. Cl.
CPC .......... *G02B 21/367* (2013.01); *G02B 5/201* (2013.01); *G02B 21/0088* (2013.01);
(Continued)

(58) Field of Classification Search
CPC ................................................. G02B 21/367
See application file for complete search history.

(56) References Cited

U.S. PATENT DOCUMENTS 5,463,426 A * 10/1995 Grinvald ................ H04N 5/142
348/180
5,754,299 A * 5/1998 Sugaya ............... G03F 7/70241
356/399
(Continued)

FOREIGN PATENT DOCUMENTS

JP H08-122648 A 5/1996
JP 2000-83184 A 3/2000
(Continued)

OTHER PUBLICATIONS

Japanese Notification of Reasons for Refusal dated Jan. 5, 2018 received in Japanese Patent Application No. 2013-040142, together with an English-language translation.
(Continued)

*Primary Examiner* — Rowina J Cattungal
(74) *Attorney, Agent, or Firm* — Scully, Scott, Murphy & Presser, P.C.

(57) ABSTRACT

A sample observation method includes an acquisition of for acquiring an electronic image of a sample, and a subtraction step of subtracting a DC component from a signal of the electronic image, and the acquisition step is performed in a state of bright-field observation, the electronic image at the subtraction step is an image acquired in a first predetermined state, and in the first predetermined state, at least a position of the sample and a in-focus position of an image forming optical system are different. A sample observation device includes a light source, an illumination optical system, an image forming optical system, an image-pickup device, and an image processing device, and the illumination optical system is disposed so as to irradiate a sample with illumination light from the light source, the image forming optical system is disposed so that light from the sample is incident thereon and an optical image of the sample is formed, the image-pickup device is disposed at a position of the optical
(Continued)

image, and the image processing device is configured to implement the aforementioned sample observation method.

12 Claims, 29 Drawing Sheets

(51) Int. Cl.
| | |
|---|---|
| *G02B 21/14* | (2006.01) |
| *G02B 5/20* | (2006.01) |
| *G02B 21/02* | (2006.01) |
| *G02B 21/12* | (2006.01) |
| *H04N 5/232* | (2006.01) |
| *H04N 7/18* | (2006.01) |
| *G02B 23/24* | (2006.01) |
| *A61B 1/00* | (2006.01) |

(52) U.S. Cl.
CPC ............ *G02B 21/02* (2013.01); *G02B 21/12* (2013.01); *G02B 21/14* (2013.01); *G02B 21/365* (2013.01); *H04N 5/23293* (2013.01); *H04N 7/183* (2013.01); *A61B 1/00009* (2013.01); *A61B 1/00188* (2013.01); *G02B 23/2469* (2013.01)

(56) References Cited

U.S. PATENT DOCUMENTS

| | | | | |
|---|---|---|---|---|
| 6,947,587 | B1* | 9/2005 | Maeda | G01N 21/95607 |
| | | | | 382/144 |
| 7,564,622 | B2 | 7/2009 | Ishiwata | |
| 8,064,661 | B2 | 11/2011 | Komori et al. | |
| 8,760,506 | B2 | 6/2014 | Alexandrov | |
| 2002/0012313 | A1* | 1/2002 | Kimura | G02B 13/18 |
| | | | | 369/112.08 |
| 2005/0094538 | A1* | 5/2005 | Ikenaka | G11B 7/1275 |
| | | | | 369/112.05 |
| 2005/0168808 | A1 | 8/2005 | Ishiwata | |
| 2008/0013090 | A1* | 1/2008 | Hagiwara | G03F 9/7026 |
| | | | | 356/400 |
| 2008/0273786 | A1 | 11/2008 | Komori et al. | |
| 2009/0201580 | A1 | 8/2009 | Ishiwata | |
| 2010/0122385 | A1* | 5/2010 | Hu | B82Y 35/00 |
| | | | | 850/5 |
| 2011/0134233 | A1 | 6/2011 | Alexandrov | |
| 2012/0026462 | A1* | 2/2012 | Uhlhorn | A61B 3/102 |
| | | | | 351/206 |
| 2012/0057013 | A1* | 3/2012 | Ishiwata | G02B 21/367 |
| | | | | 348/78 |
| 2012/0213052 | A1* | 8/2012 | Yamasaki | G11B 7/1353 |
| | | | | 369/112.05 |
| 2012/0250972 | A1* | 10/2012 | Tada | A61B 6/4291 |
| | | | | 382/132 |

FOREIGN PATENT DOCUMENTS

| | | |
|---|---|---|
| JP | 2004-354650 A | 12/2004 |
| JP | 2005-173288 A | 6/2005 |
| JP | 2007-155982 A | 6/2007 |
| JP | 2008-102294 A | 5/2008 |
| JP | 2009-145754 A | 7/2009 |
| JP | 2010-148391 A | 7/2010 |
| JP | 2011-530094 A | 12/2011 |
| WO | 2006/051813 A1 | 5/2006 |

OTHER PUBLICATIONS

Japanese-language International Preliminary Report on Patentability dated Sep. 11, 2015 issued in PCT/JP2013/078635, together with an English-language translation.
International Search Report dated Feb. 4, 2014 issued in PCT/JP2013/078635.
Agero U. et al., "Cell Surface Fluctuations Studied With Defocusing Microscopy", Physical Review E 67(5):051904 (2003).
Japanese Notification of Reasons for Refusal dated Mar. 8, 2017 received in Japanese Patent Application No. 2013-040142, together with an English-language translation.

* cited by examiner

DISTANCE BETWEEN SAMPLE AND
IMAGE FORMING OPTICAL SYSTEM

SAMPLE OBSERVATION METHOD AND SAMPLE OBSERVATION DEVICE

CROSS-REFERENCE TO RELATED APPLICATION

The present application is a continuation of PCT/JP2013/078635, filed on Oct. 15, 2013 which is based upon and claims the benefit of priority from Japanese Patent Application Nos. 2013-040142 filed on Feb. 28, 2013 and 2013-040143 filed on Feb. 28, 2013; the entire contents of which are incorporated herein by reference.

BACKGROUND OF THE INVENTION

Field of the Invention

The present invention relates to sample observation methods and sample observation devices.

Description of the Related Art

When a sample is illuminated with parallel light flux, non-diffracted light (hereinafter, referred to as "zero-order diffracted light") and diffracted light are generated from a sample. In microscopes, an image of a sample is formed by synthesis of zero-order diffracted light and diffracted light.

Complex amplitude E at the image plane is represented by the following expression, for example:

$$E = A_1 e^{-i\phi 1(r)} e^{i\omega t} + A_2 e^{-i\phi 2(r)} e^{i\omega t},$$

Where $A_1$ denotes an amplitude of zero-order diffracted light.
$A_2$ denotes an amplitude of diffracted light,
$\phi 1(r)$ denotes a phase of zero-order diffracted light, and
$\phi 2(r)$ denotes a phase of diffracted light.

Since intensity of light is observed at the image plane, the intensity I of light at the image plane can be represented by the following expression:

$$I = |E|^2 = A_1^2 + A_2^2 + 2A_1 A_2 \cos \psi,$$

where $\psi$ denotes a phase difference, and $\psi = \phi 1(r) - \phi 2 (r)$.

As described above, zero-order diffracted light and diffracted light is necessary for forming the image (optical image) of the sample. Therefore, in the following description, an image (optical image) of a sample is assumed to be formed by zero-order diffracted light and first-order diffracted light. Since the phase of first-order diffracted light delays $\pi/2$ relative to the phase of zero-order diffracted light, the phase difference is expressed by $\psi = 0 - (-\pi/2) = \pi/2$. In this case, since $2A_1 A_2 \cos \psi = 0$, phase information cannot be obtained in the form of contrast information. As a result, in attempting to observe an image of a colorless and transparent sample, e.g., cells, at an in-focus position, it is very difficult to observe the image of the cell in a bright-field observation.

A phase-contrast observation is one method to observe the colorless and transparent sample. In the phase-contrast observation, a phase-contrast microscope is used. Various proposals have been made for a phase-contrast microscope. A microscope, which makes an observation of the sample at a position displaced from the in-focus position of an image forming optical system so as to observe an image (phase-contrast image) in a wide observation field, is one available microscope. The microscope disclosed in Japanese Patent Application Laid-open Publication No. 2005-173288 (hereinafter, referred to as "JP 2005-173288 A") includes a partial aperture and wavefront introduction means. The partial aperture is located substantially at a pupil position of the illumination optical system, and the wavefront introduction means is located at the pupil position of the image forming optical system. Moreover, the wavefront introduction means introduces a wavefront that varies in size with the pupil diameter of the image forming optical system.

When the sample is displaced from the in-focus position of the image forming optical system, a difference in optical path length (phase difference) occurs between zero-order diffracted light and diffracted light. In this case, since $2A_1 A_2 \cos \psi \neq 0$, then phase information can be obtained in the form of contrast information. The value of $A_1^2$, however, is very large as compared with the value of $2A_1 A_2 \cos \psi$. Therefore, in the microscope of JP 2005-173288 A, the wavefront introduction means, i.e., an absorption film, is located at the pupil position of the image forming optical system, and whereby the value of $A_1$ is reduced.

SUMMARY OF THE INVENTION

A sample observation method of the present invention comprises:

an acquisition step of acquiring an electronic image of a sample, and a subtraction step of subtracting a DC component from a signal of the electronic image, wherein the acquisition step is performed in a state of bright-field observation, the electronic image at the subtraction step is an image acquired in a first predetermined state, and in the first predetermined state, at least a position of the sample and a in-focus position of an image forming optical system are different.

Another sample observation method of the present invention comprises:

an acquisition step of acquiring an electronic image of a sample, and a subtraction step of subtracting a DC component from a signal of the electronic image, wherein the acquisition step is performed in a state of bright-field observation, the electronic image at the subtraction step is an image acquired in a second predetermined state, before reaching the second predetermined state, a position of the sample and an in-focus position of an image forming optical system are made to be coincident using light of a first wavelength band, in the second predetermined state, an optical image of the sample is formed using light of a second wavelength band at least, and the second wavelength band is coincident with a part of the first wavelength band, or is different from the first wavelength band.

A sample observation device of the present invention comprises:

a light source,
an illumination optical system,
an image forming optical system,
an image-pickup device, and
an image processing device, wherein the illumination optical system is disposed so as to irradiate a sample with illumination light from the light source, the image forming optical system is disposed so that light from the sample is incident thereon and an optical image of the sample is formed, the image-pickup device is disposed at a position of the optical image, and the image processing device is configured to implement the sample observation method as stated above.

BRIEF DESCRIPTION OF THE DRAWINGS

FIG. 2A is a diagram showing the relationship at a time of in-focus state, and FIG. 2B is a diagram showing the relationship at a time of defocus state (displacement $\Delta Z=10$ µm).

FIG. 5A is a diagram showing the relationship at the time of in-focus state, and FIG. 5B is a diagram showing the relationship at the time of defocus state (displacement $\Delta Z=20$ µm).

FIG. 8A is a diagram showing the relationship at the time of in-focus state, and FIG. 8B is a diagram showing the relationship at the time of defocus state (displacement $\Delta Z=10$ µm).

FIG. 9A is a diagram showing the relationship at the time of in-focus state, and FIG. 9B is a diagram showing the relationship at the time of defocus state (displacement $\Delta Z=20$ µm).

FIG. 10A is a flowchart simply describing the sample observation method and FIG. 10B is a graph representing a relationship between the distance between the sample and the image forming optical system and the contrast.

FIG. 12A is a flowchart of the sample observation method of the third embodiment and the tenth embodiment, and FIG. 12B is a flowchart of the sample observation method of the fourth embodiment and the eleventh embodiment.

FIG. 13A is a diagram showing the state before performing the subtraction step, and FIG. 13B is a diagram showing the state after performing the subtraction step.

FIG. 17A is a diagram showing the schematic configuration of the sample observation device schematically, and FIG. 17B is a diagram showing the configuration of the optical system.

FIG. 18A is a diagram showing a case where the illumination light is incident in parallel with the optical axis, FIG. 18B is a diagram showing a case where the angle between the incident direction of the illumination light and the optical axis is small, and FIG. 18C is a diagram showing a case where the angle between the incident direction of the illumination light and the optical axis is large.

FIG. 21A is a diagram showing a state where the position of the sample and the in-focus position are allowed to coincide using light of the first wavelength band, and FIG. 21B is a diagram showing a state where the optical image of the sample is formed using the second wavelength band.

FIG. 24A is a diagram showing the state where the position of the sample and the in-focus position are allowed to coincide using light of the first wavelength band, and FIG. 24B is a diagram showing the state where the optical image of the sample is formed using the second wavelength band.

FIG. 29A is a diagram showing the configuration of the observation device schematically, and FIG. 29B is a diagram showing the configuration of the optical system.

DETAILED DESCRIPTION OF THE INVENTION

Figure 1:
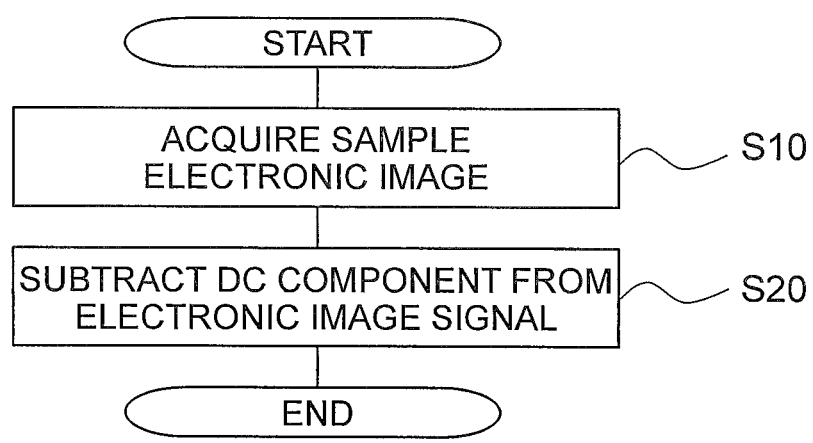
FIG. 1 is a flowchart of sample observation method of a first embodiment and a ninth embodiment.

Functions and advantageous effects of embodiments according to certain aspects of the present invention are described below. The following specifically describes the functions and advantageous effects of these embodiments, byway of specific examples. However, the aspects exemplified thereof are simply apart of the aspects of the present invention, and they may have a lot of variations. Therefore, the present invention is not restricted to the aspects illustrated in the following.

A sample observation method of an embodiment and a sample observation device of an embodiment are described below. The sample observation methods from the first embodiment to the eight embodiment and the sample observation devices from the first embodiment to the third embodiment are used in the state of bright-field observation. In the bright-field observation of these embodiments, a fluorescent mirror unit including an excitation filter, a dichroic mirror, and an absorption filter, which is used in the fluorescent observation, is not used. Therefore, in the state of bright-field observation, when the sample is colorless and transparent, a wavelength band of light which forms an image of the sample is partially coincident with a wavelength band of light which illuminates the sample, or the wavelength band of the image forming light is coincident with the wavelength band of the illumination light. Hereinafter, the light which forms an image of the sample is referred to as "image forming light" as appropriate, and the light which illuminates the sample is referred to as "illumination light" as appropriate.

Moreover, in the bright-field observation of the present embodiment, a phase film, which is used in the phase-contrast observation, and a differential interference prism, which is used in the differential interference observation, are not used. Therefore, considering light emanated from one point of the sample, a change in wavefront of light at the illumination optical system and a change in wavefront at the image forming optical system both occur at a lens only.

Moreover, in the bright-field observation of the present embodiment, a neutral density filter, which is for partially dimming of light flux from the sample, is not used. Therefore, in the state of bright-field observation, a change of intensity in the image forming light does not arise from the sample to the image of the sample (excluding a change in intensity resulting from a lens).

A sample observation method of the first embodiment includes an acquisition step of acquiring an electronic image of a sample, and a subtraction step of subtracting a DC component from a signal of the electronic image, and the acquisition step is performed in the state of bright-field observation, and the electronic image at the subtraction step is an image acquired in a first predetermined state, and in the first predetermined state, at least the position of the sample and the in-focus position of the image forming optical system are different.

Referring to FIG. 1, the sample observation method of the first embodiment is described below. FIG. 1 is a flowchart of the sample observation method of the first embodiment and the sample observation method of the ninth embodiment described later.

The sample observation method of the first embodiment includes an acquisition step S10 and a subtraction step S20. Accordingly, in the sample observation method of the first embodiment, it is possible to acquire a clear electronic image.

In the sample observation method of the first embodiment, the acquisition step S10 is executed firstly. At the acquisition step S10, an electronic image of the sample is acquired. The image (optical image) of the sample is formed by the image forming optical system. At a time of acquiring the electronic image, the image of the sample is picked up by an image-pickup element, such as a CCD or a CMOS. The image of the sample is converted into an electronic image (digital data) through the image pickup. Since the image of the sample is formed in the state of bright-field observation, an acquisition of the electronic image also is performed in the state of bright-field observation. Hereinafter, the electronic image of the sample is referred to as "electronic image" as appropriate.

When the acquisition step S10 ends, the subtraction step S20 is executed. At the subtraction step S20, a DC component (bias component) is subtracted from a signal of the electronic image. The electronic image at the subtraction step S20 is an image acquired in a first predetermined state. In this first predetermined state, at least the position of the sample and the in-focus position of the image forming optical system are different. Hereinafter, the in-focus position of the image forming optical system is referred "in-focus position" as appropriate.

In order to make the position of the sample to be different from the in-focus position of the image forming optical system, the sample may be moved by eye of the operator to a position where the operator thinks it being displaced from the in-focus position, for example. Alternatively, after letting the position of the sample to be coincident with the in-focus position firstly, then the sample may be moved in the direction away from the in-focus position. Alternatively, when the in-focus position is known beforehand, since a position displaced from the in-focus position can be decided beforehand, the sample may be moved to such position.

The electronic image at the subtraction step S20 is an image at a time that the position of the sample and the in-focus position are different at least. Therefore, at a time of acquiring the electronic image, the state where the position of the sample and the in-focus position are different, i.e., the state where the sample is displaced from the in-focus position is included.

Here, if the sample is a lattice-like phase object, when the sample is illuminated with light, zero-order light and diffracted light emanate from the sample. In the state where the sample is displaced from the in-focus position, a difference in wavefront aberration (difference in optical path length) occurs between zero-order light and diffracted light. This point is described with reference to FIG. 2A and FIG. 2B to FIG. 9A and FIG. 9B. In the following description, first-order diffracted light is used as the diffracted light. Moreover, the image forming optical system is assumed to have no aberration. A difference between the in-focus position of the image forming optical system and the position of the sample, i.e., the displacement of the sample from the in-focus position is referred to as "displacement $\Delta Z$" as appropriate.

Figure 2A:
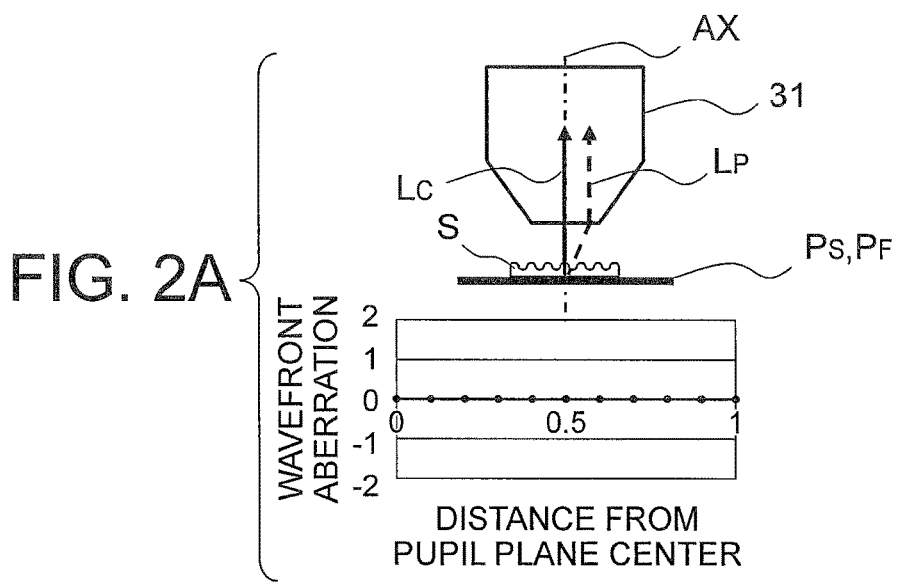
FIG. 2A and FIG. 2B are diagrams showing relationship between sample position and in-focus position, and an amount of wavefront aberration, where
Figure 2B:
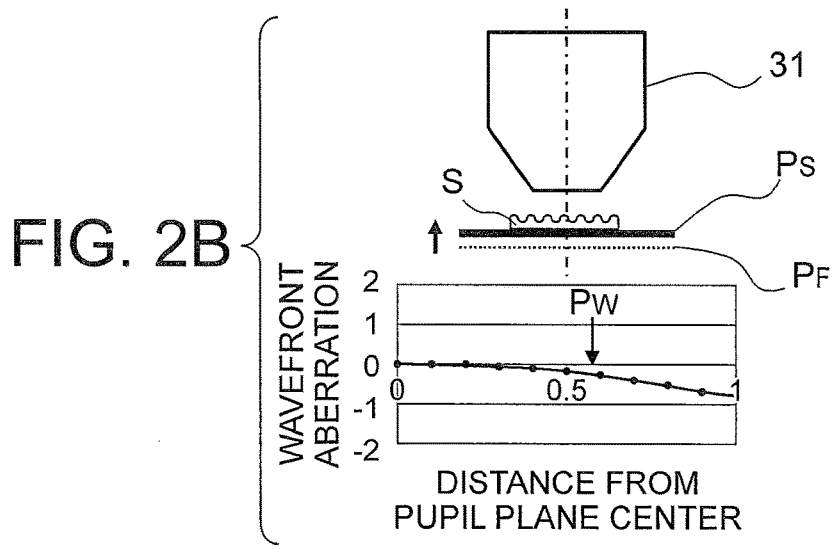
Figure 3:
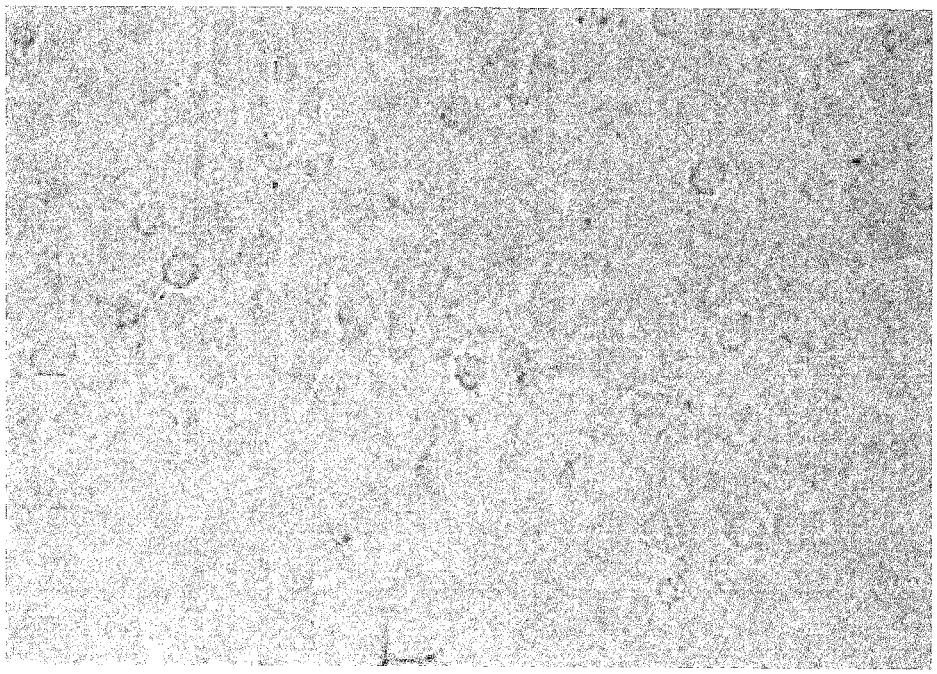
FIG. 3 is an electronic image of the sample at the time of in-focus state.
Figure 4:
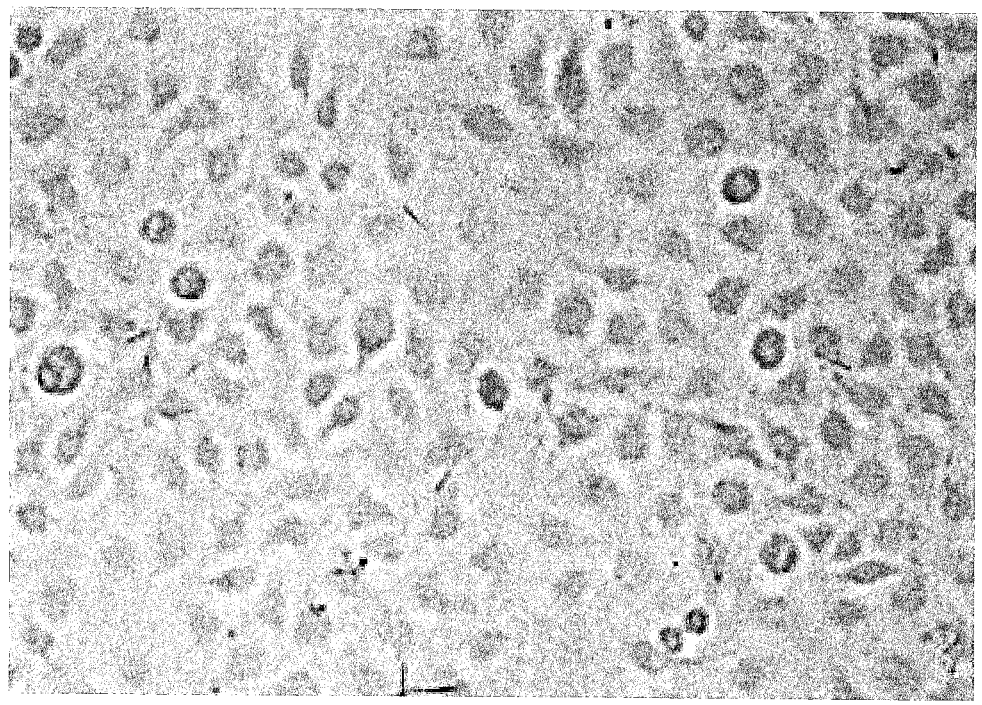
FIG. 4 is an electronic image of the sample at the time of defocus state (displacement $\Delta Z=10$ µm).
Figure 5A:
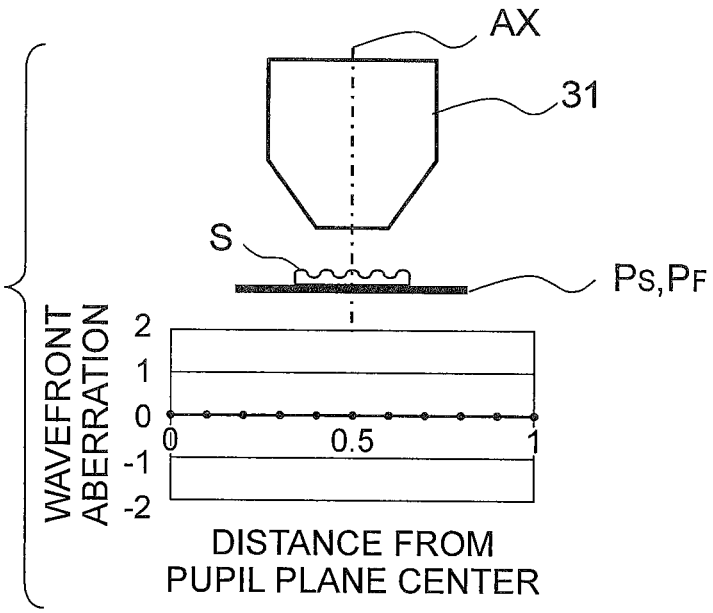
FIG. 5A and FIG. 5B are diagrams showing the relationship between the sample position and the in-focus position, and the amount of wavefront aberration, where
Figure 5B:
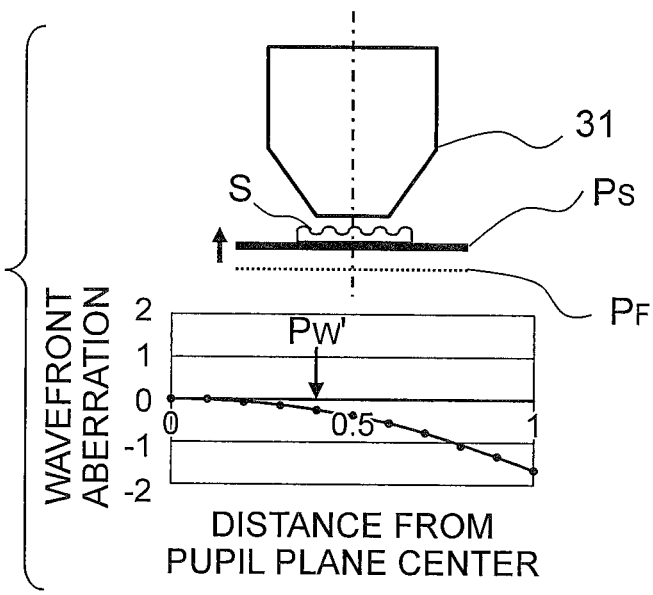
Figure 6:
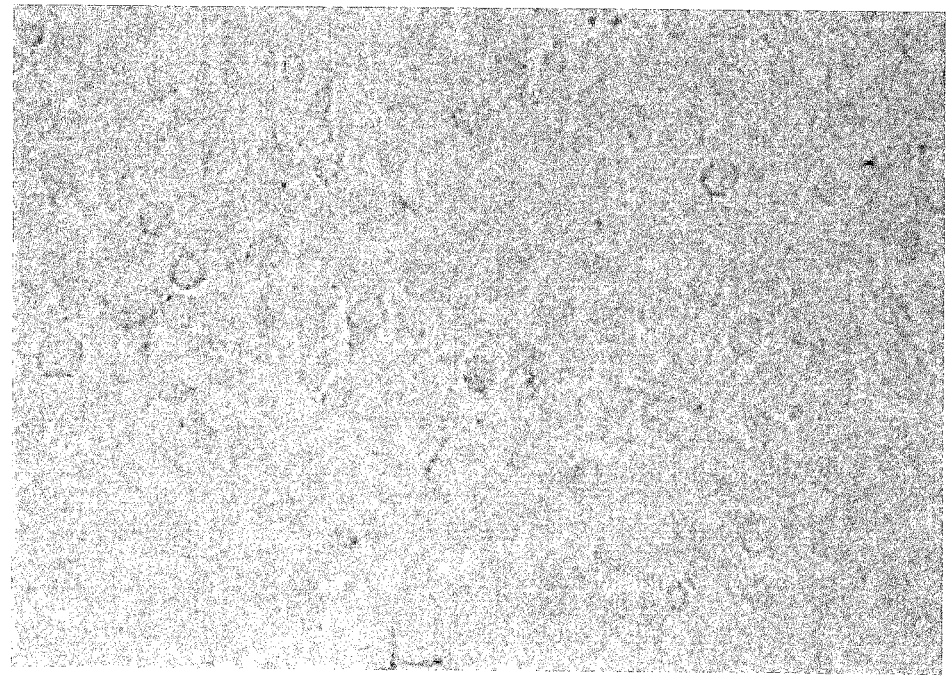
FIG. 6 is an electronic image of the sample at the time of in-focus state.
Figure 7:
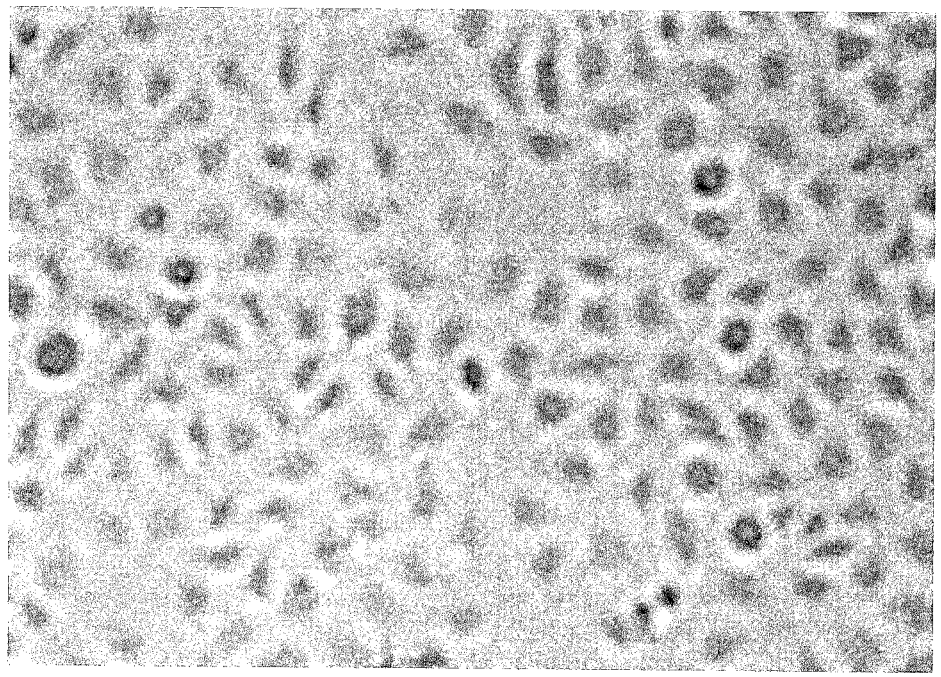
FIG. 7 is an electronic image of the sample at the time of defocus state (displacement $\Delta Z=20$ µm).

FIG. 2A and FIG. 2B are diagrams showing the relationship between the sample position and the in-focus position, and the wavefront aberration, where FIG. 2A is a diagram showing the relationship at a time of in-focus state, and FIG. 2B s a diagram showing the relationship at a time of defocus state (displacement $\Delta Z=10$ μm). FIG. 3 is an electronic image of the sample at the time of in-focus state. FIG. 4 is an electronic image of the sample at the time of defocus state (displacement $\Delta Z=10$ μm). FIG. 5A and FIG. 5B are diagrams showing the relationship between the sample position and the in-focus position, and the amount of wavefront aberration, where FIG. 5A is a diagram showing the relationship at the time of in-focus state, and FIG. 5B is a diagram showing the relationship at the time of defocus state (displacement $\Delta Z=20$ μm). FIG. 6 is an electronic image of the sample at the time of in-focus state. FIG. 7 is an electronic image of the sample at the time of defocus state (displacement $\Delta Z=20$ μm). Each electronic image in FIG. 3, FIG. 4, FIG. 6 and FIG. 7 is an image after executing the subtraction step S20. Moreover, each sample in FIG. 3, FIG. 4, FIG. 6 and FIG. 7 is a cell.

Moreover, in-focus state means the state where the position of the sample S coincides with the in-focus position, and defocus state means the state where the sample S is displaced from the in-focus position. The direction of the displacement is in the upward direction for both of FIG. 2B and FIG. 5B (the direction toward an image forming optical system 31).

Moreover, spatial frequency of the sample S is different between in FIG. 2A and FIG. 2B and in FIG. 5A and FIG. 5B. The sample S shown in FIG. 2A and FIG. 2B, and the sample S shown in FIG. 5A and FIG. 5B are both the lattice-like phase object. In the sample S shown in FIG. 2A and FIG. 2B, spatial frequency is high (pitch of concavity and convexity of the phase is short). On the other hand, in the sample S shown in FIG. 5A and FIG. 5B, spatial frequency is low compared with the sample S shown in FIG. 2A and FIG. 2B (pitch of concavity and convexity of the phase is long compared with the sample S shown in FIG. 2A and FIG. 2B).

Moreover, the graphs represent an amount of wavefront aberration at the pupil position. The vertical axis of the graphs represents the amount of wavefront aberration (in the unit of wavelength), and the horizontal axis represents the distance from the center of the pupil plane (on the pupil plane). Since the distance from the center of the pupil plane is normalized, they are unitless numbers. The numerical value 0 on the horizontal axis represents the center position of the pupil plane, and 1 represents the outermost position of the pupil plane.

As shown in FIG. 2A, in light emanated from one point on the optical axis, light ray $L_C$ and light ray $L_P$ are included. The light ray $L_C$ travels along the optical axis. Here, a point at the intersection of the light ray $L_C$ with the pupil plane coincides with the center position of the pupil plane. On the other hand, the light ray $L_P$ is a light ray which is incident on the image forming optical system 31 at a predetermined angle with respect to the optical axis AX. Here, a point at the intersection of the light ray $L_P$ with the pupil plane coincides with a position away from the center of the pupil plane by a predetermined distance.

When the sample S is illuminated with illumination light (parallel light flux), zero-order diffracted light and first-order diffracted light emanate form the sample S. Here, taking notice of the point where the sample S and the optical axis intersect (one point on the optical axis), since zero-order diffracted light is not diffracted, zeroth-diffracted light emanated from this point travels along the optical axis and reaches the center of the pupil. Therefore, zero-order diffracted light can be considered as the light ray $L_C$. On the other hand, since first-order diffracted light is diffracted in a predetermined direction, the first-order diffracted light emanated from this point is incident on the image forming optical system 31 at a predetermined angle with respect to the optical axis. The first-order diffracted light incident on the image forming optical system 31 reaches a position away from the center of the pupil plane. Therefore, first-order diffracted light can be considered as the light ray $L_P$.

Firstly, the case where the sample S has a high spatial frequency is described below. In the in-focus state, the position $P_S$ of the sample S coincides with the in-focus position $P_F$. In this state, as shown in the graph of FIG. 2A, an amount of wavefront aberration is 0 at any place on the pupil plane. This indicates that the amount of wavefront aberration in zero-order diffracted light and the amount of wavefront aberration in first-order diffracted light are both 0. A value obtained by multiplying the amount of wavefront aberration by $(2\pi/\lambda)$ is equivalent to the phase amount. At a time of in-focusing, a change in phase does not arise for both of the zero-order diffracted light and the first-order diffracted light. Since the phase of the first-order diffracted light remains to be delayed relative to the phase of the zero-order diffracted light by $\pi/2$, the phase difference is expressed by $\psi=0-(-\pi/2)=\pi/2$. In this case, since $2A_1A_2 \cos \psi=0$, phase information cannot be obtained in the form of contrast information. As a result, the electronic image becomes an image without contrast.

However, in an actual image forming optical system, axial chromatic aberration remains. Therefore, when the sample is illuminated with white light, the position $P_S$ of the sample S and the in-focus position $P_F$ do not coincide in some wavelengths. In this case, light having a wavelength that the amount of wavefront aberration is added to the first-order diffracted light, is included in the image forming light. Therefore, originally, the electronic image is an image without contrast, but actually, the electronic image becomes an image with a little bit of contrast as shown in FIG. 3.

On the other hand, in the defocus state, the position $P_S$ of the sample is displaced from the in-focus position $P_F$. In FIG. 2B, the position $P_S$ of the sample S is displaced upward (direction toward the image forming optical system 31) from the in-focus position $P_F$. In this state, as shown in the graph of FIG. 2B, although the amount of wavefront aberration is 0 at the center of the pupil plane, the wavefront aberration occurs at a position away from the center of the pupil. Here, the wavefront aberration is a displacement of actual wavefront with reference to a reference wavefront, and this displacement is a displacement in phase. Therefore, if the first-order diffracted light is positioned in the range where wavefront aberration occurs, the phase of the first-order diffracted light is equivalent to a phase that the amount of wavefront aberration is added to the original phase of the first-order diffracted light. As just described, by displacing the position $P_S$ of the sample S from the in-focus position $P_F$, it is possible to change the phase of the first-order diffracted light.

As shown in the graph of FIG. 2B, the amount of wavefront aberration at the position $P_W$ is $-\lambda/4$. Therefore, the displacement $\Delta Z$ from the in-focus position $P_F$ is adjusted so that the position of the first-order diffracted light on the pupil plane coincides with the position $P_W$. In other words, the displacement $\Delta Z$ is adjusted so that the amount of wavefront aberration is equivalent to $-\lambda/4$ at the position of the first-order diffracted light on the pupil plane. In FIG. 2B, by setting the displacement $\Delta Z$ at 10 μm, the position of the first-order diffracted light on the pupil plane can coincide with the position $P_W$.

By doing so, it is possible to make the amount of wavefront aberration at the first-order diffracted light $-\lambda/4$ while keeping the amount of wavefront aberration at the zero-order diffracted light 0. As described above, since the value obtained by multiplying the amount of wavefront aberration by $(2\pi/\lambda)$ equals the phase amount, at a time of defocusing, a change in phase does not arise for the zero-order diffracted light, but a change in phase arise for the first-order diffracted light. Specifically, in the first-order diffracted light, the phase further delays by $\lambda/4\times(2\pi/\lambda)=\pi/2$ in addition to the original phase delay of $\pi/2$. Since the phase of the first-order diffracted light delays by $\pi$ relative to the phase of the zero-order diffracted light, the phase difference is expressed by $\psi=0-(-\pi)=\pi$. In this case, since $2A_1A_2 \cos \psi \neq 0$, phase information can be obtained in the form of contrast information. As a result, as shown in FIG. 4, the electronic image becomes an image with obvious contrast. Therefore, by displaying this electronic image on a display device, for example, an observer can observe the sample S (image of the sample S) clearly.

Next, the case where the sample S has a low spatial frequency is described below. In the in-focus state, the position $P_S$ of the sample S coincides with the in-focus position $P_F$. In this state, as shown in the graph of FIG. 5A, the amount of wavefront aberration is 0 at any place on the pupil plane. This is the same as in FIG. 2A. Therefore, the electronic image becomes an image without contrast. However, for the reason as stated above, the electronic image becomes an image with a little bit of contrast as shown in FIG. 6.

On the other hand, in the defocus state, as shown in FIG. 5B, the position $P_S$ of the sample S is displaced upward (direction toward the image forming optical system) from the in-focus position $P_F$. In this state, as shown in the graph of FIG. 5B, although the amount of wavefront aberration is 0 at the center of the pupil plane, the wavefront aberration occurs at a position away from the center of the pupil. Here, a structure of the sample S shown in FIG. 5A and FIG. 5B is different from that of the sample S shown in FIG. 2A and FIG. 2B.

In this case, the diffraction angle of the first-order diffracted light differs between FIG. 5B and FIG. 2B. The diffraction angle in FIG. 5B is smaller than that of FIG. 2B. For this reason, the position of the first-order diffracted light at the pupil plane also differs between FIG. 5B and FIG. 2B. As shown in the graph of FIG. 5B, the position where the amount of wavefront aberration is equivalent to $-\lambda/4$ becomes $P_W'$. The position $P_W'$ is closer to the center of the pupil plane than the position $P_W$ shown in FIG. 2B.

As described above, the amount of wavefront aberration at the position $P_W'$ is $-\lambda/4$. Therefore, the displacement $\Delta Z$ is adjusted so that the position of the first-order diffracted light on the pupil plane coincides with the position $P_W'$. In other words, the displacement $\Delta Z$ is adjusted so that the amount of wavefront aberration is equivalent to $-\lambda/4$ at the position of the first-order diffracted light on the pupil plane. In FIG. 5B, by setting the displacement $\Delta Z$ at 20 μm, the position of the first-order diffracted light on the pupil plane can coincide with the position $P_W'$.

By doing so, it is possible to make the amount of wavefront aberration at the first-order diffracted light $-\lambda/4$ while keeping the amount of wavefront aberration at the zero-order diffracted light 0. This is the same as in FIG. 2B. Therefore, as shown in FIG. 7, the electronic image becomes an image with obvious contrast. As a result, the observer can observe the sample S (image of the sample S) clearly.

In FIG. 2B and FIG. 5B, the amount of wavefront aberration at the first diffracted light is $-\lambda/4$. In this case, a relationship between the phase of zero-order diffracted light and the phase of first-order diffracted light is a relationship of opposite phase. In the relationship of the opposite phase, the zero-order diffracted light and the first-order diffracted light are mutually weakened. Therefore, in the electronic image, brightness of the sample S becomes dark as compared with the background. This corresponds to dark contrast in phase-contrast observation.

Moreover, diffraction angle of the diffracted light differs depending on the spatial frequency of the sample S. For instance, when the sample S is a lattice-like phase object, spacing of the lattice is wide means that a spatial frequency included in the sample S is low. On the other hand, spacing of the lattice is narrow means that a spatial frequency included in the sample S is high. Here, as the spacing of the lattice becomes wide the diffraction angle becomes small, and the spacing of the lattice becomes narrow the diffraction angle becomes large. Therefore, when the sample S has a low spatial frequency, the diffraction angle is small, and when the sample S has a high spatial frequency, the diffraction angle is large.

Many structures having various spatial frequencies are included in cells. Therefore, when the sample S is cells, the appearance of the image of the sample changes depending on that the position having the amount of wavefront aberration of $-\lambda/4$ is made to be coincident with the position of the first-order diffracted light at a spatial frequency of various spatial frequencies.

When the displacement $\Delta Z$ is adjusted so that the amount of wavefront aberration becomes $-\lambda/4$ at a position of the first-order diffracted light at high spatial frequency (adjustment 1), in the electronic image, a part having the high spatial frequency will be clear. On the other hand, when the displacement $\Delta Z$ is adjusted so that the amount of wavefront aberration becomes $-\lambda/4$ at a position of the first-order diffracted light at a low spatial frequency (adjustment 2), in the electronic image, a part having the low spatial frequency will be clear.

FIG. 4 is an electronic image by adjustment 1, and FIG. 7 is an electronic image by adjustment 2. The sample of FIG. 4 and the sample of FIG. 7 are the same. When comparing the electronic images of FIG. 4 with the electronic images of FIG. 7, it is possible to recognize while the outer region of cells (part having a high spatial frequency) is clear in the electronic image of FIG. 4, the inner region of cells (part having a low spatial frequency) is clear in the electronic image of FIG. 7.

Figure 8A:
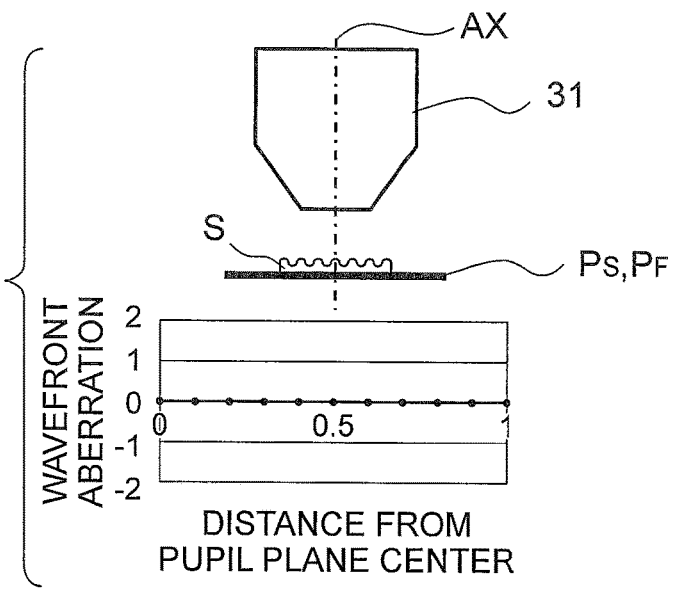
FIG. 8A and FIG. 8B are diagrams showing the relationship between the sample position and the in-focus position, and the amount of wavefront aberration, where
Figure 8B:
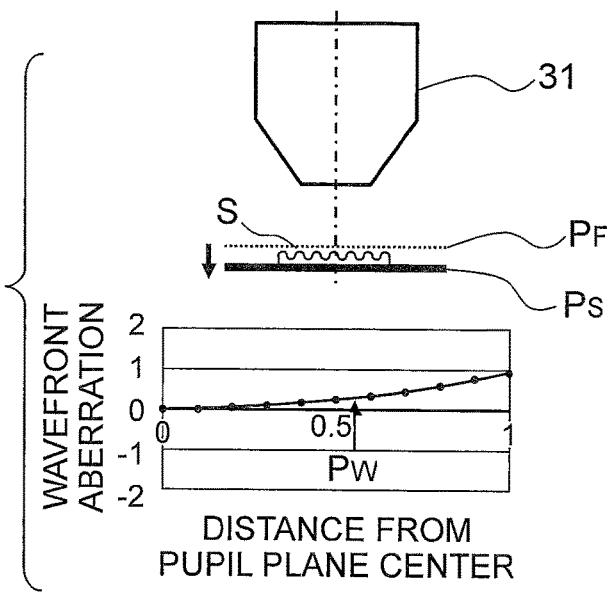
Figure 9A:
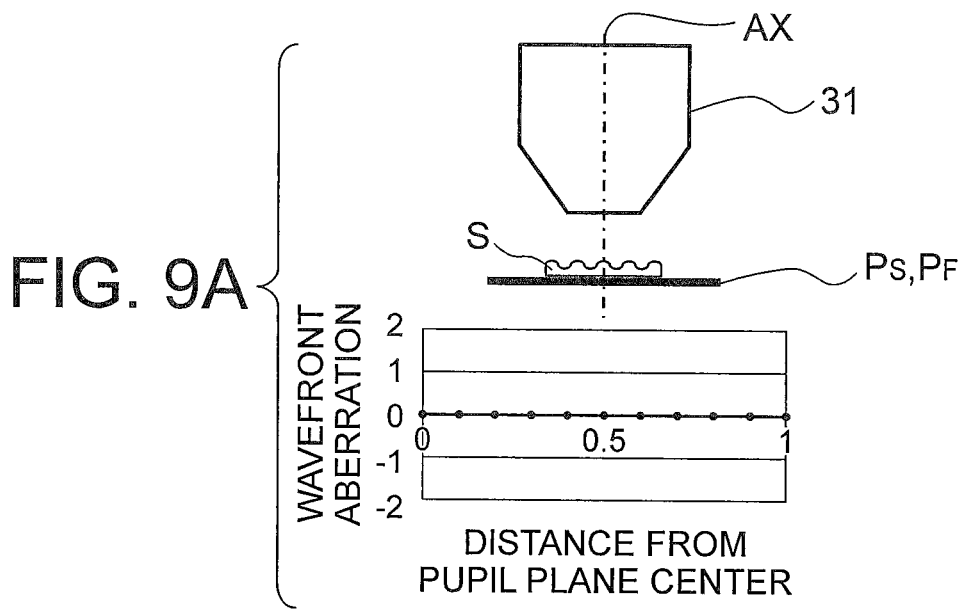
FIG. 9A and FIG. 9B are diagrams showing the relationship between the sample position and the in-focus position, and the amount of wavefront aberration, where
Figure 9B:
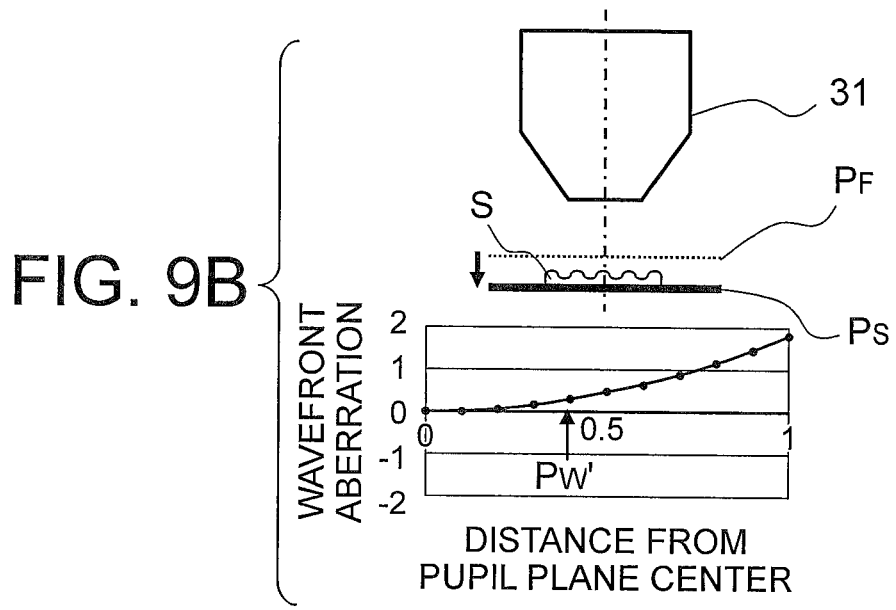

Moreover, the direction of the displacement may be in a downward direction (direction away from the image forming optical system 31). FIG. 8A, FIG. 8B, FIG. 9A, and FIG. 9B show such a state. Since detailed descriptions of FIG. 8A and FIG. 8B are the same as in FIG. 2A and FIG. 2B, and detailed descriptions of FIG. 9A and FIG. 9B are the same as in FIG. 5A and FIG. 5B, they are omitted.

FIG. 8A and FIG. 8B are diagrams showing the relationship between the sample position and the in-focus position, and the amount of wavefront aberration, where FIG. 8A is a diagram showing the relationship at the time of in-focus state, and FIG. 8B is a diagram showing the relationship at the time of defocus state (displacement $\Delta Z=10$ μm). FIG. 9A and FIG. 9B are diagrams showing the relationship between the sample position and the in-focus position, and the amount of wavefront aberration, where FIG. 9A is a diagram showing the relationship at the time of in-focus state, and FIG. 9B is a diagram showing the relationship at the time of defocus state (displacement $\Delta Z=20$ μm).

In FIG. 8B and FIG. 9B, the amount of wavefront aberration at the first-order diffracted light is $+\lambda/4$. In this case, a relationship between the phase of zero-order diffracted light and the phase of first-order diffracted light is a relationship of same phase. In the relationship of the same phase, the zero-order diffracted light and the first-order diffracted light are mutually strengthened. Therefore, in the electronic image, brightness of the sample S becomes bright as compared with the background. This corresponds to bright contrast in phase-contrast observation.

Moreover, although the electronic images are not shown, the diffraction angle of the first-order diffracted light is larger in FIG. 8B than in FIG. 9B. Therefore, while the outer region of cells (part having a high spatial frequency) is clear in the electronic image of FIG. 8B, the inner region of cells (part having a low spatial frequency) is clear in the electronic image of FIG. 9B.

In the observation method of the present embodiment, the displacement ΔZ is not so large. In this case, even if the sample S is displaced relative to the in-focus position, the position where the first-order diffracted light is incident on the image forming optical system 31 hardly changes. For this reason, a change of the position of the first-order diffracted light on the pupil plane also can be considered as slight. Therefore, the amount of wavefront aberration added to the first-order diffracted light can be set at −λ/4 simply by moving the position of the sample S.

When the acquisition step S10 ends, the subtraction step S20 then is executed. At the subtraction step S20, a DC component (bias component) is subtracted from a signal of the electronic image.

As stated above, at the acquisition step S10, the sample position and the in-focus position are different. Therefore, $2A_1A_2 \cos \psi \neq 0$ holds. In this case, the intensity I of light at the image plane can be represented by the following expression:

$$I = A_1^2 + A_2^2 + 2A_1A_2 \cos \psi.$$

Here, $A_1^2 + A_2^2$ represents the DC component (bias component) at the image of the sample, i.e., the DC component (bias component) of a signal of the electronic image. Among them, the amplitude $A_1^2$ of the zero-order diffracted light has a very large value. Therefore, at the subtraction step S20, the value of $A_1^2$ is made smaller. By doing so, it is possible to make the value of $2A_1A_2 \cos \psi$ relatively large with reference to the value of $A_1^2 + A_2^2$. As a result, it is possible to observe the sample S (image of the sample S) clearly.

As stated above, according to the sample observation method of the first embodiment, it is possible to observe a colorless and transparent sample clearly in the state of bright-field observation as well.

The sample observation method of the second embodiment includes a comparison step after the subtraction step, and the acquisition step is performed at least three times, and an electronic image acquired earlier and an electronic image acquired later are compared at the comparison step, and the procedure from the acquisition step to the comparison step is repeated until an electronic image which satisfy a predetermined condition is acquired.

Figure 10A:
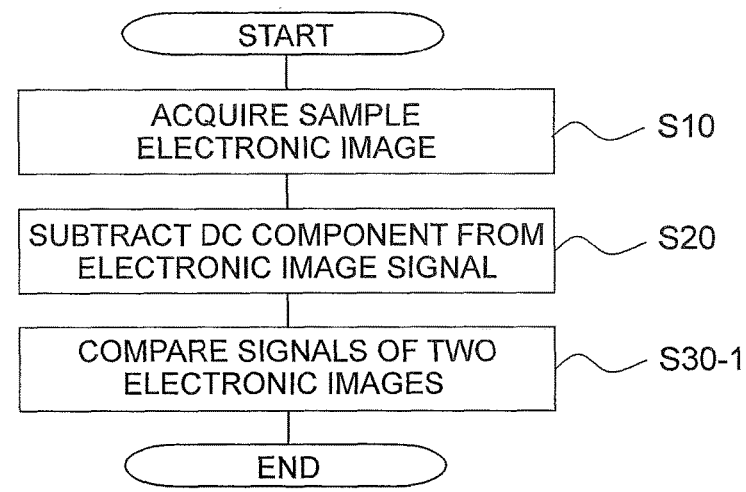
FIG. 10A and FIG. 10B are diagrams showing a sample observation method of the second embodiment, where
Figure 10B:
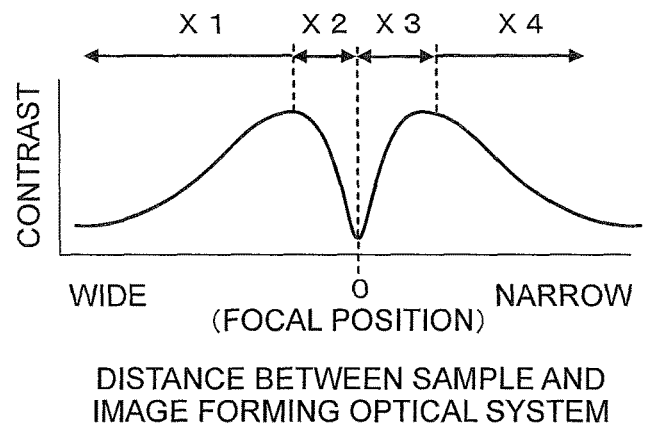
Figure 11:
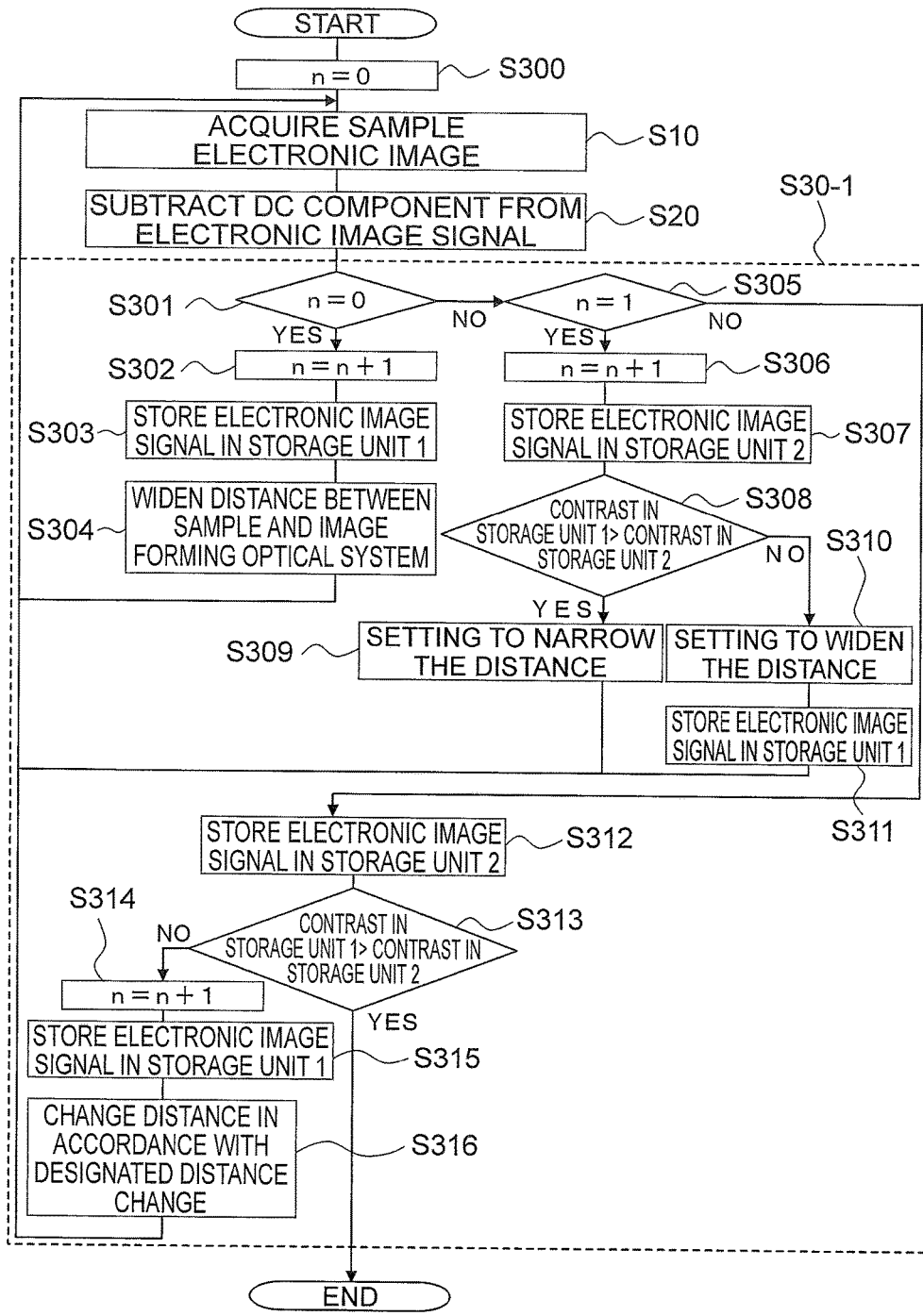
FIG. 11 is a flowchart describing the sample observation method of the second embodiment in details.

Referring to FIG. 10A, FIG. 10B, and FIG. 11, a sample observation method of the second embodiment is described below. FIG. 10A is a flowchart simply describing the sample observation method of the second embodiment, and FIG. 10B is a graph representing the relationship between the distance between the sample and the image forming optical system and the contrast. FIG. 11 is a flowchart describing the sample observation method of the second embodiment in details.

As illustrated in FIG. 10A, the sample observation method of the second embodiment includes a comparison step S30-1 in addition to the acquisition step S10 and the subtraction step S20. The comparisons step S30-1 is executed after the subtraction step S20. The acquisition step S10 is performed at least three times, and an electronic image acquired earlier and an electronic image acquired later are compared at the comparison step S30-1. Moreover, the procedure from the acquisition step S10 to the comparison step S30-1 is performed repeatedly until an electronic image satisfying a predetermined condition is acquired.

Accordingly, in the sample observation method of the second embodiment, it is possible to acquire a clearer electronic image automatically.

Contrast is one of criteria to evaluate the quality of electronic images. As illustrated in FIG. 10B, the contrast changes with a distance between the sample S and the image forming optical system 31 (hereinafter, referred to as "distance D" as appropriate). As the distance D becomes narrower from a wide state, the contrast gradually increases in the section X1, and then in the section X2, the contrast gradually decreases. Then in the section X3, the contrast gradually increases, and in the section X4 the contrast gradually decreases.

Therefore, in order to acquire an electronic image with high quality, the distance D may be set at a distance having large contrast. That is, the distance D may be set at a distance at a boundary part between the section X1 and the section X2 (hereinafter, referred to as "distance DM1" as appropriate), or at a distance at a boundary part between the section X3 and the section X4 (hereinafter, referred to as "distance DM2" as appropriate).

However, In the contrast curve shown in FIG. 10B, distances D which has a same contrast is exist in each section of the sections X1 to X4 depending on a value of contrast. Therefore, it is necessary to specify that the distance when an electronic image is acquired firstly (hereinafter, referred to as "distance D1" as appropriate) exists in what section among the sections X1 to X4.

When a contrast of an electronic image which is acquired firstly is low, it is necessary to make that the contrast becomes large. However, narrowing of the distance D from a wide state, the contrast gradually increases in the sections X1 and X3, but the contrast gradually decreases in the sections X2 and X4. Therefore, it is necessary to specify whether to widen or narrow the distance D so as to make the contrast larger.

Therefore, at the comparison step S30-1, a comparison is made while considering these points. Referring to FIG. 11, the sample observation method of the second embodiment is described in more details.

Firstly, to count the number of acquisitions, 0 is set at a variable n (S300). Next, the acquisition step S10 (first time) and the subtraction step S20 are executed. At this acquisition step S10, an electronic image is acquired with the distance D1.

Next, the number of acquisitions is determined (S301). Herein, since the value of the variable n is 0, the determination result at S301 is YES. Therefore, 1 is added to the variable n (S302), and the electronic image acquired is stored at a storage unit 1 (S303). Further, the distance (distance D) between the sample S and the image forming optical system 31 is widened by a predetermined amount (S304). The predetermined amount is assumed to be set beforehand.

When S304 ends, then the acquisition step S10 is executed again (second time). At this time, an electronic image is acquired with a wider distance D than the distance D1. Then the subtraction step S20 is executed, and the number of acquisitions is determined (S301, S305). Herein, since the value of the variable n is 1, the determination result at S301 is NO, and the determination result at S305 is YES. Therefore, 1 is added to the variable n (S306), and the electronic image acquired is stored at a storage unit 2 (S307).

Next, comparison of contrast is made between the electronic image in the storage unit 1 and the electronic image in the storage unit 2 (S308). Herein, when the determination result is YES, i.e., when contrast of the electronic image in the storage unit 1>contrast of the electronic image in the storage unit 2, then the distance D1 exists in the section X1 or in the section X3.

When distance D1 exists in the section X1 or in the section X3, the distance D may be narrowed so as to increase the contrast. Therefore, setting is made to narrow the distance D (S309). Although not shown in the flowchart, the distance D may be narrowed by a predetermined amount as well at S309. The predetermined amount here may be the same amount as the predetermined amount at S304 or may be different.

On the other hand, when the determination result is NO, i.e., when contrast of the electronic image in the storage unit 1<contrast of the electronic image in the storage unit 2, then the distance D1 exists in the section X2 or in the section X4.

When distance D1 exists in the section X2 or in the section X4, the distance D may be widened so as to increase the contrast. Therefore, setting is made to widen the distance D (S310). Although not shown in the flowchart, the distance D may be widened by a predetermined amount as well at S310. The predetermined amount here may be the same amount as the predetermined amount at S304 or may be different. Further, the electronic image stored in the storage unit 2 is stored in the storage unit 1 (S311). By doing so, the electronic image acquired earlier is stored in the storage unit 1.

Here, although the processing from S301 to S311 are included in comparison step S30-1, the processing from S301 to S311 may be performed only once. Therefore, even when the procedure from the acquisition step S10 to the comparison step S30-1 is repeated, the processing from S301 to S311 is not repeated.

When S309 or S311 ends, then the acquisition step S10 is executed again (third time). At this time, an electronic image is acquired with a distance D that is widened or narrowed by a predetermined amount. Then the subtraction step S20 is executed, and the number of acquisitions is determined (S301, S305). Herein, since the value of the variable n is 3, the determination result at S301 is NO, and the determination result at S305 also is NO. Then, the electronic image acquired is stored in the storage unit 2 (S312). By doing so, the electronic image acquired later is stored in the storage unit 2.

Next, comparison of contrast is made between the electronic image in the storage unit 1 and the electronic image in the storage unit 2 (S313). Here, in this comparison, following condition is used as a predetermined condition, contrast of the electronic image in the storage unit 1>contrast of the electronic image in the storage unit 2.

Moreover, an electronic image with high contrast is always stored in the storage unit 1.

When the determination result is YES, i.e., when contrast of the electronic image in the storage unit 1>contrast of the electronic image in the storage unit 2, this means that the predetermined condition is satisfied. Since this shows that an electronic image with sufficiently high contrast can be obtained, then the comparison ends.

On the other hand, when the determination result is NO, i.e., when contrast of the electronic image in the storage unit 1<contrast of the electronic image in the storage unit 2, this means that the predetermined condition is not satisfied. This means that the electronic image acquired does not have sufficiently high contrast. Therefore, 1 is added to the variable n (S314), and the electronic image acquired is stored in the storage unit 1 (S315).

Further, the distance D is changed by a predetermined amount in accordance with the designated distance variation (S316). The designated distance variation means a variation to narrow the distance D (setting at S309) or a variation to widen the distance D (setting at S310).

After S316 ends, the acquisition step S10 is executed again. The following procedure is repeatedly performed until the determination result at S313 becomes YES. When the determination result is YES, the comparison ends.

As just described, in the sample observation method of the second embodiment, the processing is repeated until the determination result at S313 becomes YES. It is possible to acquire an electronic image with sufficiently high contrast automatically by executing such repeated processing. As a result, it is possible to observe the sample S (image of the sample S) more clearly.

At S313, the predetermined condition is set as contrast of the electronic image in the storage unit 1>contrast of the electronic image in the storage unit 2.

Alternatively, the predetermined condition may be set so that a difference in contrast between two electronic images is smaller than a permissible value E as below,

|contrast of the electronic image in the storage unit 1−contrast of the electronic image in the storage unit 2|<E.

Moreover, in the flowchart of FIG. 11, when the distance D1 exists in the section X1 or the section X2, the electronic image acquired finally will be an image with the distance DM1. On the other hand, when the distance D1 exists in the section X3 or the section X4, then the electronic image acquired finally will be an image with the distance DM2.

However, an electronic image with the distance DM2 may be acquired by adding another processing when the distance D1 exists in the section X1 or the section X2 as well. Similarly, when the distance D1 exists in the section X3 or the section X4 as well, an electronic image with the distance DM1 may be acquired. In this case, the position of the sample S and the in-focus position of the image forming optical system 31 coincide during the processing. In this state also, the acquisition step S10 is executed. Descriptions on the other processing are omitted.

As stated above, according to the sample observation method of the second embodiment, it is possible to observe a colorless and transparent sample more clearly in the state of bright-field observation as well.

The sample observation method of the third embodiment includes an amplification step after the subtraction step, and at the amplification step, a signal of an electronic image subjected to the subtraction step is amplified.

Figure 12A:
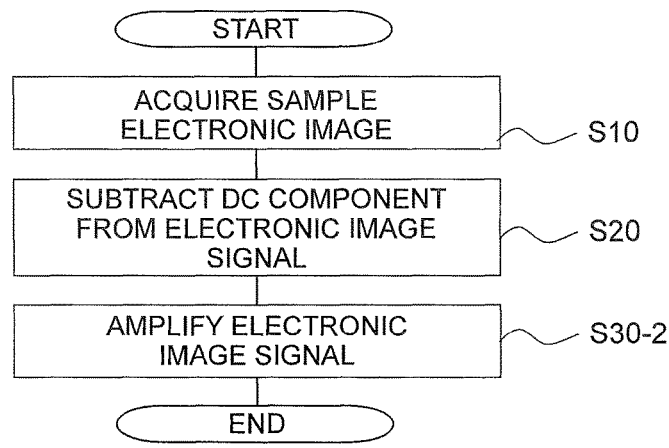
FIG. 12A and FIG. 12B are flowcharts of the sample observation methods as embodiments, where

Referring to FIG. 12A, the sample observation method of the third embodiment is described below. FIG. 12A is a flowchart of the sample observation method of the third embodiment and the sample observation method of the tenth embodiment described later.

As shown in FIG. 12A, the sample observation method of the third embodiment includes an amplification step S30-2 in addition to the acquisition step S10 and the subtraction step S20. Accordingly, in the sample observation method of the third embodiment, it is possible to acquire a clearer electronic image.

As described above, $A_1^2+A_2^2$ represents the DC component of the sample image, i.e., the DC component of a signal of the electronic image. At the subtraction step S20, the value of $A_1^2$ is made smaller, whereby the value of $2A_1A_2 \cos \psi$ is made relatively large with reference to the value of $A_1^2+A_2^2$.

Whereas, in the sample observation method of the third embodiment, the amplification step S30-2 is executed after the acquisition step S10 and the subtraction step S20 end. At the amplification step S30-2, the value of $2A_1A_2 \cos \psi$ is made larger (amplified). By doing so, it is possible to make the value of $2A_1A_2 \cos \psi$ relatively large with reference to the value of $A_1^2+A_2^2$. As a result, it is possible to observe the sample S (image of the sample S) more clearly.

The amplification step S30-2 may be used in the sample observation method of the second embodiment. In this case, the amplification step S30-2 is executed prior to the comparison step S30-1.

As stated above, according to the sample observation method of the third embodiment, it is possible to observe a colorless and transparent sample more clearly in the state of bright-field observation as well.

A sample observation method of the fourth embodiment includes a conversion step of performing Fourier transform of a signal of an electronic image, and an inverse conversion step of performing inverse Fourier transform, and the conversion step is performed prior to the subtraction step, and the inverse conversion step is performed at least after the subtraction step.

Figure 12B:
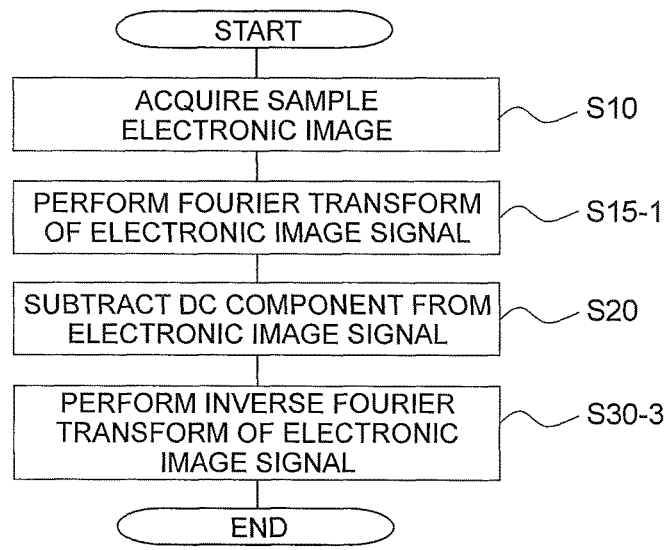
Figure 13A:
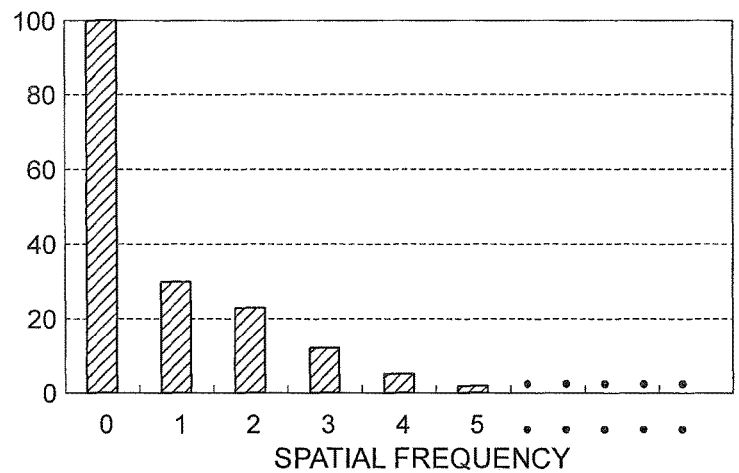
FIG. 13A and FIG. 13B are diagrams showing the magnitude at each spatial frequency, where
Figure 13B:
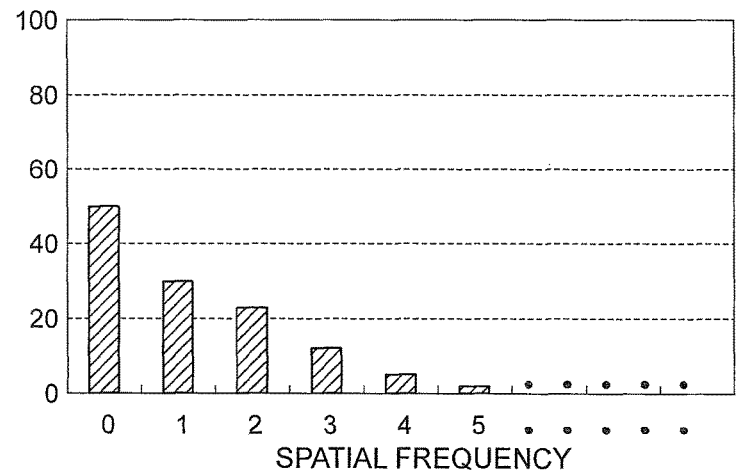

Referring to FIG. 12B, FIG. 13A and FIG. 13B, a sample observation method of the fourth embodiment is described below. FIG. 12B is a flowchart of the sample observation method of the fourth embodiment and the sample observation method of the eleventh embodiment described later. FIG. 13A and FIG. 13B are diagrams showing the magnitude at each spatial frequency, where FIG. 13A is a diagrams showing the state before performing the subtraction step, and FIG. 13B is a diagrams showing the state after performing the subtraction step.

As shown in FIG. 12B, the sample observation method of the fourth embodiment includes a conversion step S15-1 and an inverse conversion step S30-3 in addition to the acquisition step S10 and the subtraction step S20. Accordingly, in the sample observation method of the fourth embodiment, it is possible to acquire clearer electronic images easily.

As described above, at the subtraction step S20, the value of $A_1^2$ is made smaller, whereby the value of $2A_1A_2 \cos \psi$ is made relatively large with reference to the value of $A_1^2+A_2^2$. Here, when the subtraction step S20 is executed at a frequency space, subtraction can be performed effectively.

Referring to FIG. 13A and FIG. 13B, subtraction at the subtraction step S20 is described below. As described above, a sample such as cell includes a structure having various spatial frequencies. Therefore, if brightness of the image of the sample S can be separated for each spatial frequency, subtraction can be performed for each spatial frequency.

Therefore, in the sample observation method of the fourth embodiment, the conversion step S15-1 is executed after the acquisition step S10 ends. At the conversion step S15-1, Fourier transform is performed for a signal of an electronic image. As a result, as shown in FIG. 13A, the magnitude (vertical axis, corresponding to brightness) can be separated for each spatial frequency. In FIG. 13A, the numerical values on the horizontal axis represent spatial frequencies. At the spatial frequency is 0, the magnitude is 100, and at the spatial frequency is 1, the magnitude is 30.

Here, the values of spatial frequency (numerical values on the horizontal axis) correspond to the order of diffracted light. Therefore, the magnitude (numerical value on the vertical axis) at the spatial frequency of 0 corresponds to the brightness of zero-order diffracted light. Similarly, the magnitude at the spatial frequency of 1 corresponds to the brightness of first-order diffracted light. Then, after the conversion step S15-1 ends, the subtraction step S20 is executed. At this subtraction step S20, the magnitude at the spatial frequency of 0 is made smaller. For instance, as shown in FIG. 13B, the magnitude at the spatial frequency of 0 is decreased to half from 100 to 50. This corresponds to that the value of $A_1^2$ is made smaller. By doing so, it is possible to make the brightness of zero-order light smaller.

Next, the inverse conversion step S30-3 is executed. At the inverse conversion step S30-3, inverse Fourier transform is performed. Accordingly, it is possible to acquire a signal of an electronic image. The brightness of zero-order light, i.e., the value of $A_1^2$ is made smaller at the subtraction step S20. Therefore, it is possible to make the value of $2A_1A_2 \cos \psi$ relatively large with reference to the value of $A_1^2+A_2^2$. As a result, it is possible to observe the sample S (image of the sample S) more clearly.

The conversion step S15-1 and the inverse conversion step S30-3 may be used in the sample observation method of the second embodiment and the sample observation method of the third embodiment. In this case, the conversion step S15-1 is executed prior to the subtraction step S20. The inverse conversion step S30-3 is executed after the subtraction step S20.

As stated above, according to the sample observation method of the fourth embodiment, it is possible to observe a colorless and transparent sample more clearly in the state of bright-field observation as well.

A sample observation method of the fifth embodiment includes an acquisition in advance step and a normalization step, and at the acquisition in advance step, an electronic image is acquired without a sample, and at the normalization step, using the electronic image, an electronic image of a sample is normalized, and the normalization step is performed prior to the subtraction step.

Figure 14:
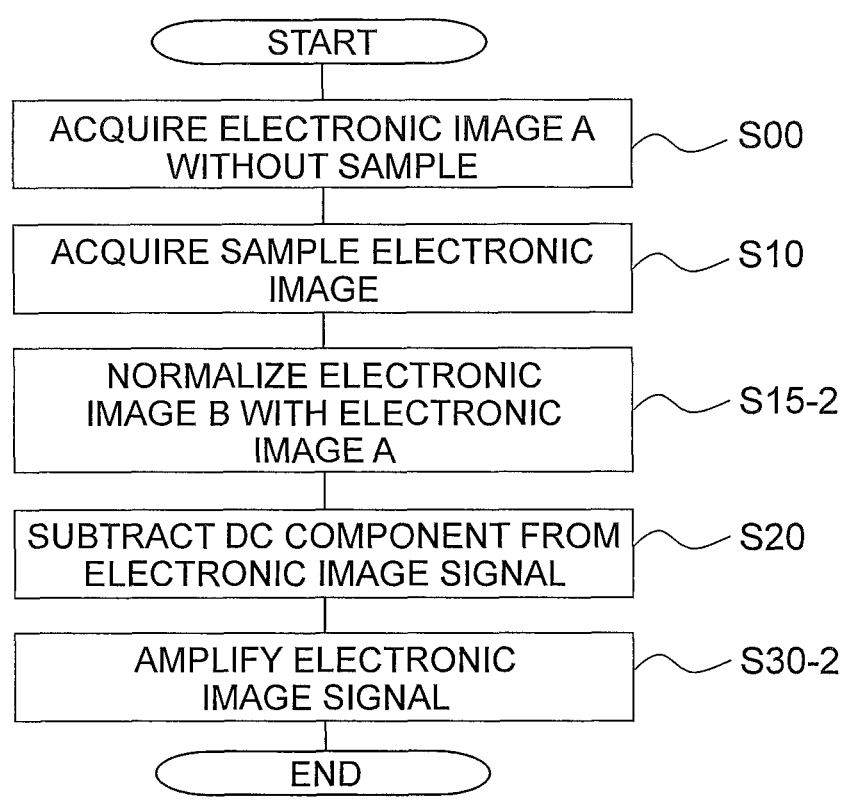
FIG. 14 is a flowchart of the sample observation method of the fifth embodiment and the twelfth embodiment.

Referring to FIG. 14, the sample observation method of the fifth embodiment is described below. FIG. 14 is a flowchart of the sample observation method of the fifth embodiment and the sample observation method of the twelfth embodiment described later.

As shown in FIG. 14, the sample observation method of the fifth embodiment includes an acquisition in advance step S00 and a normalization step S15-2 in addition to the acquisition step S10 and the subtraction step S20. Accordingly, in the sample observation method of the fifth embodiment, it is possible to acquire a clearer electronic image.

In FIG. 14, the amplification step S30-2 is executed after the subtraction step S20, but amplification step S30-2 is not essential.

Brightness of the image of the sample S may be affected by the illumination optical system or by the image forming optical system. For instance, when light passes through the illumination optical system or the image forming optical system, the light after passing therethrough generates unevenness in brightness. In this case, due to such unevenness in brightness of the illumination optical system or the image forming optical system, the unevenness in brightness is also generated in the image of the sample S. Since such unevenness in brightness will degrade the quality of an electronic image, it is preferable to remove such unevenness in brightness.

Therefore, in the sample observation method of the fifth embodiment, the acquisition in advance step S00 is executed prior to the acquisition step S10. At the acquisition in advance step S00, an electronic image A is acquired without a sample S. At this time, the electronic image A will be an image with unevenness in brightness only.

Next, the acquisition step S10 is executed, and thereby an electronic image B of the sample S is acquired. This electronic image B will be an image including unevenness in brightness due to the illumination optical system or the image forming optical system in addition to the image of the sample S. Therefore, the normalization step S15-2 is executed. At this normalization step S15-2, the electronic image B is normalized with the electronic image A. More specifically, the following operation is executed at the normalization step S15-2:

Electronic image $B$/electronic image $A$.

Accordingly, the unevenness in brightness at the electronic image B is canceled with the unevenness in brightness at the electronic image A. Therefore, the electronic image subjected to normalization becomes an image with reduced unevenness in brightness due to the illumination optical system or the image forming optical system.

After the normalization step S15-2 ends, the subtraction step S20 is executed. At the subtraction step S20, the value of $A_1^2$ of an electronic image subjected to normalization is made small, and thereby the value of $2A_1A_2 \cos \psi$ is made relatively large with reference to the value of $A_1^2+A_2^2$. As a result, it is possible to observe the sample S (image of the sample S) more clearly.

The acquisition in advance step S00 and the normalization step S15-2 may be used in any of the sample observation method of the second embodiment to the sample observation method of the fourth embodiment. In this case, the acquisition in advance step S00 is executed prior to the acquisition step S10. The normalization step S15-2 is executed prior to the subtraction step S20.

As stated above, according to the sample observation method of the fifth embodiment, it is possible to observe a colorless and transparent sample more clearly in the state of bright-field observation as well.

In a sample observation method of the sixth embodiment, the position of a sample is changed relative to the in-focus position of the image forming optical system a plurality of times, and at each position of the sample after changing, the acquisition step and the subtraction step are performed, and thereby a plurality of electronic images are generated after the subtraction step, and the plurality of electronic images generated are added.

According to the sample observation method of the sixth embodiment, at the time of generating an electronic image, an image with high contrast at each spatial frequency from a low spatial frequency to a high spatial frequency is used. Therefore, at the electronic image generated, the contrast becomes high at every spatial frequency. As a result, it is possible to observe the sample S (image of the sample S) clearly.

As stated above, according to the sample observation method of the sixth embodiment, it is possible to observe a colorless and transparent sample clearly in the state of bright-field observation as well.

In the sample observation method of the seventh embodiment, before addition, a part with highest contrast in each of a plurality of electronic images is extracted, and the addition is performed using the extracted parts.

According to the sample observation method of the seventh embodiment, at the time of generating an electronic image by addition, a part with highest contrast only for each spatial frequency is used. Therefore, at the electronic image generated, the contrast becomes very high at every spatial frequency. As a result, it is possible to observe the sample S (image of the sample S) can be observed more clearly.

As stated above, according to the sample observation method of the seventh embodiment, it is possible to observe a colorless and transparent sample more clearly in the state of bright-field observation as well.

In the sample observation method of the eighth embodiment, a change of the position of the sample is made while keeping the sign of the amount of wavefront aberration in the first predetermined state same.

As described above, when the amount of wavefront aberration at the first-order diffracted light is $-\lambda/4$, the electronic image will be a dark contrast image. More specifically, in the electronic image, an image of the sample S becomes dark as compared with the background. On the other hand, when the amount of wavefront aberration at the first-order diffracted light is $+\lambda/4$, the electronic image will be a bright contrast image. More specifically, in the electronic image, an image of the sample S becomes bright as compared with the background.

Therefore, it is preferable to use images with the amount of wavefront aberration of the same sign at the time of generating an electronic image by the addition. By doing so, it is possible to make the electronic image generated to be an image based on dark contrast only or an image based on bright contrast only. As a result, it is possible to observe the sample S (image of the sample S) more clearly.

As stated above, according to the sample observation method of the eighth embodiment, it is possible to observe a colorless and transparent sample more clearly in the state of bright-field observation as well.

A sample observation device of the present embodiment is described below. A sample observation device from the first embodiment to the third embodiment includes a light source, an illumination optical system, an image forming optical system, an image-pickup device, and an image processing device, and the illumination optical system is disposed so as to irradiate a sample with illumination light from the light source, and the image forming optical system is disposed so that light from the sample is incident thereon and an optical image of the sample is formed, and the image-pickup device is disposed at the position of the optical image, and the image processing device is configured to implement the sample observation methods from the first embodiment to the eighth embodiment as stated above.

Figure 15:
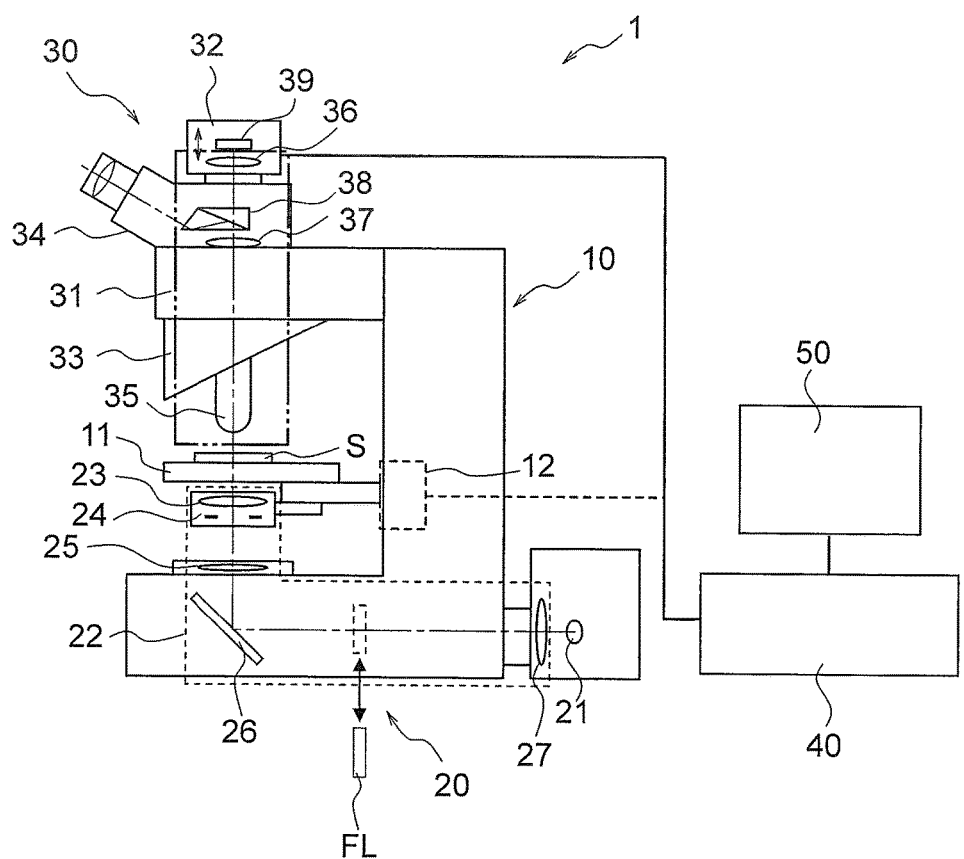
FIG. 15 is a diagram showing a configuration of the sample observation device of the first embodiment.

The configuration of the sample observation device of the first embodiment is shown in FIG. 15. The sample observation device 1 is an observation system based on an upright microscope. The sample observation device 1 includes a main-body part 10, an illumination part 20, an observation part 30, and an image processing device 40. The illumination part 20 and the observation part 30 are attached to the main-body part 10. The main-body part 10 and the image processing device 40 are connected in a wired or wireless manner.

The sample observation device 1 may include a display device 50. The display device 50 may be connected to the image processing device 40 in a wired or wireless manner.

The main-body part 10 includes a stage 11. The stage 11 is a holding member. On this stage 11, a sample S is held. Movement of the sample S is performed using a manipulation knob (not shown) and a focusing knob (not shown) attached to the stage. Through the manipulation of the manipulation knob, the sample S is moved in a plane perpendicular to the optical axis. Through the manipulation of the focusing knob, the sample S is moved along the optical axis.

The illumination part 20 includes a light source 21 and an illumination optical system 22. The illumination optical system 22 includes a condenser lens 23 and an aperture stop 24. As shown in FIG. 15, the illumination optical system 22 may include a lens 25, a mirror 26, and a lens 27. In FIG. 15, the condenser lens 23 and the aperture stop 24 are held at the stage 11. The illumination optical system 22 is disposed in an optical path from the light source 21 to the stage 11.

The observation part 30 includes an image forming optical system 31 and an image-pickup device 32. The observation part 30 may include a revolver 33 and an observation lens barrel 34. The image forming optical system 31 includes a microscope objective lens 35 (hereinafter, referred to as "objective lens 35") and an image-pickup lens 36. As shown in FIG. 15, the image forming optical system 31 may include an image forming lens 37 and a prism 38. The image forming optical system 31 is disposed in an optical path from the stage 11 to the image-pickup device 32. The image-pickup device 32 includes an image-pickup element 39.

In the sample observation device 1, the illumination part 20 is disposed on the side opposed to the observation part 30 across the stage 11. Therefore, in the sample observation device 1, the sample S is illuminated with transmitted illumination.

Illumination light emanates from the light source 21. The illumination light passes through the illumination optical system 22 and reaches the stage 11. The sample S is illuminated with this illumination light. The light from the sample S is collected by the image forming optical system 31, and thereby an image of the sample S (optical image) is formed at the light-collection position. When no prism 38 is disposed in the optical path of the image forming optical system 31, the image-pickup element 39 of the image-pickup device 32 picks up an image of the sample S.

The image of the sample S is converted into an electronic image (digital data) through the image pickup. The electronic image is sent to the image processing device 40. In the image processing device 40, various types of processing are performed. Here, when the sample observation device 1 includes the display device 50, the electronic image is displayed on the display device 50. By viewing the electronic image displayed on the display device 50, an observer can observe the sample S (image of the sample S).

The image-pickup device 32 may include a circuit for automatic gain control. By doing so, it is possible to make the brightness (contrast) of the electronic image picked up constant. The image processing device 40 may include such a circuit for automatic gain control.

It is possible to insert the prism 38 in the optical path of the image forming optical system 31. By doing so, light from the sample S is guided to an eyepiece of the observation lens barrel 34. An observer can observe an optical image of the sample S through the eyepiece.

The procedure to implement a sample observation method of one embodiment is described using the sample observation device 1. In the following description, the sample observation method of the first embodiment is used as an example. A white light source is used as the light source 21.

Firstly, an observer sets the illumination optical system 22 and the image forming optical system 31 in the state of a bright-field observation. Next, the observer places the sample S on the stage 11. Then, the observer moves the sample by eye to the position where the observer thinks that it is displaced from the in-focus position. Accordingly, the position of the sample S and the in-focus position are made to be different in the state of bright-field observation. Next, the image processing device 40 is activated. These steps may be performed in random order.

When the image processing device 40 is activated, the sample observation device is ready to pick up an image of the sample S, and so the acquisition step S10 is executed. By the acquisition step S10 is executed, an electronic image is acquired. The electronic image acquired at the acquisitions step S10 is stored in a temporary storage unit (not shown) in the image processing device 40.

Next, the subtraction step S20 is executed. At the subtraction step S20, by the value of $A_1^2$ is made to be small, the value of $2A_1A_2 \cos \psi$ becomes relatively large with reference to the value of $A_1^2+A_2^2$. The execution result at the subtraction step S20 is displayed on the display device 50, for example.

As stated above, the position of the sample S is set by eye. In this case, since it is highly likely that the position of the sample S and the in-focus position differ greatly, the image of the sample S is defocused greatly. Therefore, even when the image of the sample S is picked up, the observer cannot observe an electronic image thereof on the display device 50.

Therefore, the observer manipulates the focusing knob to move the sample S toward the in-focus position. If the sample S is far away from the objective lens 35, the observer may move the stage 11 so as to move the sample S toward the objective lens 35. On the other hand, when the sample S is very close to the objective lens 35, the observer may move the stage 11 so as to move the sample S away the objective lens 35.

While the sample S is moved, image-pickup is continuously performed. Therefore, the acquisition step S10 and the subtraction step S20 also are continuously executed. Then, the observer can move the sample S along the optical axis while viewing an electronic image on the display device 50, and stops to move the sample S when an electronic image with good contrast can be acquired. As a result, it is possible to observe the sample S (image of the sample S) clearly.

The main-body part 10 may include a motor 12. In FIG. 15, the motor 12 is connected to the stage 11. It is possible to move the sample S by moving the stage 11 along the optical axis using the motor 12.

As stated above, according to the sample observation device of the first embodiment, it is possible to observe a colorless and transparent sample clearly in the state of bright-field observation as well.

Figure 16:
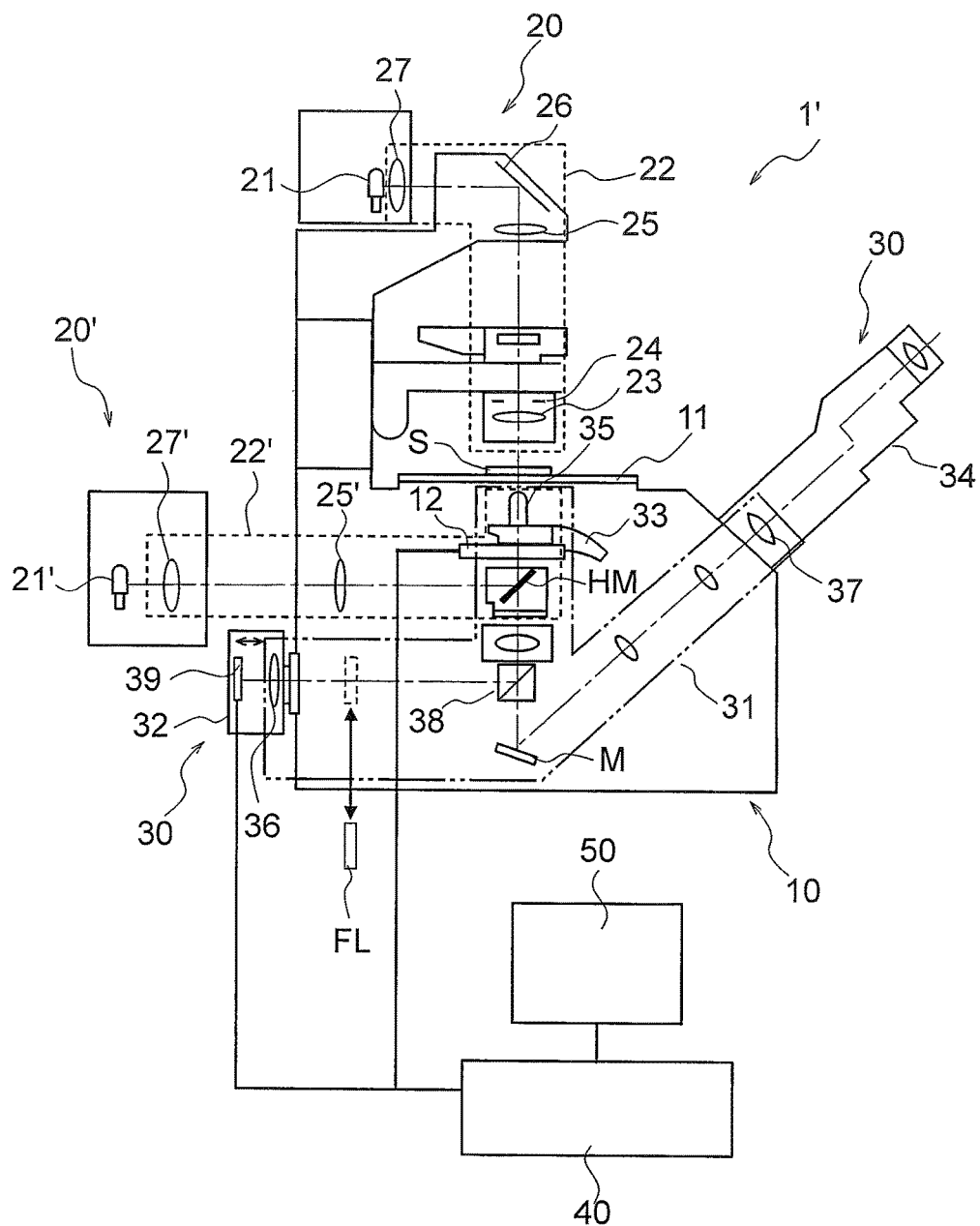
FIG. 16 is a diagram showing a configuration of the sample observation device of the second embodiment.

The configuration of the sample observation device of the second embodiment is shown in FIG. 16. The sample observation device 1' is an observation system based on an inverted microscope. The same reference numerals are assigned to the same components as those of the sample observation device 1, and their descriptions are omitted.

Similarly to the sample observation device 1, in the of the sample observation device 1', illumination part 20 is disposed on the side opposed to the observation part 30 across the stage 11. Therefore, in the sample observation device 1' as well, the sample S is illuminated with transmitted illumination. However, the sample observation device 1' then includes an illumination part 20' in addition to the illumination part 20. The illumination part 20' is disposed on the same side as the observation part 30. Therefore, in the sample observation device 1', it is possible to illuminate the sample S by epi-illumination using the illumination part 20'.

The illumination part 20' includes a light source 21' and an illumination optical system 22'. The illumination optical system 22' includes a condenser lens and an aperture stop. Here, in the illumination optical system 22', illumination is performed through the objective lens 35. Therefore, the objective lens 35 corresponds to a condenser lens. The aperture stop is not shown in the drawing. As shown in FIG. 16, the illumination optical system 22' may include a lens 25', a half mirror HM and a lens 27'. The illumination optical system 22' is disposed in an optical path from the light source 21' to the stage 11. The half mirror HM and the objective lens 35 make up the illumination optical system 22' as well as the image forming optical system 31.

When the prism 38 is disposed in the optical path of the image forming optical system 31, the image-pickup element 39 of the image-pickup device 32 picks up an image of the sample S. When the prism 38 is moved out of the optical path of the image forming optical system 31, light of the sample S can be guided to an eyepiece of the observation lens barrel 34. In this case, light of the sample S is reflected toward the observation lens barrel 34 by the mirror M.

In the sample observation device 1', the motor 12 is connected to the revolver 33. Therefore, in the sample observation device 1', the revolver 33 is moved along the optical axis by the motor 12. As the revolver 33 moves along the optical axis, the objective lens 35 (image forming optical system 31) moves along the optical axis. Accordingly, it is possible to make in a state where the position of the sample S and the in-focus position are different.

In the sample observation device 1', it is possible to illuminate the sample S by transmitted illumination or vertical illumination. The vertical illumination is described below. In the vertical illumination, illumination light emanates from the light source 21'. The illumination light passes through the illumination optical system 22' and reaches the stage 11. The sample S is illuminated with this illumination light. The light from the sample S is collected by the image forming optical system. 31, and thereby an image of the sample S (optical image) is formed at the light-collection position. When the prism 38 is disposed in the optical path of the image forming optical system 31, the image-pickup element 39 of the image-pickup device 32 picks up an image of the sample S.

The image of the sample S is converted into an electronic image (digital data) through the image pickup. The electronic image is sent to the image processing device 40. In the image processing device 40, various types of processing are performed. Here, when the sample observation device 1' includes the display device 50, the electronic image is displayed on the display device 50. By viewing the electronic image displayed on the display device 50, an observer can observe the sample S (image of the sample S) clearly.

The procedure to implement a sample observation method of one embodiment is described using the sample observation device 1'. In the following description, the sample observation method of the second embodiment is used as an example. A white light source is used as the light source 21'.

Firstly, an observer sets the illumination optical system 22' and the image forming optical system 31 in the state of a bright-field observation. Then the observer places the sample S on the stage 11. Next the image processing device 40 is activated. These steps may be performed in random order.

The observer inputs information of observation starting to the image processing device 40. Here, information of displacement from the in-focus position is assumed to be stored in the image processing device 40 beforehand. The image processing device 40 calculates the amount of movement based on the current position of the revolver 33 (microscope objective lens 35) and the displacement from the in-focus position. Based on the calculation result, the image processing device 40 transmits a driving signal to the motor 12. Based on the signal transmitted, the motor 12 moves the revolver 33 so that the sample S is displaced from the in-focus position. In this way, it is possible to make in a state where the position of the sample S and the in-focus position are different.

When the state of bright-field observation and the state where the position of the sample S and the in-focus position are different are achieved, then the acquisition step S10 (first time) is executed. Then an electronic image is acquired. The electronic image acquired is stored in a temporary storage unit (not illustrated) in the image processing device 40. Next, the subtraction step S20 is executed. After the subtraction step S20 ends, the electronic image is stored in a storage unit 1 (not shown) in the image processing device 40. The electronic image stored in the storage unit 1 is displayed on the display device 50, for example.

After the subtraction step S20 ends, the image processing device 40 transmits a driving signal to the motor 12. The driving signal at this time is to widen the distance D (distance between the sample S and the objective lens 35) by a predetermined amount. The motor 12 moves the revolver 33 in accordance with the signal so that the objective lens 35 is moved away from the stage 11.

When the objective lens 35 moves by the predetermined amount, the acquisition step S10 (second time) and the subtraction step S20 are executed. After the subtraction step S20 ends, the electronic image is stored in a storage unit 2 (not shown) in the image processing device 40.

Next, comparison of contrast is made between the electronic image in the storage unit 1 and the electronic image in the storage unit 2. When the determination result is YES, setting is made to narrow the distance D. On the other hand, when the determination result is NO, setting is made to widen the distance D, and the electronic image stored in the storage unit 2 is stored in the storage unit 1.

When setting on the distance D ends, the acquisition step S10 (third time) and the subtraction step S20 are executed. Next, comparison of contrast is made between the electronic image in the storage unit 1 and the electronic image in the storage unit 2. The procedure from the acquisition step S10 to the comparison step 30-1 is repeated until a predetermined condition is satisfied.

When the predetermined condition is satisfied, all of the processing ends. Accordingly, an electronic image with sufficiently high contrast is acquired automatically. As a result, it is possible to observe the sample S (image of the sample S) more clearly.

As stated above, according to the sample observation device of the second embodiment, it is possible to observe a colorless and transparent sample more clearly in the state of bright-field observation as well.

Figure 17A:
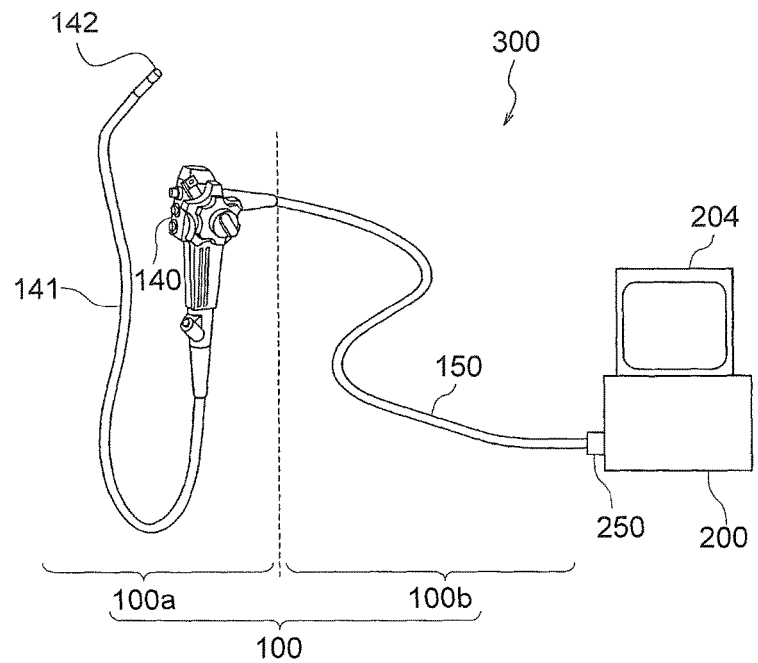
FIG. 17A and FIG. 17B are diagrams showing a configuration of a sample observation device of the third embodiment, where
Figure 17B:
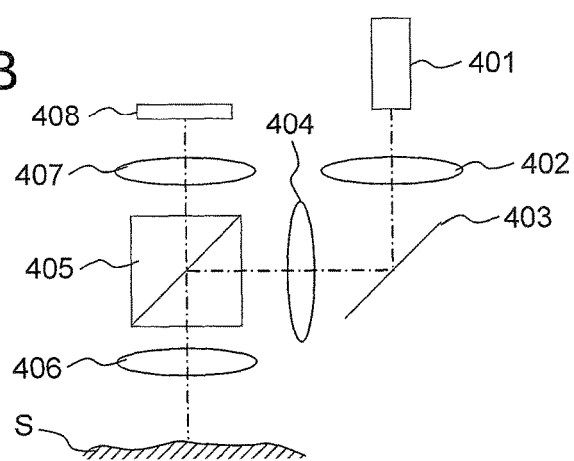

The configuration of a sample observation device of the third embodiment is shown in FIG. 17A and FIG. 17B. FIG. 17A is a diagram showing the schematic configuration of the observation device, and FIG. 17B is a diagram showing the configuration of the optical system.

A sample observation device 300 is an observation system based on an electronic endoscope. The sample observation device 300 includes an electronic endoscope 100 and an image processing device 200. The electronic endoscope 100 includes a scope part 100a and a connection cord part 100b. The image processing device 200 is connected to a display unit 204.

The scope part 100a is roughly divided into a manipulation part 140 and an insertion part 141. The insertion part 141 is long and thin and so is able to be inserted into a body cavity of a patient. The insertion part 141 is made of a member having flexibility. An observer can perform various manipulations using an angle knob, for example, provided at the manipulation part 140.

Moreover, from the manipulation part 140, the connection cord part 100b is extended. The connection cord part 100b includes a universal cord 150. The universal cord 150 is connected to the image processing device 200 via a connector 250.

The universal cord 150 is used to exchange various types of signals. A power-supply voltage signal, a CCD driving signal and the like are included in the various types of signals. These signals are transmitted from a power-supply device or a video processor to the scope part 100a. A video signal is included in the various types of signals. This signal is transmitted from the scope part 100a to a video processor. The video processor in the image processing device 200 can be connected to peripheral devices such as a VTR deck and a video printer, which are not shown. The video processor performs signal processing of a video signal from the scope part 100a. Based on the video signal, an endoscopic image is displayed on a display screen of a display unit 204.

In a forward end part 142 of the insertion part 141, an optical system is disposed. Here, the electronic endoscope 100 is a magnifying endoscope. Therefore, the optical system is configured to form a magnified image of the sample S. Tissues in body are object to be observed in an endoscope. In the following descriptions, the tissues in body are assumed to be included in the sample S as well.

An illumination part includes a light source and an illumination optical system. Light from the light source emanates from an optical fiber 401. The illumination optical system includes a lens 402, a mirror 403, a lens 404, a half prism 405, and an objective lens 406. An observation part includes an image forming optical system and an image-pickup device. The image forming optical system includes the objective lens 406, the half prism 405, and an image forming lens 407. The image-pickup device includes an image-pickup element 408. In this optical system, a sample S is illuminated with epi-illumination.

The procedure to implement a sample observation method of one embodiment is described using the sample observation device 300. In the following description, the sample observation method of the third embodiment is used as an example. A white light source is used as the light source.

Firstly, an observer sets the illumination optical system and the image forming optical system in the state of a bright-field observation. Then the observer moves the insertion part 141 by eye to the position where the observer thinks that it is displaced from the in-focus position. Next, the image processing device 200 is activated. These processing steps may be performed in random order.

When the image processing device 200 is activated, the sample observation device is ready to pick up an image of the sample S, and so the acquisition step S10 is executed. By the acquisition step S10 is executed, an electronic image is acquired. The electronic image acquired at the acquisitions step S10 is stored in a temporary storage unit (not shown) in the image processing device 200.

Next, the subtraction step S20 is executed. At the subtraction step S20, by the value of $A_1^2$ is made to be small, the value of $2A_1A_2 \cos \psi$ becomes relatively large with reference to the value of $A_1^2+A_2^2$.

After the subtraction step S20 ends, the amplification step S30-2 is executed. At the amplification step S30-2, the value of $2A_1A_2 \cos \psi$ is made larger (amplified). Accordingly, the value of $2A_1A_2 \cos \psi$ becomes relatively larger with reference to the value of $A_1^2+A_2^2$. The execution result at the amplification step S30-2 is displayed on the display unit 204, for example.

While the insertion part 141 is moved, image-pickup is continuously performed. Therefore, the acquisition step S10, the subtraction step S20 and the amplification step S30-2 also are continuously executed. Then the observer can move the insertion part 141 while viewing an electronic image on the display unit 204, and stops to move the insertion part 141 when an electronic image with good contrast can be acquired. As a result, it is possible to observe the sample S (image of the sample S) clearly.

At least one of the objective lens 406, the image-pickup lens 407 and the image-pickup element 408 may be moved along the optical axis. They may be moved using a micro-actuator (not illustrated) or a voice coil motor (not illustrated). By, doing so, it is possible to adjust the displacement $\Delta Z$ finely. Therefore, the movement of the insertion part 141 can be stopped when an electronic image with certain contrast is acquired.

As stated above, according to the sample observation device of the third embodiment, it is possible to observe a colorless and transparent sample more clearly in the state of bright-field observation as well.

Moreover, in each sample observation device of the embodiments stated above, it is preferable that the following conditional expression (1) is satisfied:

$$0.01 < NA_{ill}/NA_{ob} < 1 \tag{1}$$

where, $NA_{ill}$ denotes a numerical aperture of the illumination optical system on the sample side, and $NA_{ob}$ denotes a numerical aperture of the image forming optical system on the sample side.

By satisfying of the conditional expression (1), it is possible to observe a colorless and transparent sample more clearly in the state of bright-field observation as well.

When falling below a lower limit value of the conditional expression (1), the numerical aperture of the illumination optical system on the sample side is too small. In this case, insufficiency of light amount of the illumination light becomes large or unevenness of the illumination becomes large. Moreover, on the electronic image, dirt or foreign particles on the cover glass becomes conspicuous.

When exceeding an upper limit value of the conditional expression (1), the numerical aperture of the illumination optical system on the sample side is too large. In this case, illumination light obliquely incident with respect to the optical axis increases. Therefore, it becomes difficult to acquire an electronic image with good contrast. This point is described with reference to FIG. 18A, FIG. 18B, and FIG. 18C.

Figure 18A:
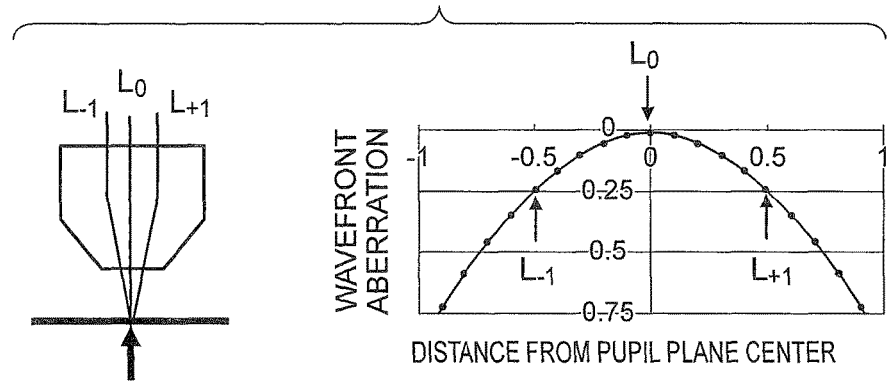
FIG. 18A, FIG. 18B, and FIG. 18C are diagrams showing a relationship between the incident direction of illumination light and the diffraction direction of diffracted light, and the wavefront aberration, where
Figure 18B:
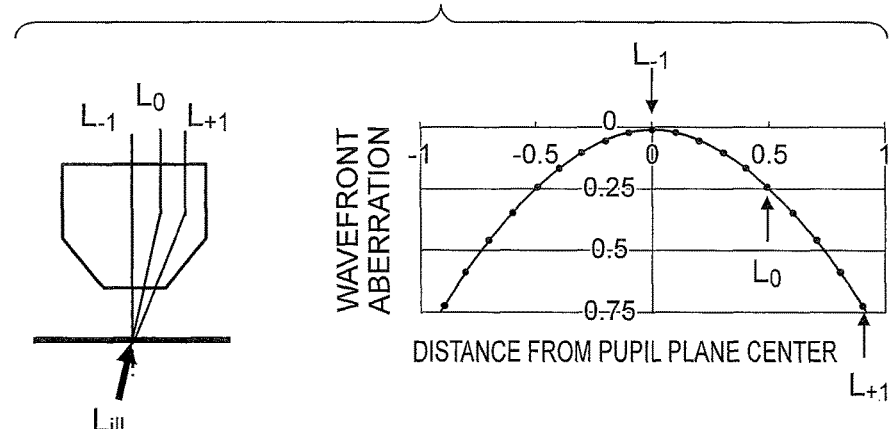
Figure 18C:
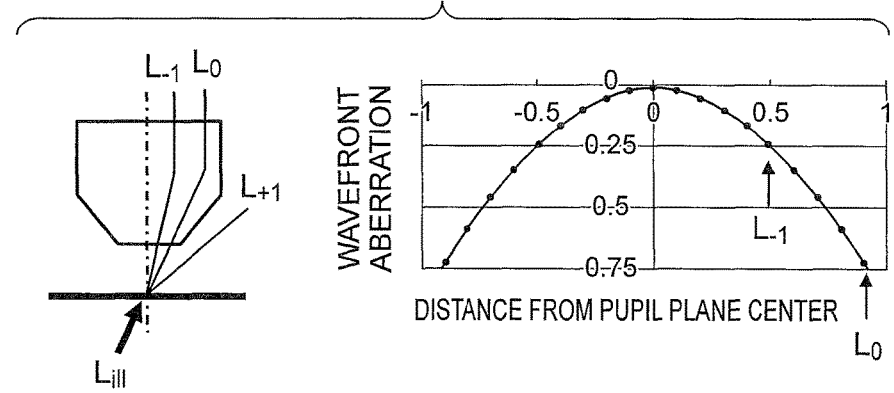

FIG. 18A, FIG. 18B, and FIG. 18C are diagrams showing a relationship between the incident direction of illumination light and the diffraction direction of diffracted light, and the wavefront aberration, where FIG. 18A is a diagram showing the case where the illumination light is incident in parallel with the optical axis, FIG. 18B is a diagram showing the case where the angle between the incident direction of the illumination light and the optical axis is small, and FIG. 18C is a diagram showing the case where the angle between the incident direction of the illumination light and the optical axis is large.

Diffracted light generated from the sample S depends on an incident direction of the illumination light on the sample S. As shown in FIG. 18A, when an incident direction of a illumination light $L_{ill}$ is parallel to the optical axis, zero-order diffracted light $L_0$ travels along the optical axis and reaches the pupil position. On the other hand, +1 for first order diffracted light $L_{+1}$ is incident on the image forming optical system at the angle +θ with respect to the optical axis and reaches the pupil position. −1 for first order diffracted light $L_{-1}$ is incident on the image forming optical system at the angle −θ with respect to the optical axis and reaches the pupil position.

As described above, when the sample S is displaced from the in-focus position, wavefront aberration occurs. This wavefront aberration occurs symmetrically with respect to the center of the pupil plane. Therefore, in the case of FIG. 18A, the amount of wavefront aberration added to zero-order diffracted light $L_0$ is 0, but the wavefront aberration of a predetermined amount will be added to the +1 for first order diffracted light $L_{+1}$ and the −1 for first order diffracted light $L_{-1}$.

Here, a diffraction directions of the +1 for first order diffracted light $L_{+1}$ and the −1 for first order diffracted light $L_{-1}$ are symmetrical across the optical axis, and the wavefront aberration also occurs symmetrically with respect to the center (optical axis) of the pupil plane. Therefore, the amount of wavefront aberration added to the +1 for first order diffracted light $L_{+1}$ and the amount of wavefront aberration added to the −1 for first order diffracted light $L_{-1}$ become same.

In FIG. 18A, since the zero-order diffracted light $L_0$ travels along the optical axis, the amount of wavefront aberration added to zero-order diffracted light $L_0$ is 0. To both of the +1 for first order diffracted light $L_{+1}$ and the −1 for first order diffracted light $L_{-1}$, the amount of wavefront aberration of −λ/4 is added.

As a result, a change in phase of the zero-order diffracted light $L_0$ is not generated. On the other hand, in the phase of the +1 for first order diffracted light $L_{+1}$ and the phase of the −1 for first order diffracted light $L_{-1}$, since π/2 is added with respect to the original delay of π/2, the delay will be π in total. Then, the phase difference is expressed by $\psi=0-(-\pi)=\pi$. In this case, since $2A_1A_2 \cos \psi \neq 0$, phase information can be obtained in the form of contrast information. Moreover, the contrast acquired is so-called dark contrast. The same as the +1 for first order diffracted light $L_{+1}$ applies to the −1 for first order diffracted light $L_{-1}$.

Next, as shown in FIG. 18B, when the angle between the incident direction of the illumination light $L_{ill}$ and the optical axis is small (the angle is θ), the zero-order diffracted light $L_0$ travels in the same direction as the incident direction of the illumination light $L_{ill}$. Therefore, the zero-order diffracted light $L_0$ is incident on the image forming optical system at the angle of +θ with respect to the optical axis, and reaches the pupil position. On the other hand, +1 for first order diffracted light $L_{+1}$ is diffracted outside (direction away from the optical axis) of a predetermined direction. Therefore, +1 for first order diffracted light $L_{+1}$ is incident on the image forming optical system at the angle of +2θ with respect to the optical axis, and reaches the pupil position. Moreover, although −1 for first order diffracted light $L_{-1}$ also is diffracted, the −1 for first order diffracted light $L_{-1}$ travels along the optical axis and reaches the pupil position.

Here, although the diffraction direction of the +1 for first order diffracted light $L_{+1}$ and the diffraction direction of the −1 for first order diffracted light $L_{-1}$ are asymmetrical across the optical axis, the wavefront aberration occurs symmetrically with respect to the center (optical axis) of the pupil plane. Therefore, the amount of wavefront aberration added to the zero-order diffracted light $L_0$, the amount of wavefront aberration added to the +1 for first order diffracted light $L_{+1}$, and the amount of wavefront aberration added to the −1 for first order diffracted light $L_{-1}$ are mutually different.

In FIG. 18B, the amount of wavefront aberration of −λ/4 is added to the zero-order diffracted light $L_0$, and the amount of wavefront aberration of −3λ/4 is added to the +1 for first order diffracted light $L_{+1}$. Meanwhile, since the −1 for first order diffracted light $L_{-1}$ travels along the optical axis, the amount of wavefront aberration added to the −1 for first order diffracted light $L_{-1}$ becomes 0.

As a result, the phase of the zero-order diffracted light $L_0$ is delayed by π/2. On the other hand, in the phase of the +1 for first order diffracted light $L_{+1}$, since 3π/2 is added with respect to the original delay of π/2, the delay will be 2π in total. Then, the phase difference is expressed by $\psi=-\pi/2-(-2\pi)=3\pi/2$. In this case, since $2A_1A_2 \cos \psi=0$, phase information cannot be obtained in the form of contrast information. On the other hand, since the amount of wavefront aberration added to the −1 for first order diffracted light $L_{-1}$ is 0, the phase of the −1 for first order diffracted light $L_{-1}$ is simply π/2 that is original delay. Then, the phase difference is expressed by $\psi=-\lambda/2-(-\lambda/2)=0$. In this case, since $2A_1A_2 \cos \psi \neq 0$, phase information can be obtained in the form of contrast information. The contrast acquired is so-called bright contrast.

Next, as shown in FIG. 18C, when the angle between the incident direction of the illumination light $L_{ill}$ and the optical axis is large (the angle is 2θ), the zero-order diffracted light $L_0$ travels in the same direction as the incident direction of the illumination light $L_{ill}$. Therefore, the zero-order diffracted light $L_0$ is incident on the image forming optical system at the angle of +2θ with respect to the optical axis, and reaches the pupil position. On the other hand, +1 for first order diffracted light $L_{+1}$ is diffracted outside of an effective aperture of the image forming optical system. That is, the +1 for first order diffracted light $L_{+1}$ does not reach the pupil position. Moreover, the −1 for first order diffracted light $L_{-1}$ is incident on the image forming optical system at the angle of +θ with respect to the optical axis, and reaches the pupil position.

Here, although the diffraction direction of the +1 for first order diffracted light $L_{+1}$ and the diffraction direction of the −1 for first order diffracted light $L_{-1}$ are asymmetrical across the optical axis, the wavefront aberration occurs symmetrically with respect to the center (optical axis) of the pupil plane. Therefore, the amount of wavefront aberration added to the zero-order diffracted light $L_0$ and the amount of wavefront aberration added to the −1 for first order diffracted light $L_{-1}$ are mutually different.

In FIG. 18C, the amount of wavefront aberration of $-3\lambda/4$ is added to the zero-order diffracted light $L_0$, and the amount of wavefront aberration of $-\lambda/4$ is added to the $-1$ for first order diffracted light $L_{-1}$.

As a result, the phase of the zero-order diffracted light $L_0$ is delayed by $3\pi/2$. On the other hand, in the phase of the $-1$ for first order diffracted light $L_{-1}$, since $\pi/2$ is added with respect to the original delay of $\pi/2$, the delay will be $\pi$ in total. Then, the phase difference is expressed by $\psi=-3\pi/2-(-\pi)=-\pi/2$. In this case, since $2A_1 A_2 \cos \psi=0$, phase information cannot be obtained in the form of contrast information.

When the numerical aperture of the illumination optical system on the sample side is small, the incident direction of the illumination light $L_{ill}$ is parallel to the optical axis. More specifically, it becomes the state shown in FIG. 18A. Therefore, an image of a point on the optical axis can be observed in a so-called dark contrast. Meanwhile, as the numerical aperture of the illumination optical system on the sample side increases, illumination light $L_{ill}$ whose incident direction intersects with the optical axis is applied as shown in FIG. 18B and FIG. 18C.

In this case, an image of a point on the optical axis becomes an image that an image of bright contrast is added to an image of dark contrast. Therefore, the contrast of the image decreases. As just described, as the numerical aperture of the illumination optical system on the sample side increases, light leading to a decrease in contrast increases unfortunately.

It is preferable that the following conditional expression (1') is satisfied instead of the conditional expression (1):

$$0.02 < NA_{ill}/NA_{ob} < 0.9 \qquad (1').$$

Further, it is more preferable that the following conditional expression (1") is satisfied instead of the conditional expression (1):

$$0.03 < NA_{ill}/NA_{ob} < 0.8 \qquad (1").$$

Moreover, in each sample observation device of the embodiments stated above, it is preferable that the following conditional expression (2) is satisfied:

$$0.1\ \mu m < \Delta Z \times NA_{ob}^2 < 30\ \mu m \qquad (2)$$

where $\Delta Z$ denotes a difference in position between the in-focus position of the image forming optical system and the sample, and $NA_{ob}$ denotes the numerical aperture of the image forming optical system on the sample side.

By satisfying of the conditional expression (2), it is possible to observe a colorless and transparent sample more clearly in the state of bright-field observation as well.

When falling below a lower limit of the conditional expression (2), a difference between the in-focus position of the image forming optical system and the position of the sample is too small. In this case, the amount of wavefront aberration added to the diffracted light is small. Especially, the amount of wavefront aberration added to the first-order diffracted light becomes smaller than $\lambda/4$. Moreover, optical image is defocused greatly. As a result, it becomes difficult to acquire an electronic image with good contrast.

When exceeding an upper limit of the conditional expression (2), the difference between the in-focus position of the image forming optical system and the position of the sample is too large. In this case, the amount of wavefront aberration added to the diffracted light is large. Especially, the amount of wavefront aberration added to the first-order diffracted light becomes larger than $\lambda/4$. Moreover, an optical image is defocused greatly. As a result, it becomes difficult to acquire an electronic image with high resolution.

It is preferable that the following conditional expression (2') is satisfied instead of the conditional expression (2):

$$0.2\ \mu m < \Delta Z \times NA_{ob}^2 < 25\ \mu m \qquad (2').$$

Further, it is more preferable that the following conditional expression (2") is satisfied instead of the conditional expression (2):

$$0.3\ \mu m < \Delta Z \times NA_{ob}^2 < 20\ \mu m \qquad (2").$$

Moreover, in each sample observation device of the embodiments as stated above, it is preferable that the following conditional expression (3) is satisfied:

$$0.05\ \mu m < \Delta Z \times NA_{ill} < 10\ \mu m \qquad (3)$$

where $\Delta Z$ denotes the difference in position between the in-focus position of the image forming optical system and the sample, and $NA_{ill}$ denotes the numerical aperture of the illumination optical system on the sample side.

By satisfying of the conditional expression (3), it is possible to observe a colorless and transparent sample more clearly in the state of bright-field observation as well.

When falling below a lower limit of the conditional expression (3), a difference between the in-focus position of the image forming optical system and the position of the sample is too small. In this case, the amount of wavefront aberration added to the diffracted light is small. Especially, the amount of wavefront aberration added to the first-order diffracted light becomes smaller than $\lambda/4$. Moreover, optical image is defocused greatly. As a result, it becomes difficult to acquire an electronic image with good contrast.

When exceeding an upper limit of the conditional expression (3), the difference between the in-focus position of the image forming optical system and the position of the sample is too large. In this case, the amount of wavefront aberration added to the diffracted light is large. Especially, the amount of wavefront aberration added to the first-order diffracted light becomes larger than $\lambda/4$. Moreover, an optical image is defocused greatly. As a result, it becomes difficult to acquire an electronic image of high resolution. Further, when exceeding the upper limit of the conditional expression (3), the numerical aperture of the illumination optical system on the sample side is too large. In this case, illumination light obliquely incident with respect to the optical axis increases. Therefore, it becomes difficult to acquire an electronic image with good contrast.

It is preferable that the following conditional expression (3') is satisfied instead of the conditional expression (3):

$$0.1\ \mu m < \Delta Z \times NA_{ill} < 8\ \mu m \qquad (3').$$

Further, it is more preferable that the following conditional expression (3") is satisfied instead of the conditional expression (3):

$$0.2\ \mu m < \Delta Z \times NA_{ill} < 6\ \mu m \qquad (3").$$

Moreover, in each sample observation device of the embodiments as stated above, it is preferable that the illumination optical system includes a condenser lens and an aperture stop.

By doing so, it is possible to set the numerical aperture of the illumination optical system on the sample side at an appropriate value in accordance with the optical performance of the objective lens. Therefore, it is possible to acquire an electronic image with good contrast.

Moreover, in each sample observation device of the embodiments as stated above, it is preferable that the illumination optical system is a Kohler illumination optical system.

By doing so, it is possible to illuminate a sample without unevenness. Therefore, it is possible to make the processing (image processing) in the sample observation methods as stated above simple.

Moreover, in each sample observation device of the embodiments as stated above, it is preferable that the illumination optical system is a telecentric optical system.

By doing so, it is possible to acquire an electronic image with good contrast at the entire observation area.

Figure 19:
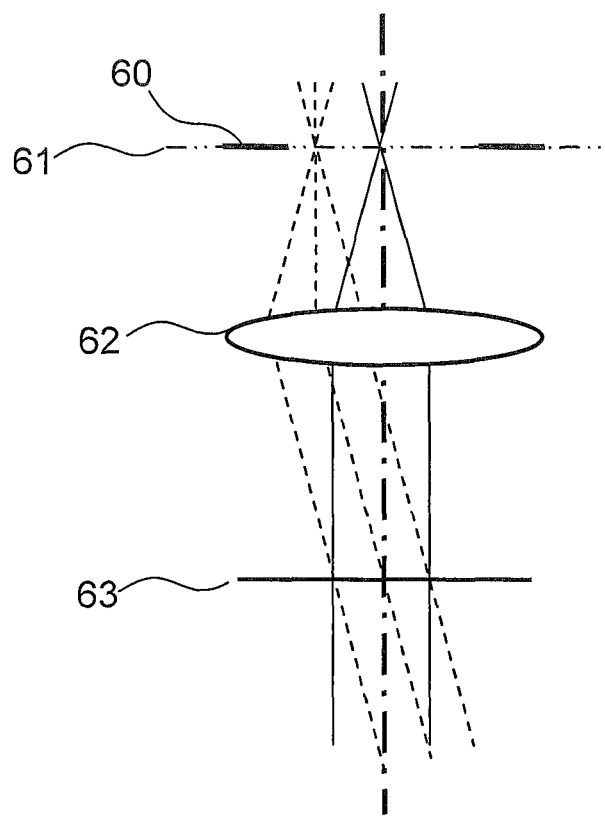
FIG. 19 is a diagram showing a case where the illumination optical system is a telecentric optical system.

FIG. 19 is a diagram showing a case where the illumination optical system is a telecentric optical system. The illumination optical system includes a condenser lens 62 and an aperture stop 60. At a front focal plane 61 of the condenser lens 62, the aperture stop 60 is disposed. Therefore, axial light flux (line indicated with the solid line) emanated from the center of the aperture stop 60 is converted into parallel light flux by the condenser lens 62, and reaches a position 63 of the sample. Meanwhile, off-axis light flux (line indicated with broke lines) emanated from the periphery of the aperture stop 60 also is converted into parallel light flux by the condenser lens 62, and reaches the position 63 of the sample. Here, since the illumination optical system is a telecentric optical system, the off-axis light flux is incident on the condenser lens so that its principal ray is parallel to the optical axis.

As shown in FIG. 19, the light flux passing through the center of the aperture stop 60 is converted into parallel to the optical axis and reaches the position of the sample. The sample is illuminated with light flux that is parallel to the optical axis, and then zero-order diffracted light and first-order diffracted light are generated from the sample. Between them, zero-order diffracted light travels in parallel with the optical axis. On the other hand, +1 for first order diffracted light and −1 for first order diffracted light travel in the direction away from the optical axis.

Moreover, the +1 for first order diffracted light and the −1 for first order diffracted light travel while being symmetrical with respect to the optical axis. In this case, the amount of wavefront aberration added to the +1 for first order diffracted light and the amount of wavefront aberration added to the −1 for first order diffracted light become both same. When the zero-order diffracted light and the +1 for first order diffracted light are mutually weakened, then the zero-order diffracted light and the −1 for first order diffracted light also are mutually weakened. Conversely, when the zero-order diffracted light and the +1 for first order diffracted light are mutually strengthened, then the zero-order diffracted light and the −1 for first order diffracted light also are mutually strengthened. Therefore, it is possible to acquire an electronic image with good contrast at the entire observation area.

Moreover, it is preferable that each sample observation device of the embodiments as stated above includes wavelength selection means. Moreover, in each sample observation devices of the embodiments as stated above, it is preferable that illumination light is monochromatic light.

By doing so, it is possible to acquire an electronic image with good contrast. Especially even when the image forming optical system which has a large amount of axial chromatic aberration is used, it is possible to acquire an electronic image with good contrast.

It is preferable that aberrations of the image forming optical system are small. In the sample observation devices (sample observation methods) of the embodiments, it is desirable that axial chromatic aberration is favorably corrected. When an amount of axial chromatic aberration generated is large, the amount of generation of wavefront aberration differs with the wavelength. For instance, when the sample is illuminated with white light, the amount of wavefront aberration added to the first-order diffracted light may be 1/4λ for light at a certain wavelength and may be −1/4λ for light at another wavelength.

In this case, an image has dark contrast for light at a certain wavelength and has bright contrast for light at another wavelength. Therefore, considering the white light as a whole, it becomes difficult to acquire an electronic image with good contrast.

Therefore, when the sample observation device includes wavelength selection means, it is possible to suppress the decrease of contrast. By the sample observation device including wavelength selection means, it is possible to eliminate variations in the amount of generation of wavefront aberration due to wavelength. For this reason, it is possible to acquire an electronic image with good contrast. Especially when the image forming optical system which has large axial chromatic aberration is used, it is possible to acquire an electronic image with good contrast by including wavelength selection means. The same applies to the case where the illumination light is monochromatic light.

As stated above, in the state of bright-field observation of the present embodiment, when the sample is colorless and transparent in these embodiments, the illumination light and the image forming light may have light of a common wavelength. Therefore, in the sample observation device 1 (FIG. 15), an arrangement is made such that an optical filter FL (wavelength selection means) can be disposed in the optical path of the illumination part 20. Moreover, in the sample observation device 1' (FIG. 16), an arrangement is made such that an optical filter FL and an optical filter FL' (not shown) can be disposed alternately in the optical path of the image forming optical system 31. Although no optical filter FL is shown, in the sample observation device 300 (FIG. 17A, FIG. 17B), it is possible to have a similar configuration to those of the sample observation device 1 and the sample observation device 1'.

The optical filter FL may be movable. Moreover, number of the optical filter FL is not limited to one. A plurality of optical filters FL may be prepared, each having different spectral transmission property, and one or a plurality of them may be disposed in the optical path.

The optical filter FL may be disposed at any one of the illumination optical system and the image forming optical system, or at both of them. The optical filter FL may be disposed at the image-pickup device. When the image-pickup device includes any optical filter, then this optical filter may be used.

When the optical filter FL has a property of transmitting light of long wavelengths, by using such an optical filter FL it is possible to reduce damages on cells. On the other hand, when the optical filter FL has a property of transmitting light of short wavelengths, by using such an optical filter FL it is possible to acquire an electronic image with high resolution.

The light source itself may be used a light source which emit light of a narrow wavelength band. By doing so, it is possible to eliminate the necessity to dispose an optical filter in the optical path of the optical system. Moreover, a plurality of light sources may be used.

Moreover, in each sample observation devices of the embodiments as stated above, it is preferable that the image forming optical system is a telecentric optical system.

By doing so, it is possible to make the angle of zero-order diffracted light substantially the same at any position of the observation range. Therefore, it is possible to acquire an electronic image with good contrast at any position of the observation area.

Moreover, in each sample observation devices of the embodiments as stated above, it is preferable that the image forming optical system includes an aperture stop. Moreover, in each sample observation devices of the embodiments as stated above, it is preferable that the image forming optical system includes an objective lens, and the aperture stop is disposed at the objective lens.

By doing so, it is possible to acquire an image with good contrast in accordance with the sample.

Figure 20:
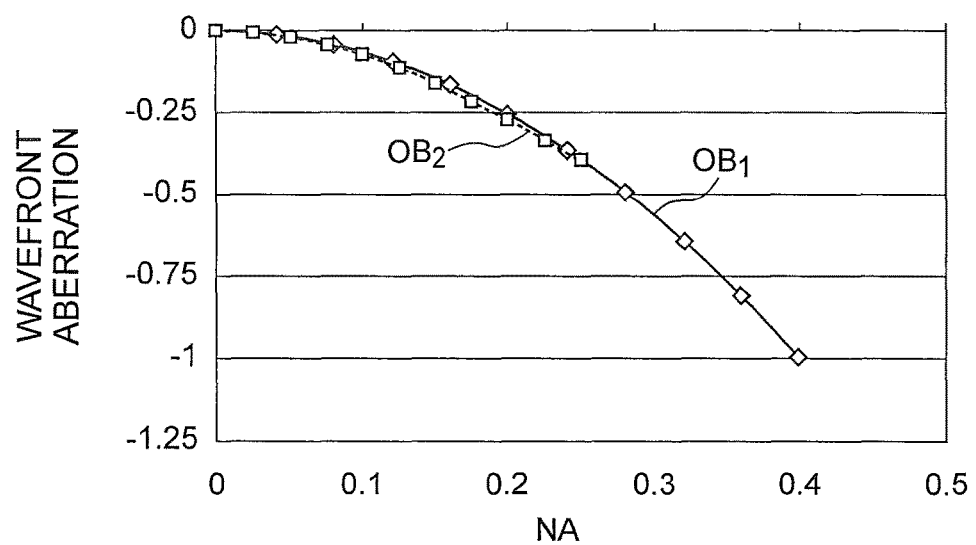
FIG. 20 is a diagram showing the wavefront aberration at two objective lenses each having different numerical aperture.

In the following description, a microscope objective lens (hereinafter, referred to as "objective lens") is used. FIG. 20 is a diagram showing the wavefront aberration at two objective lenses each having different numerical aperture (NA). In FIG. 20, the curve shown in solid line and the curve shown in dotted lines both indicate the relationship between numerical aperture and the amount of wavefront aberration. The solid line indicates the amount of wavefront aberration at an objective lens having a large numerical aperture (hereinafter, referred to as "objective lens $OB_1$" as appropriate). The dotted lines indicate the amount of wavefront aberration at an objective lens having a small numerical aperture (hereinafter, referred to as "objective lens $OB_2$" as appropriate).

The objective lens $OB_1$ and the objective lens $OB_2$ have the amount of wavefront aberration of $-\lambda/4$ at the position where the numerical aperture of both is 0.2. Therefore, it is possible to acquire an electronic image with good contrast by letting the position of the first-order diffracted light coincide with the position having the numerical aperture of 0.2.

However as compared with the numerical aperture of the objective lens $OB_2$, the numerical aperture of the objective lens $OB_1$ is large. Therefore, higher-order diffracted light than the first-order diffracted light will be incident on the objective lens $OB_1$. Here, the amount of wavefront aberration is added to the higher-order diffracted light as well. Therefore, zero-order diffracted light and the higher-order diffracted light may be mutually weakened or strengthened depending on the magnitude of the amount of wavefront aberration. As a result, it becomes difficult to acquire an electronic image with good contrast at the objective lens $OB_1$.

Therefore, by disposing the aperture stop in the objective lens $OB_1$, it is possible to control the numerical aperture of the objective lens $OB_1$. More specifically, the numerical aperture of the objective lens $OB_1$ can be made the same degree as that of the numerical aperture of the objective lens $OB_2$. As a result, it is possible to acquire an electronic image with good contrast.

The aperture stop may be disposed at any position as long as the numerical aperture can be limited at a position from the objective lens to the image-pickup device. Therefore, the image forming optical system may include the aperture stop. The objective lens may be an endoscopic objective lens, in addition to the objective lens.

Moreover, in each sample observation device of the embodiments as stated above, it is preferable that the following conditional expression (4) is satisfied:

$$0.5 < \lambda/(P \times NA_{im}) < 20 \quad (4)$$

where $\lambda$ denotes a wavelength of light incident on the image-pickup element, P denotes a pixel pitch of the image-pickup element at the image-pickup device, and $NA_{im}$ denotes a numerical aperture of the image forming optical system on the image-pickup device side.

Here, $NA_{im}$ is a value obtained by dividing the numerical aperture of the image forming optical system on the sample side by a projection magnification of the image forming optical system.

By satisfying of the conditional expression (4), it is possible to observe a colorless and transparent sample more clearly in the state of bright-field observation as well. Moreover, it is possible to acquire an electronic image with high resolution.

When falling below the lower limit value of the conditional expression (4), the Nyquist frequency of the image-pickup element greatly falls below the cut-off frequency of the image forming optical system (e.g., objective lens). Therefore, the quality of an electronic image is degraded. When exceeding the upper limit value of the conditional expression (4), pixels of the image-pickup element is too small as compared with the resolution of the image forming optical system. More specifically, the electronic image has the number of pixels that is more than the one required. Therefore, it is difficult to handle such an electronic image.

Moreover, it is preferable that each sample observation device of the embodiments as stated above includes a driving mechanism, and the driving mechanism moves at least one of the holding member, the image-pickup device and the image forming optical system along the optical axis.

By doing so, it is possible to acquire an electronic image easily. Especially, the image forming optical system and the image-pickup element are preferably moved. When the image forming optical system and the image-pickup element are moved, the sample S can be in a static state. Therefore, when the sample has a very soft structure or the object to be observed floats in the liquid as well, it is possible to acquire an electronic image without changing the state of the sample (without deforming the shape or changing the position in the liquid).

Another sample observation method of an embodiment and another sample observation device of an embodiment are described below. The sample observation methods from the ninth embodiment to the fifteenth embodiment and the sample observation devices from the fourth embodiment to the sixth embodiment are used in the state of bright-field observation. In the bright-field observation of these embodiments, the fluorescent mirror unit including the excitation filter, the dichroic mirror, and the absorption filter, which is used in the fluorescent observation, is not used. Therefore, in the state of bright-field observation, when the sample is colorless and transparent, light forming an image of the sample (hereinafter, referred to as "image forming light" as appropriate) has the wavelength band that coincides with the wavelength band of light for illumination of the sample (hereinafter, referred to as "illumination light" as appropriate) at the time of in-focusing.

Moreover, in the bright-field observation of the present embodiment, a phase film, which is used in the phase-contrast observation, and a differential interference prism, which is used in the differential interference observation, are not used. Therefore, considering light emanated from one point of the sample, a change in wavefront of light at the illumination optical system and a change in wavefront at the image forming optical system both occur at a lens only.

Moreover, in the bright-field observation of the present embodiment, a neutral density filter, which is for partially dimming of light flux from the sample, is not used. Therefore, in the state of bright-field observation, a change of intensity in the image forming light does not arise from the sample to the image of the sample (excluding a change in intensity resulting from a lens).

A sample observation method of the ninth embodiment includes an acquisition step of acquiring an electronic image of a sample, and a subtraction step of subtracting a DC component from a signal of the electronic image, and the acquisition step is performed in the state of bright-field observation, and the electronic image at the subtraction step is an image acquired in a second predetermined state, and before reaching the second predetermined state, the position of the sample and the in-focus position of the image forming optical system are made to be coincident using light of a first wavelength band, and in the second predetermined state, an optical image of the sample is formed using a second wavelength band at least, and the second wavelength band is coincident with a part of the first wavelength band, or is different from the first wavelength band.

Referring to FIG. 1, the sample observation method of the ninth embodiment is described below. FIG. 1 is a flowchart of the sample observation method of the ninth embodiment.

The sample observation method of the ninth embodiment includes an acquisition step S10 and a subtraction step S20. Accordingly, in the sample observation method of the ninth embodiment, it is possible to acquire a clear electronic image.

In the sample observation method of the ninth embodiment, the acquisition step S10 is executed firstly. At the acquisition step S10, an electronic image of the sample is acquired. The image of the sample (optical image) is formed by the image forming optical system. At the time of acquiring the electronic image, the image of the sample is picked up by an image-pickup element, such as a CCD or a CMOS. The image of the sample is converted into an electronic image (digital data) through the image pickup. Since the image of the sample is formed in the state of bright-field observation, an acquisition of the electronic image also is performed in the state of bright-field observation. Hereinafter, the electronic image of the sample is referred to as "electronic image" as appropriate.

When the acquisition step S10 ends, the subtraction step S20 is executed. At the subtraction step S20, a DC component (bias component) is subtracted from a signal of the electronic image. The electronic image at the subtraction step S20 is an image acquired in a second predetermined state.

The electronic image at the subtraction step S20 is an image in the second predetermined state, i.e., when an optical image of the sample is formed using the light of the second wavelength band. Before reaching the second predetermined state, the position of the sample and the in-focus position of the image forming optical system are made to be coincident using the light of the first wavelength band. Then the second wavelength band coincides with a part of the first wavelength band, or is different from the first wavelength band. As just described, in the sample observation method of the ninth embodiment, the wavelength band of light is different between before acquisition of an electronic image and at a time of acquisition of the electronic image (moment). Hereinafter, the in-focus position of the image forming optical system is referred "in-focus position" as appropriate.

Here, if the sample is a lattice-like phase object, when the sample is illuminated with light, zero-order light and diffracted light emanate from the sample. In the state where the image forming optical system has axial chromatic aberration to some extent, the wavelength band of light is made to be different between before acquisition of an electronic image and at a time of acquisition of the electronic image. By doing so, a difference in wavefront aberration (difference in optical path length) occurs between light before acquisition of an electronic image and light at a time of acquisition of the electronic image. This point is described with reference to FIG. 21A and FIG. 21B to FIG. 26. In the following description, first-order diffracted light is used as the diffracted light. Moreover, the image forming optical system is assumed to have axial chromatic aberration to some extent.

Figure 21A:
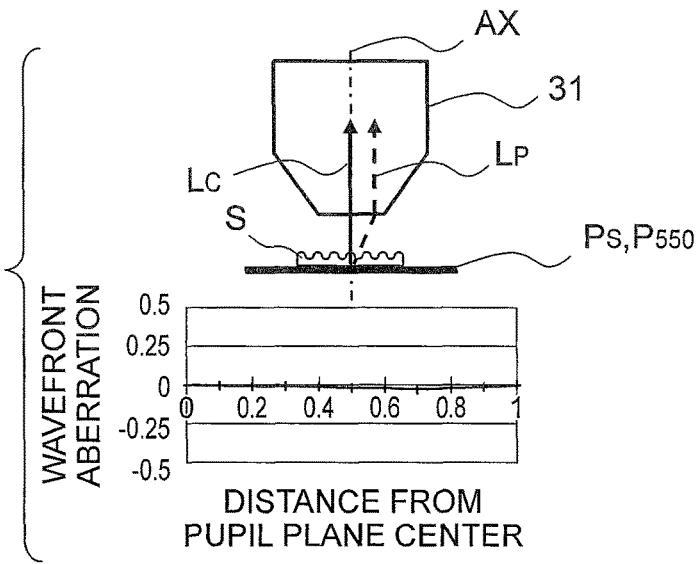
FIG. 21A and FIG. 21B are diagrams showing a relationship between an in-focus position at a first wavelength band (center wavelength $\lambda 1=550$ nm) and a in-focus position at a second wavelength band (center wavelength $\lambda 2=450$ nm), and the wavefront aberration, where
Figure 21B:
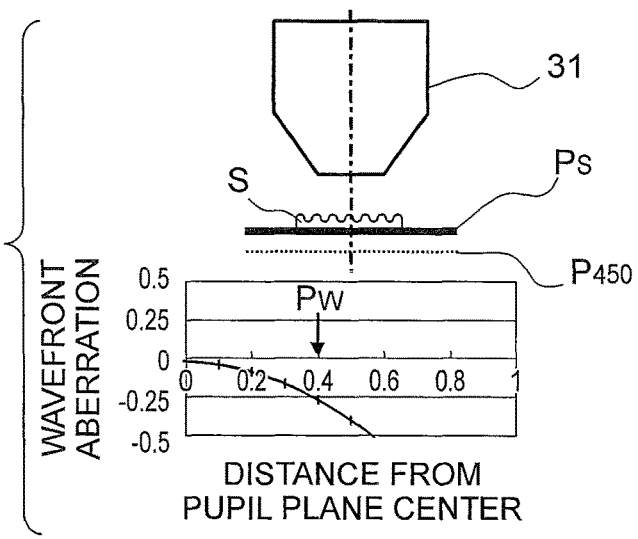
Figure 22:
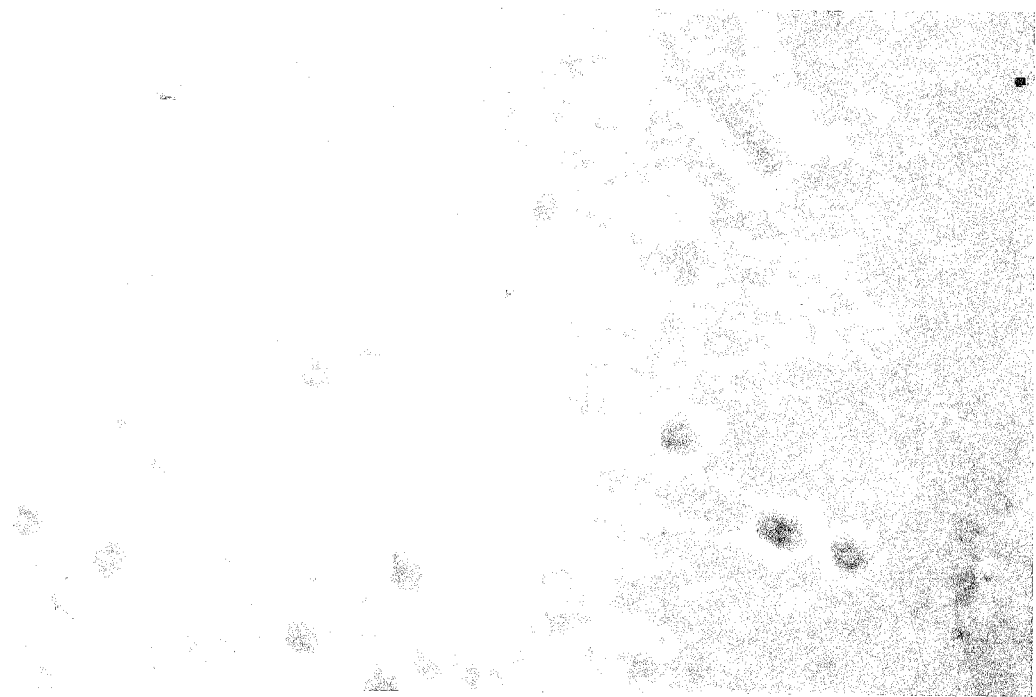
FIG. 22 is an electronic image of the sample at the first wavelength band (center wavelength $\lambda 1=550$ nm).
Figure 23:
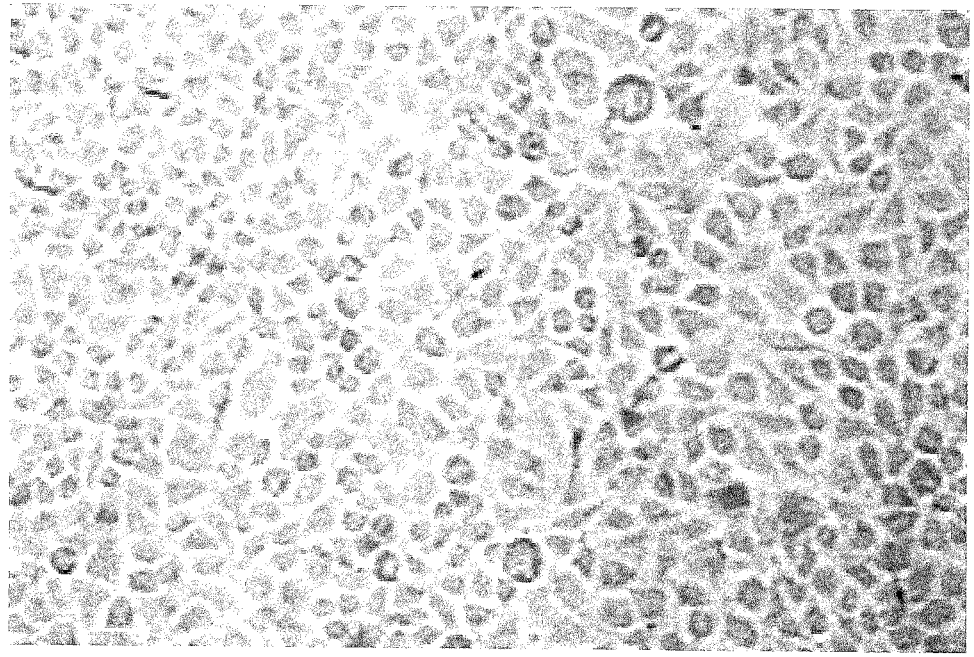
FIG. 23 is an electronic image of the sample at the second wavelength band (center wavelength $\lambda 2=450$ nm).
Figure 24A:
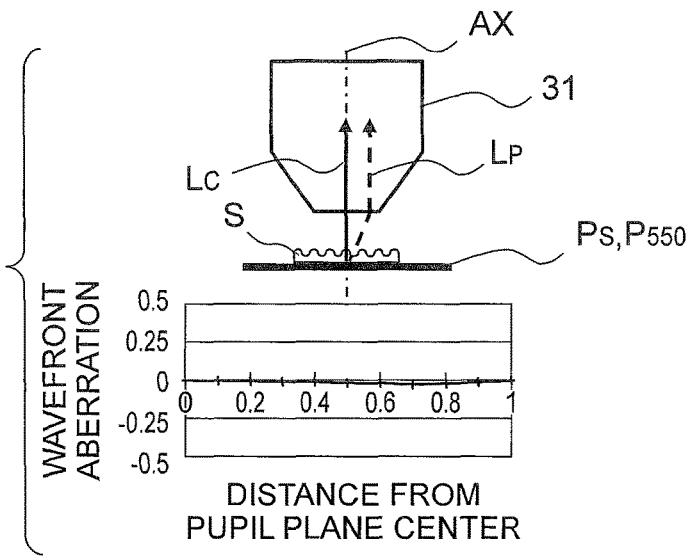
FIG. 24A and FIG. 24B are diagrams showing a relationship between the in-focus position at the first wavelength band (center wavelength $\lambda 1=550$ nm) and a in-focus position at the second wavelength band (center wavelength $\lambda 2=650$ nm), and the wavefront aberration, where
Figure 24B:
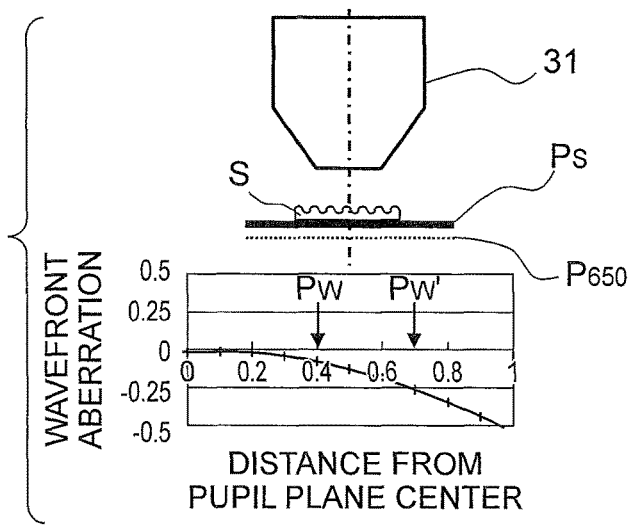
Figure 25:
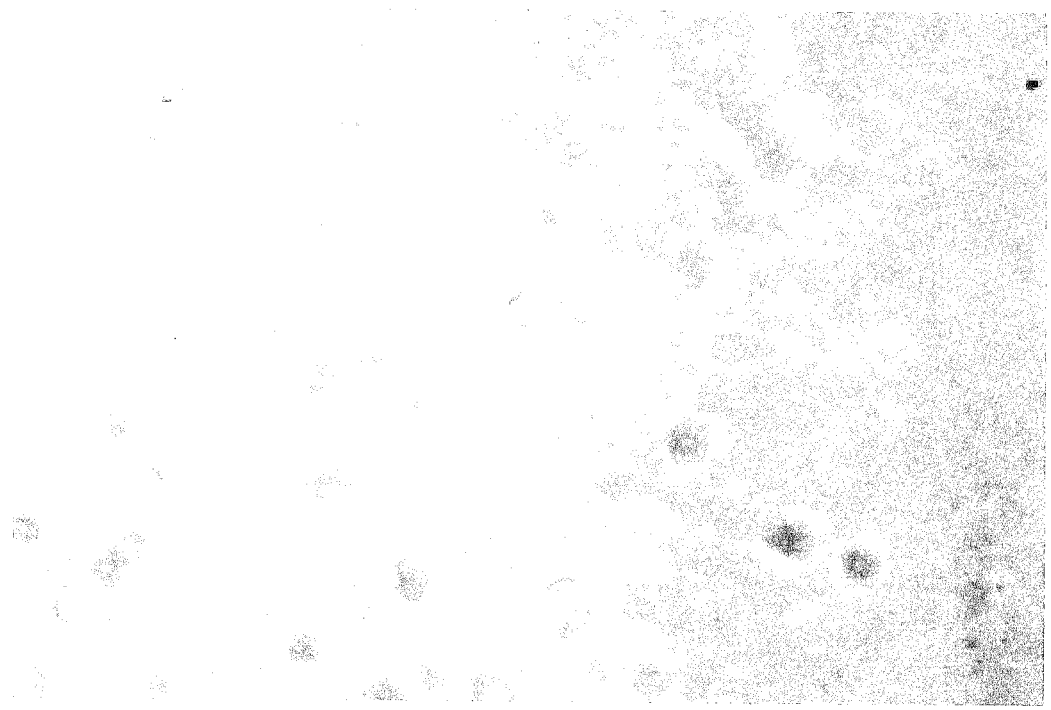
FIG. 25 is electronic image of the sample at the first wavelength band (center wavelength $\lambda 1=550$ nm).
Figure 26:
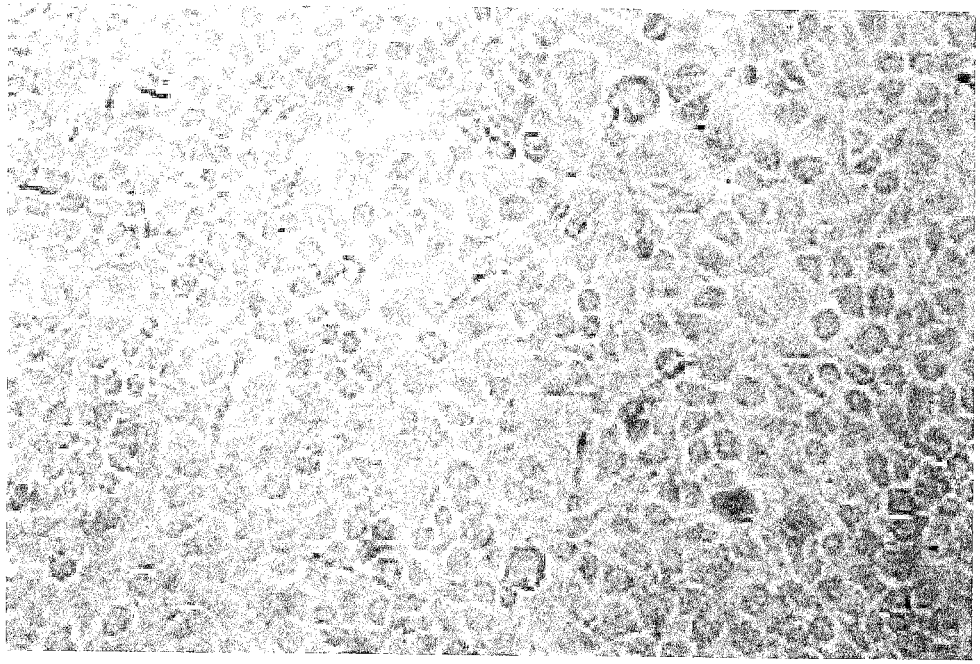
FIG. 26 is an electronic image of the sample at the second wavelength band (center wavelength $\lambda 2=650$ nm).

FIG. 21A and FIG. 21B are diagrams showing the relationship between the in-focus position at the first wavelength band (center wavelength $\lambda 1=550$ nm) and the in-focus position at the second wavelength band (center wavelength $\lambda 2=450$ nm), and the wavefront aberration, where FIG. 21A is a diagram showing the state where the position of the sample and the in-focus position are allowed to coincide using the light of the first wavelength band, and FIG. 21B is a diagram showing the state where the optical image of the sample is formed using the light of the second wavelength band. FIG. 22 is an electronic image of the sample at the first wavelength band (center wavelength $\lambda 1=550$ nm). FIG. 23 is an electronic image of the sample at the second wavelength band (center wavelength $\lambda 2=450$ nm). FIG. 24A and FIG. 24B are diagrams showing the relationship between the in-focus position at the first wavelength band (center wavelength $\lambda 1=550$ nm) and the in-focus position at the second wavelength band (center wavelength $\lambda 2=650$ nm), and the wavefront aberration, where FIG. 24A is a diagram showing the state where the position of the sample and the in-focus position are allowed to coincide using light of the first wavelength band, and FIG. 24B is a diagram showing the state where the optical image of the sample is formed using light of the second wavelength band. FIG. 25 is an electronic image of the sample at the first wavelength band (center wavelength $\lambda 1=550$ nm). FIG. 26 is an electronic image of the sample at the second wavelength band (center wavelength $\lambda 2=650$ nm). Each electronic image in FIG. 22, FIG. 23, FIG. 25 and FIG. 26 is an image after executing the subtraction step S20. Moreover, each sample in FIG. 22, FIG. 23, FIG. 25 and FIG. 26 is a cell.

Moreover, the graphs represent the amount of wavefront aberration at the pupil position. The vertical axis of the graphs represents the amount of wavefront aberration (in the unit of wavelength), and the horizontal axis represents the distance from the center of the pupil plane (on the pupil plane). Since the distance from the center of the pupil plane is normalized, they are unitless numbers. The numerical value 0 on the horizontal axis represents the center position of the pupil plane, and 1 represents the outermost position of the pupil plane.

As shown in FIG. 21A, light emanated from one point on the optical axis includes light ray $L_C$ and light ray $L_P$. The light ray $L_C$ travels along the optical axis. Here, a point at the intersection of the light ray $L_C$ with the pupil plane coincides with the center position of the pupil plane. On the other hand, the light ray $L_P$ is incident on the image forming optical system 31 at a predetermined angle with respect to the optical axis AX. Here, a point at intersection between the light ray $L_P$ with the pupil plane coincides with a position away from the center of the pupil plane by a predetermined distance.

When the sample S is illuminated with illumination light (parallel light flux), zero-order diffracted light and first-order diffracted light emanate form the sample S. Here, taking notice of the point where the sample S and the optical axis intersect (one point on the optical axis), since zero-order diffracted light is not diffracted, zeroth-diffracted light emanated from this point travels along the optical axis and reaches the center of the pupil. Therefore, zero-order diffracted light can be considered as the light ray $L_C$. On the other hand, since first-order diffracted light is diffracted in a predetermined direction, the first-order diffracted light emanated from this point is incident on the image forming optical system 31 at a predetermined angle with respect to the optical axis. The first-order diffracted light incident on the image forming optical system 31 reaches a position away from the center of the pupil plane. Therefore, first-order diffracted light can be considered as the light ray $L_P$.

Firstly, the case where the center wavelength $\lambda 1$ of the first wavelength band is 550 nm, and the center wavelength of the second wavelength band is 450 nm is described below. In a state where the position of the sample and the in-focus position are allowed to coincide using the light of the first wavelength band, the in-focus position $P_{550}$ of the first wavelength band coincides with the position $P_S$ of the sample S. In this state, as shown in FIG. 21A, the amount of wavefront aberration is substantially 0 at any position of the pupil plane. This indicates that the amount of wavefront aberration in the zero-order diffracted light and the amount of wavefront aberration in the first-order diffracted light both are substantially 0. Since the value obtained by multiplying the amount of wavefront aberration by $(2\pi/\lambda)$ is equivalent to the phase amount, at the time of in-focusing, a change in phase does not arise for both of the zero-order diffracted light and the first-order diffracted light. Since the phase of the first-order diffracted light remains to be delayed relative to the phase of the zero-order diffracted light by $\pi/2$, the phase difference is expressed by $\psi=0-(-\pi/2)=\pi/2$. In this case, since $2A_1A_2 \cos \psi=0$, phase information cannot be obtained in the form of contrast information. As a result, the electronic image becomes an image without contrast as shown in FIG. 22.

Meanwhile, in a state where the optical image of the sample is formed using light of the second wavelength band, the in-focus position of the second wavelength band is displaced from the position of the sample. In FIG. 21B, the in-focus position $P_{450}$ of the second wavelength band is displaced downward (direction away from the image forming optical system 31) from the position $P_S$ (in-focus position $P_{550}$) of the sample S. In this state, as shown in the graph of FIG. 21B, although the amount of wavefront aberration is 0 at the center of the pupil plane, the wavefront aberration occurs at a position away from the center of the pupil plane. Here, the wavefront aberration denotes a displacement of actual wavefront with reference to a reference wavefront, and this displacement denotes a displacement of phase. Therefore, if the first-order diffracted light is positioned in the range where wavefront aberration occurs, the phase of the first-order diffracted light is equivalent to a phase that the amount of wavefront aberration is added to a phase which the first-order diffracted light has originally. As just described, by making the wavelength band of light to be different between before acquisition of an electronic image and at a time of acquisition of the electronic image, the phase of the first-order diffracted light can be changed. As shown in the graph of FIG. 21B, when the position $P_W$ is set at a position where a distance from the pupil center is 0.4, the amount of wavefront aberration at the position $P_W$ is $-\lambda/4$.

By doing so, it is possible to make the amount of wavefront aberration at the first-order diffracted light $-\lambda/4$ while keeping the amount of wavefront aberration at the zero-order diffracted light 0. As described above, since the value obtained by multiplying the amount of wavefront aberration by $(2\pi/\lambda)$ equals the phase amount, at the time of defocusing, a change in phase does not arise for the zero-order diffracted light, but a change in phase arise for the first-order diffracted light. Specifically, in the first-order diffracted light, the phase further delays by $\pi/2$ in addition to the original phase delay of $\pi/2$. Since the phase of the first-order diffracted light delays by it relative to the phase of the zero-order diffracted light, the phase difference is expressed by then $\psi=0-(-\pi)=\pi$. In this case, since $2A_1A_2 \cos \psi \neq 0$, phase information can be obtained in the form of contrast information. As a result, as shown in FIG. 23, the electronic image becomes an image with obvious contrast. This electronic image may be displayed on a display device, for example, whereby an observer can observe the sample S (image of the sample S) clearly.

Next, the case where the center wavelength $\lambda 1$ of the first wavelength band is 550 nm, and the center wavelength $\lambda 2$ of the second wavelength band is 650 nm is described below. In the state where the position of the sample S and the in-focus position are allowed to coincide using the light of the first wavelength band, the in-focus position $P_{550}$ of the first wavelength band coincides with the position $P_S$ of the sample S. This is the same as in FIG. 21A. Therefore, as shown in FIG. 25, the electronic image becomes an image without contrast.

Meanwhile, in a state where the optical image of the sample is formed using light of the second wavelength band, the in-focus position $P_{650}$ of the second wavelength band is displaced downward (direction away from the image forming optical system 31) from the position $P_S$ (in-focus position $P_{550}$) of the sample S. In this state, as shown in the graph of FIG. 24B, although the amount of wavefront aberration is 0 at the center of the pupil plane, the wavefront aberration occurs at a position away from the center of the pupil plane. Here, the in-focus position $P_{650}$ is different from the in-focus position $P_{450}$.

In this case, the amount of wavefront aberration at the position of the first-order diffracted light on the pupil plane is different between FIG. 24B and FIG. 21B. As shown in the graph of FIG. 24B, the amount of wavefront aberration is about $-1\lambda/10$ at the position $P_W$ where a distance from the pupil center is 0.4.

As just described, by making the wavelength band of light to be different between before acquisition of an electronic image and at a time of acquisition of the electronic image, the amount of wavefront aberration at the first-order diffracted light can be $-\lambda/10$ while keeping the amount of wavefront aberration at the zero-order diffracted light 0. Although the amount of wavefront aberration is different, this is the same state as in FIG. 21B. Therefore, as shown in FIG. 26, the electronic image becomes image with obvious contrast. An observer so can observe the sample S (image of the sample S) clearly.

In FIG. 21B, the amount of wavefront aberration at the first diffracted light is $-\lambda/4$. In this case, a relationship between the phase of zero-order diffracted light and the phase of first-order diffracted light is a relationship of opposite phase. In the relationship of the opposite phase, the zero-order diffracted light and the first-order diffracted light are mutually weakened. Therefore, in the electronic image, brightness of the sample S becomes dark as compared with the background. This corresponds to dark contrast in phase-contrast observation.

Moreover, when the amount of wavefront aberration at the first-order diffracted light is $+\lambda/4$, a relationship between the phase of zero-order diffracted light and the phase of first-order diffracted light is a relationship of same phase. In the relationship of the same phase, the zero-order diffracted light and the first-order diffracted light are mutually strengthened. Therefore, in the electronic image, brightness of the sample S becomes bright as compared with the background. This corresponds to bright contrast in phase-contrast observation.

Moreover, diffraction angle of the diffracted light differs depending on the spatial frequency of the sample S. For instance, when the sample S is a lattice-like phase object, spacing of the lattice is wide means that a spatial frequency included in the sample S is low. On the other hand, spacing of the lattice is narrow means that a spatial frequency included in the sample S is high. Here, as the spacing of the lattice becomes wider the diffraction angle becomes small, and the spacing of the lattice becomes narrower the diffraction angle becomes large. Therefore, when the sample S has a low spatial frequency, the diffraction angle is small, and when the sample S has a high spatial frequency, the diffraction angle is large.

Many structures having various spatial frequencies are included in cells. Therefore, when the sample S is cells, the appearance of the image of the sample changes depending on that the position having the amount of wavefront aberration of $-\lambda/4$ is made to be coincident with the position of the first-order diffracted light at a spatial frequency of various spatial frequencies.

When the second wavelength band is set so that the amount of wavefront aberration becomes $-\lambda/4$ at a position of the first-order diffracted light at high spatial frequency, in the electronic image, a part having the high spatial frequency will be clear. On the other hand, when the second wavelength band is set so that the amount of wavefront aberration becomes $-\lambda/4$ at a position of the first-order diffracted light at low spatial frequency, in the electronic image, a part having the low spatial frequency will be clear.

For instance, as shown in FIG. 24B, when the position $P_W'$ is set at a position where a distance from the pupil center is 0.64, then the amount of wavefront aberration at the position $P_W'$ is $-\lambda/4$. Therefore, if the sample S has a spatial frequency that the first-order diffracted light pass through the position $P_W'$, then a part corresponding to such a spatial frequency can be observed clearly.

Moreover, the in-focus position at the second wavelength band may be displaced upward from the position (in-focus position of the first wavelength band) of the sample S. For instance, the center wavelength $\lambda 1$ of the first wavelength band may be 650 nm, and the center wavelength $\lambda 2$ of the second wavelength band may be 550 nm.

In the observation method of the present embodiment, a difference in center wavelength is not so large between the first wavelength band and the second wavelength band. In this case, even when the wavelength band of light is made to be different between before acquisition of an electronic image and at a time of acquisition of the electronic image, the incident position of the first-order diffracted light hardly changes with respect to the image forming optical system 31. For this reason, a change of the position of the first-order diffracted light on the pupil plane also can be considered as slight. Therefore, it is possible to change the amount of wavefront aberration added to the first-order diffracted light simply by changing the wavelength band.

As stated above, at the acquisition step S10, the wavelength band of light is different between before acquisition of an electronic image and at a time of acquisition of the electronic image. Therefore, $2A_1A_2 \cos \psi \neq 0$ holds. In this case, the intensity I of light on the image plane is as follows, $I=A_1^2+A_2^2+2A_1A_2 \cos \psi$.

Here, $A_1^2+A_2^2$ represents the DC component (bias component) at the image of the sample, i.e., the DC component (bias component) of a signal of the electronic image. Among them, the amplitude $A_1^2$ of the zero-order diffracted light has a very large value. Therefore, at the subtraction step S20, the value of $A_1^2$ is made smaller. By doing so, it is possible to make the value of $2A_1A_2 \cos \psi$ relatively large with reference to the value of $A_1^2+A_2^2$. As a result, it is possible to observe the sample S (image of the sample S) clearly.

As stated above, according to the sample observation method of the ninth embodiment, it is possible to observe a colorless and transparent sample clearly in the state of bright-field observation as well.

The sample observation method of the tenth embodiment includes an amplification step after the subtraction step, and at the amplification step, a signal of an electronic image subjected to the subtraction step is amplified.

Referring to FIG. 12A, the sample observation method of the tenth embodiment is described below. FIG. 12A is a flowchart of the sample observation method of the tenth embodiment.

As shown in FIG. 12A, the sample observation method of the tenth embodiment includes an amplification step S30-2 in addition to the acquisition step S10 and the subtraction step S20. Accordingly, in the sample observation method of the tenth embodiment, it is possible to acquire a clearer electronic image.

As described above, $A_1^2+A_2^2$ represents the DC component of the sample image, i.e., the DC component of a signal of the electronic image. At the subtraction step S20, the value of $A_1^2$ is made smaller, whereby the value of $2A_1A_2 \cos \psi$ is made relatively large with reference to the value of $A_1^2+A_2^2$.

Whereas, in the sample observation method of the tenth embodiment, the amplification step S30-2 is executed after the acquisition step S10 and the subtraction step S20 end. At the amplification step S30-2, the value of $2A_1A_2 \cos \psi$ is made larger (amplified). By doing so, it is possible to make the value of $2A_1A_2 \cos \psi$ relatively large with reference to the value of $A_1^2+A_2^2$. As a result, it is possible to observe the sample S (image of the sample S) more clearly.

The amplification step S30-2 may be used in the sample observation method of the ninth embodiment. In this case, the amplification step S30-2 is executed prior to the comparison step S30-1.

As stated above, according to the sample observation method of the tenth embodiment, it is possible to observe a colorless and transparent sample more clearly in the state of bright-field observation as well.

A sample observation method of the eleventh embodiment includes a conversion step of performing Fourier transform of a signal of an electronic image, and an inverse conversion step of performing inverse Fourier transform, and the conversion step is performed prior to the subtraction step, and the inverse conversion step is performed at least after the subtraction step.

Referring to FIG. 12B and FIG. 13A and FIG. 13B, a sample observation method of the eleventh embodiment is described below. FIG. 12B is a flowchart of the sample observation method of the eleventh embodiment. FIG. 13A and FIG. 13B are diagrams showing the magnitude at each spatial frequency, where FIG. 13A is a diagrams showing the state before performing the subtraction step, and FIG. 13B s a diagrams showing the state after performing the subtraction step.

As shown in FIG. 12B, the sample observation method of the eleventh embodiment includes a conversion step S15-1 and an inverse conversion step S30-3 in addition to the acquisition step S10 and the subtraction step S20. Accordingly, in the sample observation method of the eleventh embodiment, it is possible to acquire clearer electronic images easily.

As described above, at the subtraction step S20, the value of $A_1^2$ is made smaller, whereby the value of $2A_1A_2 \cos \psi$ is made relatively large with reference to the value of $A_1^2+A_2^2$. Here, when the subtraction step S20 is executed at a frequency space, subtraction can be performed effectively.

Referring to FIG. 13A and FIG. 13B, subtraction at the subtraction step S20 is described below. As described above, a sample such as cell includes a structure having various spatial frequencies. Therefore, if brightness of the image of the sample S can be separated for each spatial frequency, subtraction can be performed for each spatial frequency.

Therefore, in the sample observation method of the eleventh embodiment, the conversion step S15-1 is executed after the acquisition step S10 ends. At the conversion step S15-1, Fourier transform is performed for a signal of an electronic image. As a result, as shown in FIG. 13A, the magnitude (vertical axis, corresponding to brightness) can be separated for each spatial frequency. In FIG. 13A, the numerical values on the horizontal axis represent spatial frequencies. At the spatial frequency is 0, the magnitude is 100, and at the spatial frequency is 1, the magnitude is 30.

Here, the values of spatial frequency (numerical values on the horizontal axis) correspond to the order of diffracted light. Therefore, the magnitude (numerical value on the vertical axis) at the spatial frequency of 0 corresponds to the brightness of zero-order diffracted light. Similarly, the magnitude at the spatial frequency of 1 corresponds to the brightness of first-order diffracted light. Then, after the conversion step S15-1 ends, the subtraction step S20 is executed. At this subtraction step S20, the magnitude at the spatial frequency of 0 is made smaller. For instance, as shown in FIG. 13B, the magnitude at the spatial frequency of 0 is decreased to half from 100 to 50. This corresponds to that the value of $A_1^2$ is smaller. By doing so, it is possible to make the brightness of zero-order light smaller.

Next, the inverse conversion step S30-3 is executed. At the inverse conversion step S30-3, inverse Fourier transform is performed. Accordingly, it is possible to acquire a signal of an electronic image. The brightness of zero-order light, i.e., the value of $A_1^2$ is made smaller at the subtraction step S20. Therefore, it is possible to make the value of $2A_1A_2 \cos \psi$ relatively large with reference to the value of $A_1^2+A_2^2$. As a result, it is possible to observe the sample S (image of the sample S) more clearly.

The conversion step S15-1 and the inverse conversion step S30-3 may be used in the sample observation method of the tenth embodiment. In this case, the conversion step S15-1 is executed prior to the subtraction step S20. The inverse conversion step S30-3 is executed after the subtraction step S20.

As stated above, according to the sample observation method of the eleventh embodiment, it is possible to observe a colorless and transparent sample more clearly in the state of bright-field observation as well.

A sample observation method of the twelfth embodiment includes an acquisition in advance step and a normalization step, and at the acquisition in advance step, an electronic image is acquired without a sample, and at the normalization step, using the electronic image, an electronic image of a sample is normalized, and the normalization step is performed prior to the subtraction step.

Referring to FIG. 14, the sample observation method of the twelfth embodiment is described below. FIG. 14 is a flowchart of the sample observation method of the twelfth embodiment.

As shown in FIG. 14, the sample observation method of the twelfth embodiment includes an acquisition in advance step S00 and a normalization step S15-2 in addition to the acquisition step S10 and the subtraction step S20. Accordingly, in the sample observation method of the twelfth embodiment, it is possible to acquire a clearer electronic image.

In FIG. 14, the amplification step S30-2 is executed after the subtraction step S20, but amplification step S30-2 is not essential.

Brightness of the image of the sample S may be affected by the illumination optical system or by the image forming optical system. For instance, when light passes through the illumination optical system or the image forming optical system, the light after passing therethrough generates unevenness in brightness. In this case, due to such unevenness in brightness of the illumination optical system or the image forming optical system, the unevenness in brightness is also generated in the image of the sample S. Since such unevenness in brightness will degrade the quality of an electronic image, it is preferable to remove such unevenness in brightness.

Therefore, in the sample observation method of the twelfth embodiment, the acquisition in advance step S00 is executed prior to the acquisition step S10. At the acquisition in advance step S00, an electronic image A is acquired without a sample S. At this time, the electronic image A will be an image with unevenness in brightness only.

Next, the acquisition step S10 is executed, and thereby an electronic image B of the sample S is acquired. This electronic image B will be an image including unevenness in brightness due to the illumination optical system or the image forming optical system in addition to the image of the sample S. Therefore, the normalization step S15-2 is executed. At this normalization step S15-2, the electronic image B is normalized with the electronic image A. More specifically, the following operation is executed at the normalization step S15-2:

Electronic image $B$/electronic image $A$.

Accordingly, the unevenness in brightness at the electronic image B is canceled with the unevenness in brightness at the electronic image A. Therefore, the electronic image subjected to normalization becomes an image with reduced unevenness in brightness due to the illumination optical system or the image forming optical system.

After the normalization step S15-2 ends, the subtraction step S20 is executed. At the subtraction step S20, the value of $A_1^2$ of an electronic image subjected to normalization is made small, and thereby the value of $2A_1A_2 \cos \psi$ is made relatively large with reference to the value of $A_1^2+A_2^2$. As a result, it is possible to observe the sample S (image of the sample S) more clearly.

The acquisition in advance step S00 and the normalization step S15-2 may be used in the sample observation method of the tenth embodiment and the sample observation method of the eleventh embodiment. In this case, the acquisition in advance step S00 is executed prior to the acquisition step S10. The normalization step S15-2 is executed prior to the subtraction step S20.

As stated above, according to the sample observation method of the twelfth embodiment, it is possible to observe a colorless and transparent sample more clearly in the state of bright-field observation as well.

In a sample observation method of the thirteenth embodiment, the second wavelength band is changed with reference to the first wavelength band a plurality of times, and at each second wavelength band after changing, the acquisition step and the subtraction step are performed, and thereby a plurality of electronic images are generated after the subtraction step, and the plurality of electronic images generated are added.

According to the sample observation method of the thirteenth embodiment, at the time of generating an electronic image, an image with high contrast at each spatial frequency from a low spatial frequency to a high spatial frequency is used. Therefore, at the electronic image generated, the contrast becomes high at every spatial frequency. As a result, it is possible to observe the sample S (image of the sample S) clearly.

As stated above, according to the sample observation method of the thirteenth embodiment, it is possible to observe a colorless and transparent sample clearly in the state of bright-field observation as well.

In the sample observation method of the fourteenth embodiment, before addition, a part with highest contrast in each of a plurality of electronic images is extracted, and the addition is performed using the extracted parts.

According to the sample observation method of the fourteenth embodiment, at the time of generating an electronic image by addition, a part with highest contrast only for each spatial frequency is used. Therefore, at the electronic image generated, the contrast becomes very high at every spatial frequency. As a result, it is possible to observe the sample S (image of the sample S) more clearly.

As stated above, according to the sample observation method of the fourteenth embodiment, it is possible to observe a colorless and transparent sample more clearly in the state of bright-field observation as well.

In the sample observation method of the fifteenth embodiment, a change of the second wavelength band is made while keeping the sign of the amount of wavefront aberration in the second predetermined state same.

As described above, when the amount of wavefront aberration at the first-order diffracted light is $-\lambda/4$, the electronic image will be a dark contrast image. More specifically, in the electronic image, an image of the sample S becomes dark as compared with the background. On the other hand, when the amount of wavefront aberration at the first-order diffracted light is $+\lambda/4$, the electronic image will be a bright contrast image. More specifically, in the electronic image, an image of the sample S becomes bright as compared with the background.

Therefore, it is preferable to use images with the amount of wavefront aberration of the same sign at the time of generating an electronic image by the addition. By doing so, it is possible to make the electronic image generated to be an image based on dark contrast only or an image based on bright contrast only. As a result, it is possible to observe the sample S (image of the sample S) more clearly.

As stated above, according to the sample observation method of the fifteenth embodiment, it is possible to observe a colorless and transparent sample more clearly in the state of bright-field observation as well.

A sample observation device of the present embodiment is described below. A sample observation device from the fourth embodiment to the sixth embodiment includes a light source, an illumination optical system, an image forming optical system, an image-pickup device, and an image processing device, and the illumination optical system is disposed so as to irradiate a sample with illumination light from the light source, and the image forming optical system is disposed so that light from the sample is incident thereon and an optical image of the sample is formed, and the image-pickup device is disposed at the position of the optical image, and the image processing device is configured to implement the sample observation methods from the ninth embodiment to the fifteenth embodiment as stated above.

Figure 27:
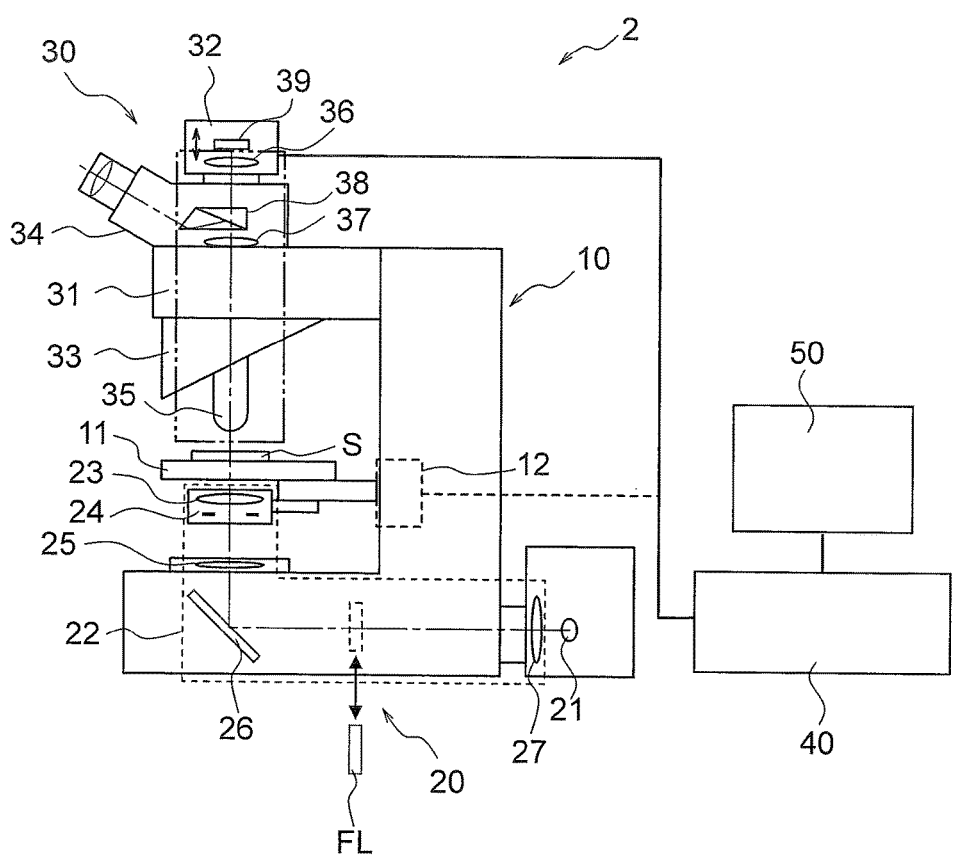
FIG. 27 is a diagram showing a configuration of the sample observation device of the fourth embodiment.

The configuration of the sample observation device of the fourth embodiment is shown in FIG. 27. The sample observation device 2 is an observation system base on an upright microscope. The same reference numerals are assigned to the same components as those of the sample observation device 1, and their descriptions are omitted.

In the sample observation device 2, an illumination part 20 includes a light source 21 and an illumination optical system 22. The illumination optical system 22 includes a condenser lens 23, an aperture stop 24, and an optical filter FL. As shown in FIG. 27, the illumination optical system 22 may include a lens 25, a mirror 26 and a lens 27. In FIG. 27, the condenser lens 23 and the aperture stop 24 are held at a stage 11. The illumination optical system 22 is disposed in an optical path from the light source 21 to the stage 11.

The procedure to implement a sample observation method of one embodiment is described using the sample observation device 2. In the following description, the sample observation method of the ninth embodiment is used as an example. A white light source is used as the light source 21.

Firstly, an observer sets the illumination optical system 22 and the image forming optical system 31 in the state of a bright-field observation. Next, the observer places the sample S on the stage 11. Then, the observer moves the sample by eye to the position where the observer thinks that it is displaced from the in-focus position. Accordingly, the position of the sample S and the in-focus position are made to be different in the state of bright-field observation. Next, the image processing device 40 is activated. These steps may be performed in random order.

When the image processing device 40 is activated, the sample observation device is ready to pick up an image of the sample S, and so the acquisition step S10 is executed. By the acquisition step S10 is executed, an electronic image is acquired. The electronic image acquired at the acquisitions step S10 is stored in a temporary storage unit (not shown) in the image processing device 40.

Next, the subtraction step S20 is executed. At the subtraction step S20, by the value of $A_1^2$ is made to be small, the value of $2A_1A_2 \cos \psi$ becomes relatively large with reference to the value of $A_1^2+A_2^2$. The execution result at the subtraction step S20 is displayed on the display device 50, for example.

As stated above, the position of the sample S is set by eye. In this case, since it is highly likely that the position of the sample S and the in-focus position differ greatly, the image of the sample S is defocused greatly. Therefore, even when the image of the sample S is picked up, the observer cannot observe an electronic image thereof on the display device 50.

Therefore, the observer manipulates the focusing knob to move the sample S toward the in-focus position. If the sample S is far away from the objective lens 35, the observer may move the stage 11 so as to move the sample S toward the objective lens 35. On the other hand, when the sample S is very close to the objective lens 35, the observer may move the stage 11 so as to move the sample S away the objective lens 35.

While the sample S is moved, image-pickup is continuously performed. Therefore, the acquisition step S10 and the subtraction step S20 also are continuously executed. Then, the observer can move the sample S along the optical axis while viewing an electronic image on the display device 50 so as to let the position of the sample S coincides with the in-focus position. At this time, since an optical filter is not disposed in the optical path of the illumination optical system 22, the sample S is illuminated with white light (light of the first wavelength band). The in-focus position at this time can be considered as a position where focusing is established with green light (light with wavelength of 500 nm to 560 nm).

Next, an optical filter FL is inserted in the optical path of the illumination optical system 22. Here, a wavelength band (transmission property) of the optical filter FL is assumed that the center wavelength is 450 nm and the wavelength width is ±20 nm. In this case, the wavelength band of the optical filter FL coincides with a part of the wavelength band of white light.

When the optical filter FL is inserted in the optical path, an optical image of the sample is formed using the light of the second wavelength band. Then, an electronic image is acquired using the light of the second wavelength band. Accordingly, the wavelength band of light is made to be different between before acquisition of an electronic image and at a time of acquisition of the electronic image (moment). As a result, it is possible to observe the sample S (image of the sample S) clearly.

As stated above, according to the sample observation device of the fourth embodiment, it is possible to observe a colorless and transparent sample clearly in the state of bright-field observation as well.

Figure 28:
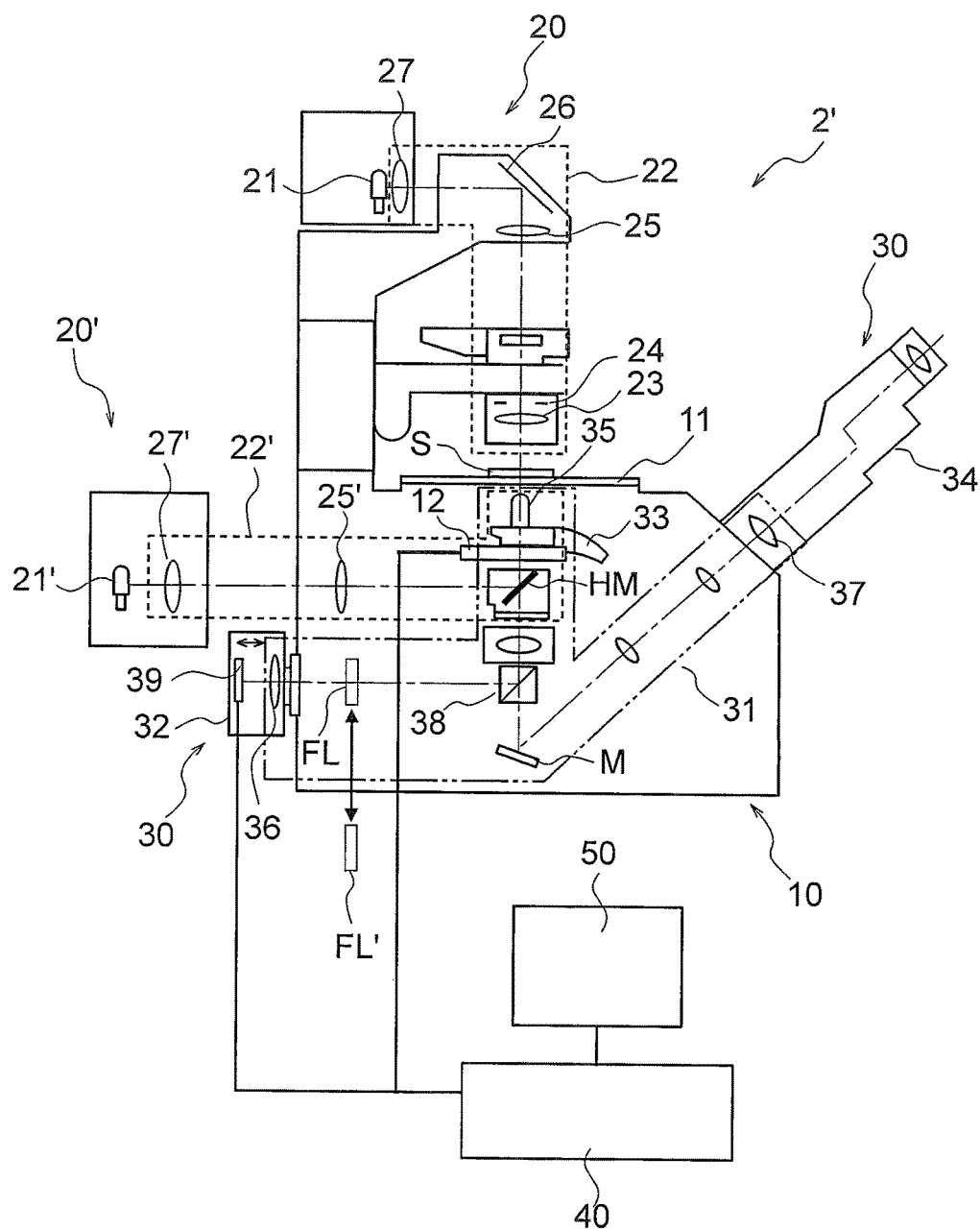
FIG. 28 is a diagram showing a configuration of the sample observation device of the fifth embodiment.

The configuration of the sample observation device of the fifth embodiment is shown in FIG. 28. The sample observation device 2' is an observation system based on an inverted microscope. The same reference numerals are assigned to the same components as those of the sample observation device 1', and their descriptions are omitted.

In the sample observation device 2', the image forming optical system 31 includes optical filter FL and optical filter FL'. The optical filter FL is disposed in the optical path of the image forming optical system 31. The optical filter FL' is disposed outside of the optical path of the image forming optical system 31. The optical filter FL and the optical filter FL' can be exchanged.

The procedure to implement a sample observation method of one embodiment is described using the sample observation device 2'. In the following description, the sample observation method of the ninth embodiment is used as an example. A white light source is used as the light source 21'.

Firstly, an observer sets the illumination optical system 22' and the image forming optical system 31' in the state of a bright-field observation. Then the observer places the sample S on the stage 11. Next, an optical filter FL is inserted in the optical path of the image forming optical system 31.

Here, a wavelength band (transmission property) of the optical filter FL is assumed that the center wavelength is 550 nm and the wavelength width is ±20 nm. Next the image processing device 40 is activated. These steps may be performed in random order.

The observer inputs information of observation starting to the image processing device 40. Here, information of the in-focus position is assumed to be stored in the image processing device 40 beforehand. The image processing device 40 calculates the amount of movement based on the current position of the revolver 33 (microscope objective lens 35) and the information on the in-focus position. Based on the calculation result, the image processing device 40 transmits a driving signal to the motor 12. Based on the signal transmitted, the motor 12 moves the revolver 33 so that the position of the sample S coincides with the in-focus position. The in-focus position at this time can be considered as the position where focusing is established using the light having the wavelength band of 550 nm±20 nm (light of the first wavelength band).

Next, the optical filter FL is taken out of the optical path of the image forming optical system 31, and instead the optical filter FL' is inserted. Here, a wavelength band (transmission property) of the optical filter FL' is assumed that the center wavelength is 650 nm and the wavelength width is ±20 nm. In this case, the wavelength band of the optical filter FL' is different from the wavelength band of the optical filter FL.

When the optical filter FL' is inserted in the optical path, an optical image of the sample is formed using the light of the second wavelength band. Then, an electronic image is acquired using the light of the second wavelength band. Accordingly, the wavelength band of light is made to be different between before acquisition of an electronic image and at a time of acquisition of the electronic image (moment). As a result, it is possible to observe the sample S (image of the sample S) clearly.

A wavelength-variable interference filter can be used as the optical filter FL. The wavelength-variable interference filter is an optical filter whose wavelength band (transmission property) can be changed. By using the wavelength-variable interference filter, it is possible to eliminate the necessity of exchanging the optical filter FL and the optical filter FL'.

The sample observation method may be configured as follows. The sample is illuminated with white light (light of the first wavelength band) and the position of the sample S is allowed to coincide with the in-focus position. Then, the optical filter FL is inserted in the optical path of the image forming optical system 31. When the optical filter FL is inserted in the optical path, an optical image of the sample is formed using the light of the second wavelength band. In this case, the wavelength band of the optical filter FL is different from the wavelength band of the optical filter FL'. Therefore, the wavelength band of light is made to be different between before acquisition of an electronic image and at a time of acquisition of the electronic image (moment). As a result, it is possible to observe the sample S (image of the sample S) clearly.

The sample observation method may be configured as follows. The optical filter FL is inserted in the optical path of the illumination optical system 22, and the position of the sample S is allowed to coincide with the in-focus position. Then, the optical filter FL is taken out of the optical path of the illumination optical system 22, and instead an optical filter FL' is inserted in the optical path of the image forming optical system 31. When the optical filter FL' is inserted in the optical path, an optical image of the sample is formed using the light of the second wavelength band. In this case, the wavelength band of the optical filter FL is different from the wavelength band of the optical filter FL'. Therefore, the wavelength band of light is made to be different between before acquisition of an electronic image and at a time of acquisition of the electronic image (moment). As a result, it is possible to observe the sample S (image of the sample S) clearly.

As stated above, according to the sample observation device of the fifth embodiment, it is possible to observe a colorless and transparent sample more clearly in the state of bright-field observation as well.

Figure 29A:
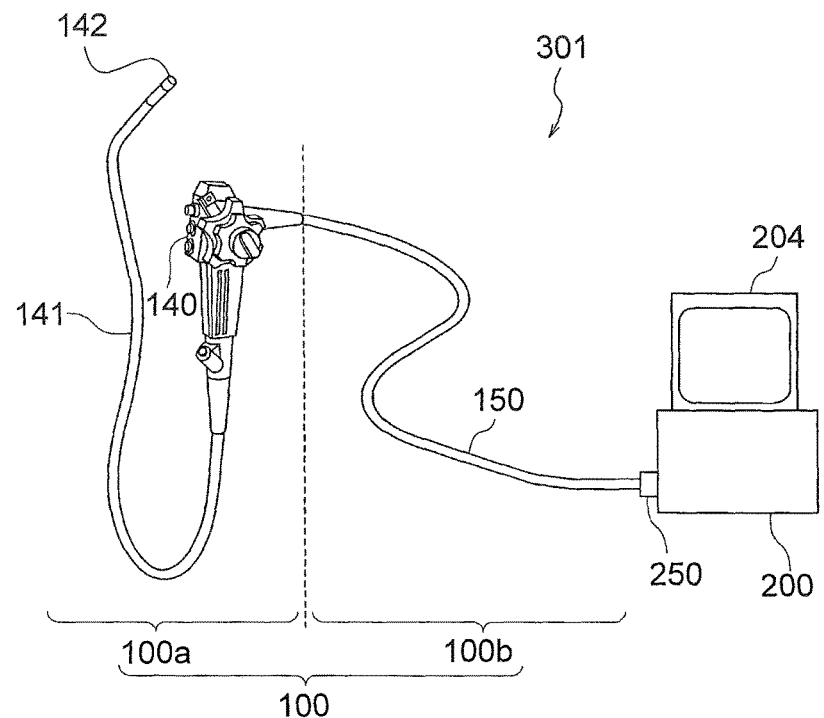
FIG. 29A and FIG. 29B are diagrams showing a configuration of a sample observation device of the sixth embodiment, where
Figure 29B:
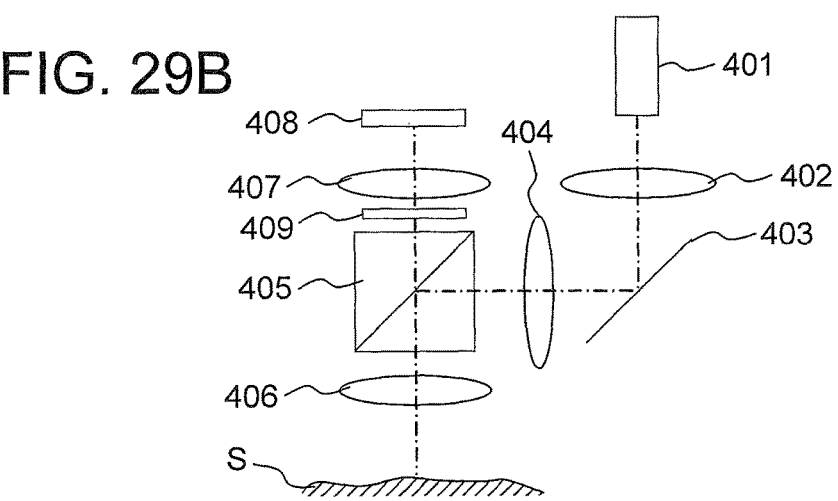

The configuration of a sample observation device of the sixth embodiment is shown in FIG. 29A and FIG. 297B. A sample observation device 301 is an observation system based on an electronic endoscope. FIG. 29A is a diagram showing the schematic configuration of the observation device, and FIG. 29B is a diagram showing the configuration of the optical system. The same reference numerals are assigned to the same components as those of the sample observation device 300, and their descriptions are omitted.

In a sample observation device 301, an illumination part includes a light source and an illumination optical system. Light from the light source emanates from an optical fiber 401. The illumination optical system includes a lens 402, a mirror 403, a lens 404, a half prism 405 and an objective lens 406. An observation part includes an image forming optical system and an image-pickup device. The image forming optical system includes the objective lens 406, the half prism 405, an image forming lens 407, and an optical filter 409. The image-pickup device includes an image-pickup element 408. In this optical system, a sample S is illuminated with epi-illumination.

The procedure to implement a sample observation method of one embodiment is described using the sample observation device 301. In the following description, the sample observation method of the eleventh embodiment is used as an example. A white light source is used as the light source.

Firstly, an observer sets the illumination optical system and the image forming optical system in the state of a bright-field observation. Then the observer moves the insertion part 141 by eye to the position where the observer thinks it as the in-focus position. Next, the image processing device 200 is activated. These processing steps may be performed in random order.

When the image processing device 200 is activated, the sample observation device is ready to pick up an image of the sample S, and so the acquisition step S10 is executed. By the acquisition step S10 is executed, an electronic image is acquired. The electronic image acquired at the acquisitions step S10 is stored in a temporary storage unit (not shown) in the image processing device 200.

Next, the subtraction step S20 is executed. At the subtraction step S20, by the value of $A_1^2$ is made to be small, the value of $2A_1A_2 \cos \psi$ becomes relatively large with reference to the value of $A_1^2+A_2^2$.

After the subtraction step S20 ends, the amplification step S30-2 is executed. At the amplification step S30-2, the value of $2A_1A_2 \cos \psi$ is made larger (amplified). Accordingly, the value of $2A_1A_2 \cos \psi$ becomes relatively larger with reference to the value of $A_1^2+A_2^2$. The execution result at the amplification step S30-2 is displayed on the display unit 204, for example.

While the insertion part 141 is moved, image-pickup is continuously performed. Therefore, the acquisition step S10, the subtraction step S20 and the amplification step S30-2 also are continuously executed. Then the observer can move the insertion part 141 while viewing an electronic image on the display unit 204 so as to let the position of the sample S coincide with the in-focus position. At this time, since optical filter is not disposed in the optical path of the illumination optical system 22, the sample S is illuminated with white light (light of the first wavelength band). The in-focus position at this time can be considered as a position where focusing is established with green light (light with wavelength of 500 nm to 560 nm).

Next, an optical filter FL is inserted in the optical path of the illumination optical system 22. Here, a wavelength band (transmission property) of the optical filter FL is assumed that the center wavelength is 650 nm and the wavelength width is ±20 nm. In this case, the wavelength band of the optical filter FL coincides with a part of the wavelength band of white light.

When the optical filter FL is inserted in the optical path, an optical image of the sample is formed using the light of the second wavelength band. Then, an electronic image is acquired using the light of the second wavelength band. Accordingly, the wavelength band of light is made to be different between before acquisition of an electronic image and at a time of acquisition of the electronic image (moment). As a result, it is possible to observe the sample S (image of the sample S) clearly.

At least one of the objective lens 406, the image-pickup lens 407 and the image-pickup element 408 may be moved along the optical axis. A micro-actuator (not shown) or a voice coil motor (not shown) may be used to move them. By doing so, it is possible to adjust the in-focus state finely. Therefore, the movement of the insertion part 141 can be stopped when an electronic image of contrast to certain extent is acquired.

As stated above, according to the sample observation device of the sixth embodiment, it is possible to observe a colorless and transparent sample more clearly in the state of bright-field observation as well.

In these sample observation devices of the fourth embodiment to the sixth embodiment, the following conditional expression (5) is satisfied preferably:

$$10 \ \mu m < d/NA_{ob}^2 < 1000 \ \mu m \quad (5)$$

Where d denotes an amount of axial chromatic aberration of the second wavelength band with reference to the first wavelength band, and $NA_{ob}$ denotes the numerical aperture of the image forming optical system on the sample side.

By satisfying of the conditional expression (5), it is possible to observe a colorless and transparent sample more clearly in the state of bright-field observation as well.

When falling below a lower limit value of the conditional expression (5), a difference in the amount of wavefront aberration between at the first wavelength band and at the second wavelength band is too small. In this case, the amount of wavefront aberration added to the diffracted light is small. Especially, the amount of wavefront aberration added to the first-order diffracted light becomes smaller than $\lambda/4$. Therefore, it becomes difficult to acquire an electronic image with good contrast.

When exceeding the upper limit of the conditional expression (5), the difference in the amount of wavefront aberration between at the first wavelength band and at the second wavelength band is too large. In this case, the amount of wavefront aberration added to the diffracted light is large. Especially, the amount of wavefront aberration added to the first-order diffracted light becomes larger than λ/4. Moreover, since an amount of aberration becomes too large, an optical image is defocused greatly. As a result, it becomes difficult to acquire an electronic image with high resolution.

In the sample observation devices from the fourth embodiment to the sixth embodiment as stated above, it is preferable that the image forming optical system includes an objective lens, and the axial chromatic aberration at the objective lens changes monotonously with wavelength.

By doing so, it is possible to acquire an electronic image with good contrast. When the axial chromatic aberration at the objective lens changes monotonously with wavelength, it is easy to understand a change in curve of the wavefront aberration due to wavelength. Therefore, at the time of selecting the second wavelength band, it is possible to select a wavelength band so as to have high contrast and high resolution easily.

In the sample observation devices from the fourth embodiment to the sixth embodiment as stated above, it is preferable that the image-pickup device includes an image-pickup element, and in the image-pickup device, a minute optical filter having a different wavelength band is displaced for each pixel.

By doing so, it is possible to acquire an electronic image with good contrast easily. In the image-pickup element, an optical filter is disposed. This optical filter includes a plurality of minute optical filters. These minute optical filters include red filters, green filters and blue filters, for example. Further, a plurality of minute optical filters are disposed in each color.

Therefore, an image signal may be extracted from these color filters for each color, whereby an optical image can be taken easily using light of the second wavelength band. That is, there is no need to dispose an optical filter in the optical path of the illumination optical system and the optical path of the image forming optical system. The image-pickup element may be a monochrome image-pickup element.

The present invention may have various modification examples without departing from the gist of the invention.

According to the present invention, it is possible to provide a sample observation method and a sample observation device enabling observation of a colorless and transparent sample, such as cells, in the state of bright-field observation as well.

As stated above, the present invention is suitable to a sample observation method and a sample observation device enabling observation of a colorless and transparent sample, such as cells, in the state of bright-field observation as well.

What is claimed is:

1. A sample observation method, comprising:
    acquiring an electronic image of a sample with a sensor in a state of bright-field observation, and
    acquiring a subtracted image of the sample at a second wavelength band with the sensor by subtracting a DC component from a signal of the electronic image to form an image in a predetermined state,
    wherein
    the predetermined state is a state in which an in-focus position of an image forming optical system at a first wavelength band is coincident with a position of the sample, and an in-focus position of an image forming optical system at the second wavelength band is different from the position of the sample,
    the second wavelength band is coincident with a part of the first wavelength band, or is different from the first wavelength band, and
    the in-focus position is a position where, at a spatial frequency which is included in the sample, an amount of wavefront aberration in zero-order diffracted light and an amount of wavefront aberration in first-order diffracted light are both 0.

2. The sample observation method according to claim 1, further comprising:
    an amplification step after the step of forming the image in the second predetermined state,
    wherein
    at the amplification step, a signal of an electronic image subjected to the step of forming the image in the second predetermined state is amplified.

3. The sample observation method according to claim 1, further comprising:
    performing Fourier transform, with an image processor, of a signal of the electronic image, and
    performing inverse Fourier transform, with the image processor,
    wherein
    performing Fourier transform of the signal prior to the step of forming the image in the second predetermined state, and
    performing inverse Fourier transform at least after the step of forming the image in the second predetermined state.

4. The sample observation method according to claim 1, further comprising:
    an acquisition in advance step, and
    a normalization step,
    wherein
    at the acquisition in advance step, an electronic image is acquired without the sample,
    at the normalization step, using the electronic image, an electronic image of the sample is normalized, and
    the normalization step is performed prior to the step of forming the image in the second predetermined state.

5. The sample observation method according to claim 1, wherein
    the second wavelength band is changed with reference to the first wavelength band a plurality of times,
    at each second wavelength band after changing, the step of acquiring the electronic image of the sample and the step of forming the image in the second predetermined state are performed, and thereby a plurality of electronic images are generated after the step of forming the image in the second predetermined state, and
    the plurality of electronic images generated are added.

6. The sample observation method according to claim 5, wherein
    before the addition, a part with highest contrast in each of the plurality of electronic images is extracted, and
    addition is performed using the extracted parts.

7. The sample observation method according to claim 5, wherein
    a change of the second wavelength band is made while keeping a sign of the amount of wavefront aberration in the second predetermined state same.

8. A sample observation device, comprising:
    a light source,
    an illumination optical system,
    an image forming optical system,
    a sensor, and
    an image processor,
    wherein the illumination optical system is disposed so as to irradiate a sample with illumination light from the light source, the image forming optical system is disposed so that light from the sample is incident thereon and an optical image of the sample is formed, the sensor is disposed at a position of the optical image, and the image processor is configured to perform the steps of the sample observation method according to claim 1.

9. The sample observation device according to claim 8, further comprising a display device, wherein the display device displays an output signal from the image processor.

10. The sample observation device according to claim 8, wherein the following conditional expression 1 is satisfied:

$$10 \ \mu m < d/NA_{ob}^2 < 1000 \ \mu m \qquad 1$$

Where d denotes an amount of axial chromatic aberration of the second wavelength band with reference to the first wavelength band, and $NA_{ob}$ denotes a numerical aperture of the image forming optical system on the sample side.

11. The sample observation device according to claim 8, wherein the image forming optical system includes an objective lens, and axial chromatic aberration at the objective lens changes monotonously with wavelength.

12. The sample observation device according to claim 8, wherein in the sensor, a minute optical filter having a different wavelength band is displaced for each pixel.

* * * * *